United States Patent
Kornberg et al.

(10) Patent No.: US 6,642,256 B2
(45) Date of Patent: Nov. 4, 2003

(54) PIPERIDINE DERIVATIVES AS SUBTYPE SELECTIVE N-METHYL-D-ASPARTATE ANTAGONISTS

(75) Inventors: Brian Edward Kornberg, Ann Arbor, MI (US); Russell Andrew Lewthwaite, Cambridge (GB); David Manning, Duanesburg, NY (US); Sham Shridhar Nikam, Ann Arbor, MI (US); Ian Leslie Scott, Delanson, NY (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 09/998,479

(22) Filed: Nov. 30, 2001

(65) Prior Publication Data

US 2003/0018021 A1 Jan. 23, 2003

Related U.S. Application Data

(60) Provisional application No. 60/257,832, filed on Dec. 21, 2000.

(51) Int. Cl.$^7$ .................. A01N 43/40; C07D 401/00; C07D 211/44
(52) U.S. Cl. .................. 514/317; 514/322; 514/326; 514/327; 514/321; 546/192; 546/201; 546/209; 546/211; 546/216; 546/217
(58) Field of Search .................. 546/201, 209, 546/211, 192, 216, 217; 514/321, 322, 326, 327, 317

(56) References Cited

U.S. PATENT DOCUMENTS

| 5,714,502 A | 2/1998 | Prücher et al. ............. 514/326 |
| 6,015,824 A | 1/2000 | Alanine et al. ............. 514/375 |
| 6,124,317 A | 9/2000 | Bigge et al. ............. 514/317 |
| 6,124,323 A | 9/2000 | Bigge et al. ............. 514/327 |
| 6,130,234 A | 10/2000 | Bigge et al. ............. 514/322 |

FOREIGN PATENT DOCUMENTS

| EP | 0763535 | 8/1996 | ................ 546/211 |
| EP | 0937458 | 2/1999 | |
| WO | 9616040 | 5/1996 | ................ 546/211 |
| WO | 9912924 | 3/1999 | |
| WO | 9948891 | 9/1999 | |
| WO | 9950264 | 10/1999 | ................ 546/211 |
| WO | 0018763 | 4/2000 | ................ 546/211 |

OTHER PUBLICATIONS

PCT International Search Report, PCT/IB01/02277.

Prücher et al., "(5S)-3-Aryl-5-(1-piperidinylmethyl)-2-oxazolidinones, a new class of potential neuroleptics with a high affinity for sigma receptors", *Bioorganic & Medicinal Chemistry Letters*, vol. 2, No. 2, 1992, pp. 165–170.

*Primary Examiner*—Alan L. Rotman
*Assistant Examiner*—Raymond Covington
(74) *Attorney, Agent, or Firm*—Charles W. Ashbrook; David R. Kurlandsky

(57) ABSTRACT

Described are piperidines of Formula I

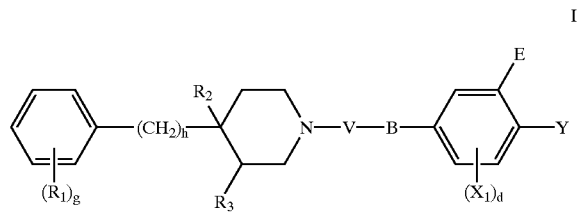

and pharmaceutically acceptable salts thereof. The compounds of Formula I are antagonists of NMDA receptor channel complexes useful for treating cerebral vascular disorders such as, for example, stroke, cerebral ischemia, central nervous system disorders, depression, trauma, hypoglycemia, neurodegenerative disorders, anxiety, migraine headache, convulsions, Parkinson's disease, aminoglycoside antibiotics-induced hearing loss, psychosis, glaucoma, CMV retinitis, opioid tolerance or withdrawal, pain, especially chronic pain, neuropathic pain, or surgical pain, or urinary incontinence.

8 Claims, No Drawings

PIPERIDINE DERIVATIVES AS SUBTYPE SELECTIVE N-METHYL-D-ASPARTATE ANTAGONISTS

This application claims the benefit of provisional application Ser. No. 60/257,832 filed Dec. 21, 2000.

FIELD OF INVENTION

The invention relates to piperidine derivatives as N-Methyl-D-Aspartate (NMDA) antagonists useful in the treatment of diseases and disorders responsive to antagonism of NMDA receptors.

BACKGROUND OF THE INVENTION

Many of the physiological and pathophysiological effects of the endogenous excitatory neurotransmitter glutamate are mediated via actions at N-Methyl-D-Asparate (NMDA) receptors. Over-excitation of the NMDA receptors on postsynaptic cells-mediated by excessive release of glutamate from nerve endings or glial cells-results in a massive calcium ion influx through a calcium ion channel into neuronal cells, leading to neuronal cell death. These events occur under ischemic or hypoxic conditions such as, for example, stroke, hypoglycemia, cardiac arrest, or acute physical trauma.

NMDA receptors in vivo form an NMDA receptor channel complex in cell walls comprising at least three binding domains, including a glutamic acid (or NMDA) recognition site, a channel blocking binding site, and a strychnine-insensitive glycine binding site. Physiologically, a blockade of at least one of these sites terminates the channel opening of the NMDA receptor, thereby preventing calcium ion influx into cells. Accordingly, an NMDA receptor antagonist is therapeutically useful because it minimizes damage to the central nervous system induced by calcium ion influx under ischemic or hypoxic conditions.

A functional NMDA receptor is comprised of the combination of at least one subunit termed "NR1", which has 8 splice variants including NR1A, and one (or more) subunit termed "NR2A", "NR2B", "NR2C", and "NR2D". The combinations are designated NR1/2A, NR1/2B, NR1/2C and NR1/2D, respectively. The different NR2 subunits have distinct developmental and anatomical distributions. This suggests that agents that selectively antagonize one NR1/NR2 combination would have therapeutic actions without the psychotomimetic or dysphoric side effects associated with antagonists which block multiple NR1/NR2 combinations.

A subtype-selective NMDA receptor antagonist may be identified by methods well known in the pharmaceutical arts, such as, for example, screening compounds in an electrophysiology assay. In one such electrophysiology assay, different subunit combinations of recombinant NR1 and NR2 receptors are expressed in Xenopus oocytes, and a potential agent is administered at different concentrations. NMDA-based electrical currents are activated by co-administration of fixed concentrations of an excitatory amino acid such as, for example, glutamic acid or glycine. The ability of an agent to antagonize the activation of the electrical current by an excitatory amino acid is measured by recording the change in the current versus the change in the concentration of the agent.

Screening of compounds in recent years have identified a number of NMDA receptor antagonists that have been used in animal and clinical human studies to demonstrate proof of concept for use of such an antagonist in the treatment of a variety of disorders. Disorders known to be responsive to blockade of NMDA receptors include acute cerebral ischemia (stroke or cerebral trauma, for example), muscular spasm, convulsive disorders, pain, including chronic and neuropathic pain, anxiety, and chronic neurodegenerative disorders such as Parkinson's disease. NMDA receptor antagonists may also be used to prevent tolerance to opiate analgesia or to help control symptoms of withdrawal from addictive drugs. In fact, excessive excitation by neurotransmitters may be responsible for the loss of neurons in a wide variety of conditions. Additional conditions include cerebral vascular disorders such as cerebral ischemia or cerebral infarction resulting in a range of conditions such as thromboembolic or hemorrhagic stroke, cerebral vasospasm, hypoglycemia, cardiac arrest, status epilepticus, perinatal, asphyxia anoxia, such as from near drowning, pulmonary surgery and cerebral trauma, as well as lathyrism, Alzheimer's disease, and Huntington's disease. Other conditions amendable to treatment with an subtype-selective NMDA receptor antagonist include amyotrophic lateral sclerosis (ALS), epilepsy, and schizophrenia.

For example, studies have demonstrated that compounds that act as antagonists at NMDA receptors have beneficial pharmacological effects on patients suffering from Parkinson's disease. In Parkinson's disease, there is a loss of dopamine neurons in the substantia nigra. Secondary to this dopamine loss is a hyperactivity of specific brain glutamatergic pathways. This glutamatergic hyperactivity is thought to mediate some of the pathophysiological aspects of Parkinson's disease, as well as some of the side effects associated with the long term treatment of the disease by dopamine agonists, such as L-DOPA, pergolide, ropinirole or pramipexole. Clinical studies in humans have demonstrated that antagonists at NMDA receptors have beneficial effects in Parkinson's disease or in treating the side effects associated with the treatment of Parkinson's disease with dopamine agonists.

Pain is another example of a condition shown to be responsive to NMDA receptor antagonism. For example in previous studies, stimulation of NMDA receptors by afferent nerves transmitting painful stimuli has been demonstrated to be involved in hyperalgesic and neuropathic pain states. Animal studies have demonstrated that compounds that act as antagonists at NMDA receptors have beneficial effects in treating hyperalgesic and neuropathic pain states.

However, while NMDA antagonists have been successfully used to demonstrate the proof of concept mentioned above, very few, if any, of these antagonists have shown a suitable drug profile in clinical studies. This is so even though numerous NMDA receptor antagonists have been synthesized and tested. For example, U.S. Pat. Nos. 5,714,502; 6,124,317; 6,124,323; and 6,130,234 describes the piperidine-based NMDA receptor antagonists shown below.

U.S. Pat. No. 5,714,502 provides piperidines of formula

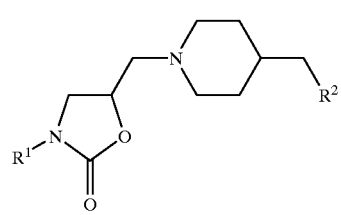

in which
R$^1$ and R$^2$ in each case independently of one another are unsubstituted or mono- to disubstituted phenyl radicals whose substituents can be A, OA, aryloxy having 6 to 10 C atoms, aralkyloxy having 7 to 11 C atoms, —O—(CH$_2$)$_n$—O—(bonded in directly adjacent positions or in the meta- or para-position to one another on the phenyl ring), —O—(CH$_2$)$_n$—OH, Hal, CF$_3$, OH, NO$_2$, NH$_2$, NHA, NA$_2$, NHR$^3$, NAR$^3$, SO$_2$NH$_2$, SO$_2$NHA, SO$_2$NA$_2$, SO$_2$NHR$^3$ (excluding R$^3$=SO$_2$A), SO$_2$N(R$^3$)$_2$ (excluding R$^3$=SO$_2$A) or R$^3$, R$^3$ is COH, CO-alkyl having 1 to 7 C atoms in the alkyl portion, CO-alkyl-aryl having 8 to 12 C atoms in the alkyl and aryl portions, CO-aryl having 7 to 13 C atoms in the aryl portion, or SO$_2$A A is an alkyl radical having 1 to 6 C atoms n is 1 or 2

Hal is F, Cl, Br, or I, and their physiologically acceptable salts. The invention also relates to the preparation of these novel compounds and their use as psychopharmacologically active substances.

U.S. Pat. No. 6,124,317 provides 2-substituted piperidine NMDA receptor antagonists of formula

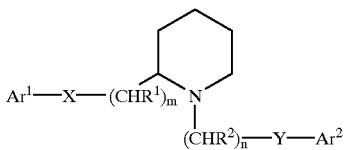

or a pharmaceutically acceptable salt thereof wherein

Ar$^1$ and Ar$^2$ are independently aryl or a heteroaryl group, either of which may be independently substituted by hydrogen, hydroxy, alkyl, a halogenated alkyl group, halogen, nitro, aryl, aralkyl, amino, a lower alkyl amino group or a lower alkoxy group;

each R$^1$ is independently hydrogen, alkyl or hydroxy;

each R$^2$ is independently hydrogen, alkyl or hydroxy;

X is —CH$_2$—, O, S, or NR$^3$, wherein R$^3$ is hydrogen or a lower alkyl group having 1 to 6 carbon atoms;

Y is —CH$_2$—, —CH=CH—, —C≡C—, O, S or NR$^3$;

m is 0, 1 or 2; and n is 0, 1, 2, 3, 4 or 5, provided that when m is 0 and X is —CH$_2$—, or m is 1, R$^1$ is H and X is —CH$_2$— that either Y is not —CH$_2$— or at least one of R$^2$ is not hydrogen and further provided that when Y is —C=C— then X is not O.

U.S. Pat. No. 6,124,323 provides 4-substituted piperidine-based NMDA receptor antagonists of formula

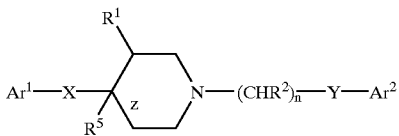

or a pharmaceutically acceptable salt thereof wherein

Ar$^1$ and Ar$^2$ are independently aryl or a heteroaryl group, either of which may be independently substituted by hydrogen, hydroxy, alkyl, halogen, nitro, cyano, carboxaldehyde, aldehyde oxime, lower alkoxy carbonylmethyl, hydroxy lower alkyl, amino carbonylmethyl, hydrazinocarbonylmethyl, acetamido, aryl, aralkyl, amino, a halogenated alkyl group, a lower alkyl amino group or a lower alkoxy group;

z is a single or double bond;

X is —(CHR$^3$)$_m$—, O, S or NR$^4$, wherein each R$^3$ is independently hydrogen, hydroxy or a lower alkyl group having 1 to 6 carbon atoms, R$^4$ is hydrogen or a lower alkyl group having 1 to 6 carbon atoms and m is 0, 1 or 2, provided that when z is a double bond then X is not O or NR$^4$;

R$^1$ is hydrogen or hydroxy;

each R$^2$ is independently hydrogen, hydroxy or a lower alkyl group having 1 to 6 carbon atoms;

n is 0, 1, 2, 3 or 4;

Y is O, S, NR$^4$ or a single bond; and

R$^5$ is hydrogen or hydroxy when z is a single bond preferably provided that:

(i) R$^2$ cannot be hydroxy in a position alpha to Ar$^2$; (ii) if X is a single bond, z is a double bond or R$^5$ is hydroxy and Ar$^2$ is phenyl then Y cannot be O; (iii) if Y is O, n is 3 or 4, R$^2$ is exclusively hydrogen, z is a single bond, R$^1$ and R$^5$ are hydrogen and Ar$_2$ is phenyl, or halogen, methoxy, or trifluoromethyl substituted phenyl then X cannot be methylene or ethylene; (iv) if X is —(CHR$^3$)$_m$—, m is 2 and R$^3$ is exclusively hydrogen then Ar$^1$ cannot be imidazolyl substituted; (v) if Y is O, n is 2, 3 or 4, R$^2$ is hydrogen or hydroxy, z is a single bond, R$^1$ and R$^5$ are hydrogen, and Ar$^2$ is phenyl, or NO$_2$, CN, 1-imidazoyl, or 1,2,4-triazol-1-yl substituted phenyl then X cannot be methylene, hydroxymethylene, or O; (vi) if Y is O or S, R$^1$ and R$^5$ are hydrogen and R$^2$ is hydroxy then X is not methylene or a single bond; or (vii) if Y is a single bond, R$^2$ is exclusively hydrogen and Ar$^2$ is phenyl, then either R$^1$ or R$^5$ must be hydroxy.

U.S. Pat. No. 6,130,234 provides piperidine-based NMDA receptor antagonists of formula

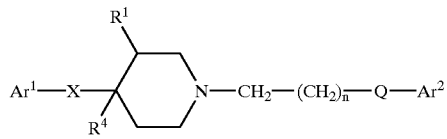

or a pharmaceutically acceptable salt thereof wherein

Ar$^1$ and Ar$^2$ are independently aryl or a heteroaryl group, either of which may be independently substituted by hydrogen, hydroxy, alkyl, halogen, nitro, aryl, aralkyl, amino, a halogenated alkyl group, —NHAc, —NHSO$_2$Me, —N(SO$_2$Me)$_2$, —CONHalkyl, —SO$_2$NH$_2$, an alkylguanidine group, a lower alkyl amino group or a lower alkoxy group;

z is a single or double bond;

X is —(CHR$^2$)$_m$—, O, S or NR$^3$, wherein each R$^2$ is independently hydrogen, hydroxy, lower alkoxy or a lower alkyl group having 1 to 6 carbon atoms and m is 0, 1 or 2, and R$^3$ is hydrogen or a lower alkyl group having 1 to 6 carbon atoms, provided that when z is a double bond then X is not O, S or NR$^3$;

R$^1$ is hydrogen or hydroxy;

n is 0, 1 or 2;

Q is —CH=CH— or —C≡—C—; and

R$^4$ is hydrogen or hydroxy when z is a single bond provided that: (i) when n is 0, then z is a double bond and R$^4$ is not present; (ii) when n is 1 or 2 and Q is —C≡C— and z is a double bond or R$^4$ is hydroxy, then Ar$^1$ is aryl substituted by halogen; and (iii) when R$^4$ is hydroxy then R$^2$ is not hydroxy or lower alkoxy.

The difficulty referenced above with demonstrating clinical utility of NMDA receptor antagonists has been the antagonists' lack of NMDA receptor subtype selectivity and/or biological activity when dosed orally. Before the present invention, many of the drugs of the NMDA receptor antagonist class were nonselective antagonists of NMDA receptor subtypes that were administered intravenously (IV), which accounts for their undesired side effects and lack of efficacy, respectively. Given that the need for medicinal agents that treat diseases responsive to antagonism of NMDA receptors remains unmet, the search for NMDA receptor antagonists that are subtype-selective and orally efficacious continues.

A series of novel piperidines have been discovered that are subtype-selective NMDA receptor antagonists and are efficacious in vivo when dosed orally. All that is needed to practice the invention is to administer from 1 to 6 times daily to a patient in need thereof, a therapeutically effective amount of a compound of the invention. As is discussed below, determination of dosage forms and amounts of the invention compounds, routes of administration, and identification of patients in need of treatment, is within the average skill in the pharmaceutical and medical arts.

SUMMARY OF THE INVENTION

Described are piperidines of Formula I

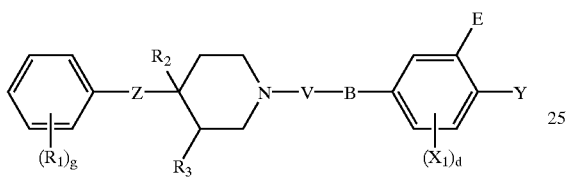

and pharmaceutically acceptable salts thereof wherein:

$R_1$ is independently selected from alky, substituted alkyl, alkenyl, substituted alkenyl, alkoxy, substituted alkoxy, alkylaminoalkyl, hydroxyalkyl, (aminocarbonyl)-alkyl, (alkylthio)-alkyl, carboxyalkyl, haloalkyl, and halogen;

g is an integer of from 0 to 3;

Z is $(CH_2)_h$, C=O, O, S, SO, $SO_2$, CHOH, or C(Me)OH;

h is an integer of from 0 or 1;

$R_2$ is hydrogen, OH, alkoxy, or substituted alkoxy;

$R_3$ is hydrogen, OH, alkoxy, or substituted alkoxy;

V is $(CH_2)_n$ or $(CH_2)_m$—C=O, wherein n is an integer of from 1 to 4, and m is an integer of from 0 to 4;

B is a 4-, 5-, or 6-membered, carbon-linked, substituted or unsubstituted, heterocyclene, containing from 1 to 3 heteroatoms, which are N, O, or S, selected from the group consisting of:

(i) 1-aza-2-cyclobutanon-3,4-diyl of formula

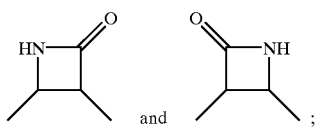

(ii) a 5-membered aromatic, nonaromatic dihydro, or nonaromatic tetrahydro diradical heterocyclic ring having carbon atoms and from 1 to 3 heteroatoms selected from N, O, and S;

(iii) a 5-membered oxo-substituted, nonaromatic tetrahydro, diradical heterocyclic ring having carbon atoms and 1 or 2 heteroatoms selected from N, O, and S;

(iv) a 6-membered aromatic, nonaromatic tetrahydro, or nonaromatic hexahydro diradical heterocyclic ring having carbon atoms and 1 or 2 heteroatoms, which heteroatoms are nitrogen, and (v) a 6-membered nonaromatic oxo-substituted hexahydro diradical heterocyclic ring having carbon atoms and 1 or 2 heteroatoms which are nitrogen and 0 or 1 heteroatom which is oxygen wherein the atoms of the heterocyclene ring that are bonded to the group V and the phenyl bearing the group $(X_1)_d$ are carbon atoms, and further wherein when B is a nonaromatic heterocycle containing sulfur, said sulfur may further comprise

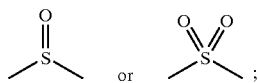

$X_1$ is alkyl, substituted alkyl, alkenyl, substituted alkenyl, alkoxy, substituted alkoxy, aralkyl, substituted aralkyl, halogen, haloalkyl, cyano, nitro, amino, aminoalkyl, alkylaminoalkyl, hydroxyalkyl, carboxyalkyl, (aminocarbonyl)-alkyl, (alkylthio)-alkyl, or C(O)-alkyl;

d is an integer of from 0 to 2;

E is hydrogen; and

Y is OH; or

E and Y may be taken together with the phenylene to which they are attached to form a fused 9- or 10-membered bicyclic ring, containing from 0 to 3 heteroatoms in E to Y selected from N, O, and S, wherein E is a linker group containing 2 or 3 atoms of the bicyclic ring, and Y is a hydrogen bond donor group containing 1 atom of the bicyclic ring.

Preferred is a compound of Formula I wherein:

B is a heterocyclene selected from the group consisting of:

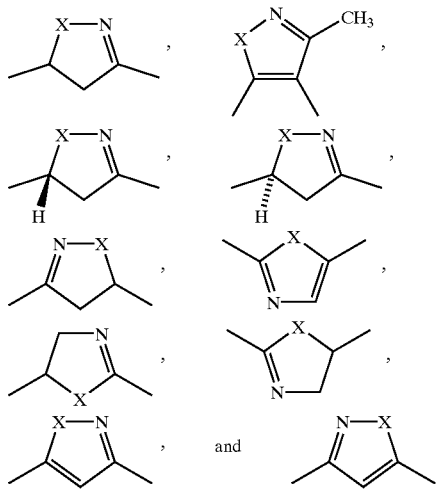

wherein X is selected from O, S, and N—R, wherein R is hydrogen or alkyl;

$X_1$ is alkyl, substituted alkyl, alkenyl, substituted alkenyl, alkoxy, substituted alkoxy, aralkyl, halogen, haloalkyl, cyano, nitro, amino, aminoalkyl, alkylaminoalkyl, hydroxyalkyl, carboxyalkyl, (aminocarbonyl)-alkyl, (alkylthio)-alkyl, or $C(O)CH_3$, and one $X_1$ is ortho to V and para to E; and $R_2$ is hydrogen or OH;

$R_3$ is hydrogen or OH;

V is $CH_2$ or C=O;

Z is $(CH_2)_h$; and h is 1.

Preferred is a compound of Formula II

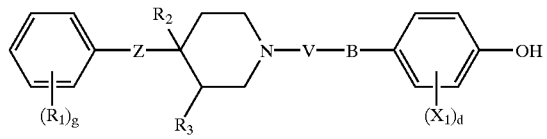

II and pharmaceutically acceptable salts thereof wherein $R_1$, g, Z, h, $R_2$, $R_3$, V, B, $X_1$, and d are as defined above for Formula I; and wherein when B is a 5-membered, oxo-substituted, nonaromatic tetrahydro, diradical heterocyclic ring having carbon atoms and 1 or 2 heteroatoms selected from N, O, and S which is an oxazolidinone, the oxazolidinone is selected from:

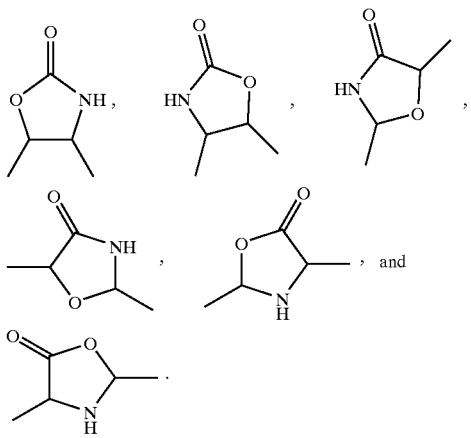

Also preferred is a compound of Formula III

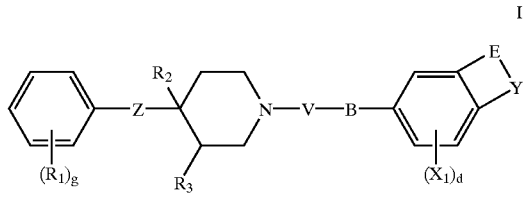

III and pharmaceutically acceptable salts thereof wherein $R_1$, g, Z, h, $R_2$, $R_3$, V, B, $X_1$, and d are as defined above for Formula I; and
E and Y together with the phenylene to which they are attached form a 9- or 10-membered bicyclic ring, containing from 0 to 3 heteroatoms selected from N, O, and S wherein
  E is a linker group containing 2 or 3 atoms of the bicyclic ring; and
  Y is a hydrogen bond donor group containing 1 atom of the bicyclic ring.
More preferred is a compound of Formula III wherein
Y is selected from —N(H)—, —CH(OH)—, and —N(OH)—, and
E is selected from —CH=CH—, —CH$_2$—CH$_2$—, —CH=N—, —C(O)—CH$_2$—, —CH$_2$—C(O)—, —CH$_2$—S(O)—, —CH$_2$—S(O)$_2$—, —N=C(H)—, —N(H)—C(O)—, —O—C(O)—, —S—C(O)—, —N=N—, —CH=CH—C(H)—, —CH$_2$—CH$_2$—CH$_2$—, —CH$_2$—CH$_2$—C(O)—, —CH$_2$—CH$_2$—S(O)—, —CH$_2$—CH$_2$—S(O)$_2$—, —CH=CH—C(O)—, —N=CH—C(O)—, —O—CH$_2$—C(O)—, —S—CH$_2$—C(O)—, and —N(H)—C(O)—C(O)—; or
Y is selected from =C(OH)—; and
E is selected from —CH=CH—C(H)=, —C(O)—C(H)=, —C(O)—N=, —O—N=, —S—N=, —C(O)—N(H)—N=, —CH=N—N=, —CH=N(O)—N=, and —N(H)—C(O)—N=.

More preferred is a compound of Formula III wherein:
—E—Y— is selected from the group consisting of
  —CH=CH—N(H)—,
  —(CH$_2$)$_2$—N(H)—,
  —CH=N—N(H)—,
  —C(O)—CH$_2$—N(H)—,
  —CH$_2$—C(O)—N(H)—,
  —CH$_2$—S(O)—N(H)—,
  —CH$_2$—S(O)$_2$—N(H)—,
  —CH=CH—CH(OH)—,
  —(CH$_2$)$_2$—CH(OH)—,
  —C(O)—C(H)=C(OH)—,
  —C(O)—N=C(OH)—,
  —N=CH—N(H)—,
  —N(H)—C(O)—N(H)—,
  —O—C(O)—NH—,
  —S—C(O)—NH—,
  —O—N=CH(OH)—,
  —S—N=CH(OH)—,
  —N=N—N(H)—,
  —N=N—N(OH)—,
  —CH=CH—CH=C(OH)—,
  —(CH$_2$)$_3$—CH(OH)—,
  —(CH$_2$)$_2$—C(O)—N(H)—,
  —(CH$_2$)$_2$—S(O)—N(H)—,
  —(CH$_2$)$_2$—S(O)$_2$—N(H)—,
  —CH=CH—C(O)—N(H)—,
  —C(O)—NH—N=C(OH)—,
  —CH=N—N=C(OH)—,
  —CH=N(O)—N=C(OH)—,
  —N(H)—C(O)—N=C(OH)—,
  —N=CH—C(O)—NH—,
  —O—CH$_2$—C(O)—NH—,
  —S—CH$_2$—C(O)—NH—, and
  —N(H)—C(O)—C(O)—N(H)—.
Also preferred is a compound of Formula IV

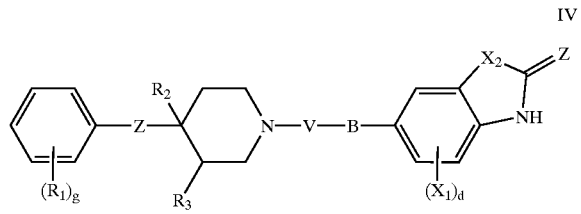

IV and pharmaceutically acceptable salts thereof wherein $R_1$, g, h, $R_2$, V, B, $X_1$, and d are as defined above for Formula I; and $X_2$ is selected from O, S, NH, and $CH_2$; and
B is selected from the group consisting of:

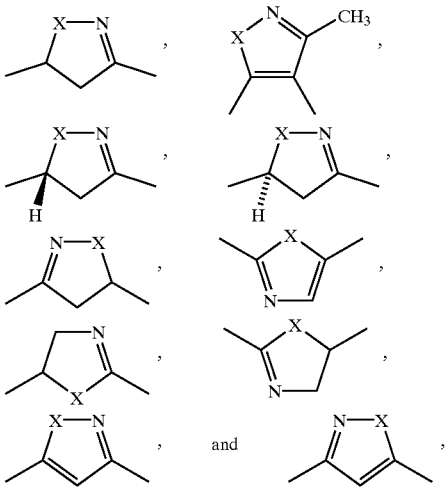

wherein X is selected from O, S, and N—R, wherein R is hydrogen or alkyl, and wherein Z is selected from O or S.

More preferred is a compound of Formula IV selected from the group consisting of:

6-[5-(4-Benzylpiperidin-1-ylmethyl)-4,5-dihydroisoxazol-3-yl]-3H-benzoxazol-2-one;
6-[5-(4-Benzylpiperidin-1-ylmethyl)-3-methylisoxazol-4-yl]-3H-benzoxazol-2-one;
6-{5-[4-(4-fluorobenzyl)piperidin-1-ylmethyl]-4,5-dihydroisoxazol-3-yl}-3H-benzoxazol-2-one hydrochloride;
(+)-6-{5-[4-(4-fluorobenzyl)piperidin-1-ylmethyl]-4,5-dihydroisoxazol-3-yl}-3H-benzoxazol-2-one;
(−)-6-{5-[4-(4-fluorobenzyl)piperidin-1-ylmethyl]-4,5-dihydroisoxazol-3-yl}-3H-benzoxazol-2-one;
6-{3-[4-(4-Fluorobenzyl)piperidin-1-ylmethyl]-4,5-dihydroisoxazol-5-yl}-3H-benzoxazol-2-one;
6-{2-[4-(4-Fluorobenzyl)piperidin-1-ylmethyl]thiazol-5-yl}-3H-benzoxazol-2-one;
6-{2-[4-(4-fluorobenzyl)piperidin-1-ylmethyl]thiazol-5-yl}-3H-benzothiazol-2-one;
5-[2-(4-Benzylpiperidin-1-ylmethyl)thiazol-5-yl]-1,3-dihydrobenzimidazole-2-thione;
6-{2-[4-(4-Fluorobenzyl)piperidin-1-ylmethyl]oxazol-5-yl}-3H-benzothiazol-2-one;
6-[2-(4-Benzylpiperidin-1-ylmethyl)oxazol-5-yl]-3H-benzoxazol-2-one;
5-[2-(4-Benzylpiperidin-1-ylmethyl)oxazol-5-yl]-1,3-dihydroindol-2-one;
6-{5-[4-(4-Fluorobenzyl)piperidin-1-ylmethyl]-4,5-dihydrothiazol-2-yl}-3H-benzoxazol-2-one;
6-[5-(4-Benzylpiperidin-1-ylmethyl)-4,5-dihydrothiazol-2-yl]-3H-benzoxazol-2-one;
6-[2-(4-Benzylpiperidin-1-ylmethyl)-4,5-dihydrothiazol-5-yl]-3H-benzoxazol-2-one;
6-{5-[4-(4-Fluorobenzyl)piperidin-1-ylmethyl]isoxazol-3-yl}-3H-benzoxazol-2-one;
6-{5-[4-(4-Fluorobenzyl)piperidin-1-yl]methyl}-4,5-dihydroisoxazol-3-yl}-3H-benzothiazol-2-one;
6-[5-(4-Benzyl-4-hydroxypiperidin-1-ylmethyl)-4,5-dihydroisoxazol-3-yl]-3H-benzoxazol-2-one;
6-{5-[4-(4-Fluorobenzyl)piperidine-1-carbonyl]-4,5-dihydroisoxazol-3-yl}-3H-benzoxazol-2-one;
6-(5-{2-[4-(4-Fluorobenzyl)piperidin-1-yl]ethyl}-4,5-dihydroisoxazol-3-yl)-3H-benzoxazol-2-one;
6-{5-[4-(4-Fluorobenzyl)-4-hydroxypiperidin-1-ylmethyl]-4,5-dihydroisoxazol-3-yl}-3H-benzoxazol-2-one;
6-{5-[4-(4-Fluorobenzyl)piperidin-1-ylmethyl]-5-methyl-4,5-dihydroisoxazol-3-yl}-3H-benzoxazol-2-one;
5-[4-(4-Fluorobenzyl)piperidin-1-ylmethyl]-3-(2-oxo-2,3-dihydrobenzoxazol-6-yl)-4,5-dihydroisoxazole-5-carboxylic acid;
5-[4-(4-Fluorobenzyl)piperidin-1-ylmethyl]-3-(2-oxo-2,3-dihydrobenzoxazol-6-yl)-4,5-dihydroisoxazole-5-carboxylic acid methyl ester;
4-(4-Fluorobenzyl)-1-[3-(2-oxo-2,3-dihydrobenzoxazol-6-yl)-4,5-dihydroisoxazol-5-ylmethyl]piperidine-4-carboxylic acid ethyl ester;
4-(4-Fluorobenzyl)-1-[3-(2-oxo-2,3-dihydrobenzoxazol-6-yl)-4,5-dihydroisoxazol-5-ylmethyl]piperidine-4-carboxylic acid;
6-{5-[4-(4-Fluorobenzyl)-3-hydroxypiperidin-1-ylmethyl]-4,5-dihydroisoxazol-3-yl }-3H-benzoxazol-2-one;
6-{5-[4-(4-Fluorophenoxy)piperidin-1-ylmethyl]-4,5-dihydroisoxazol-3-yl}-3H-benzoxazol-2-one;
6-{5-[4-(4-Fluorophenylsulfanyl)piperidin-1-ylmethyl]-4,5-dihydroisoxazol-3-yl}-3H-benzoxazol-2-one;
6-{5-[4-(4-Fluorobenzenesulfinyl)piperidin-1-ylmethyl]-4,5-dihydroisoxazol-3-yl}-3H-benzoxazol-2-one;
6-{5-[4-(4-Fluorobenzoyl)piperidin-1-ylmethyl]-4,5-dihydroisoxazol-3-yl}-3H-benzoxazol-2-one;
6-(5-{4-[(4-Fluorophenyl)hydroxymethyl]piperidin-1-ylmethyl}-4,5-dihydroisoxazol-3-yl)-3H-benzoxazol-2-one;
4-Chloro-6-{5-[4-(4-fluorobenzyl)piperidin-1-ylmethyl]-4,5-dihydroisoxazol-3-yl}-5-methyl-3H-benzoxazol-2-one;
-{5-[4-(4-Fluorophenyl)piperidin-1-ylmethyl]-4,5-dihydroisoxazol-3-yl}-3H-benzoxazol-2-one;
6-[5-(4-Phenyl-4-hydroxy)piperidin-1-ylmethyl)-4,5-dihydroisoxazol-3-yl]-3H-benzoxazol-2-one; and
6-(5-{2-[4-(4-Fluorophenyl)piperidin-1-yl]ethyl }-4,5-dihydroisoxazol-3-yl)-3H-benzoxazol-2-one.

More preferred is a compound of Formula IV named (−)-6-{5-[4-(4-fluorobenzyl)piperidin-1-ylmethyl]-4,5-dihydroisoxazol-3-yl}-3H-benzoxazol-3-one.

Still more preferred is a compound of Formula IV named (+)-6-{5-[4-(4-fluorobenzyl)piperidin-1-ylmethyl]-4,5-dihydroisoxazol-3-yl}-3H-benzoxazol-3-one.

Preferred is a compound of Formula V

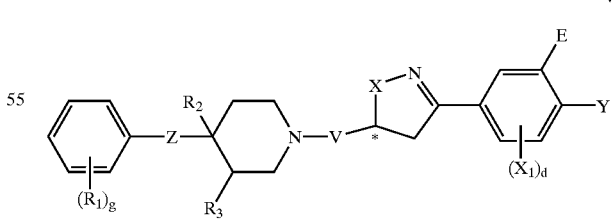

and pharmaceutically acceptable salts thereof wherein $R_1$, g, Z, h, $R_2$, $R_3$, V, $X_1$, d, E, and Y are as defined above for Formula I;

X is O, S, or N—R, wherein R is hydrogen or alkyl; and
* means a chiral center designated R, S, or mixtures thereof.

Preferred is a compound of Formula VI

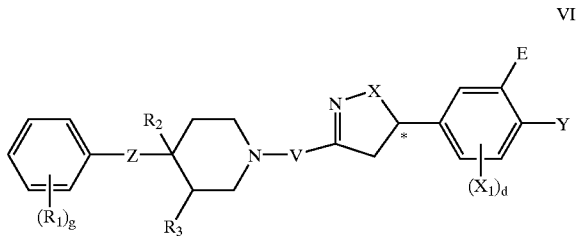

and pharmaceutically acceptable salts thereof wherein $R_1$, g, Z, h, $R_2$, $R_3$, V, $X_1$, d, E, and Y are as defined above for Formula I;
X is O, S, or N—R, wherein R is hydrogen or alkyl; and
* means a chiral center designated R, S, or mixtures thereof.

Preferred is a compound of Formula VII

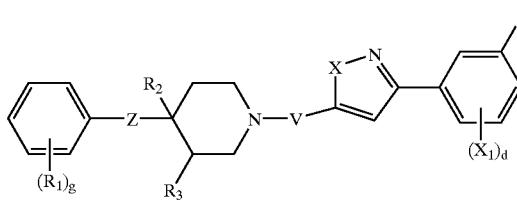

and pharmaceutically acceptable salts thereof wherein $R_1$, g, Z, h, $R_2$, $R_3$, V, $X_1$, d, E, and Y are as defined above for Formula I; and
X is O, S, or N—R, wherein R is hydrogen or alkyl.

Preferred is a compound of Formula VIII

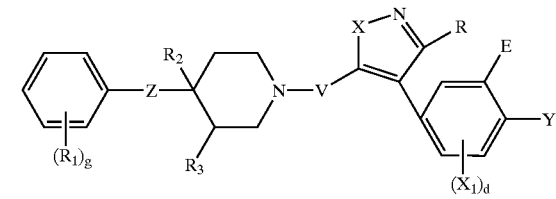

and pharmaceutically acceptable salts thereof wherein $R_1$, g, Z, h, $R_2$, $R_3$, V, $X_1$, d, E, and Y are as defined above for Formula I; and
X is O, S, or N—R, wherein R is independently hydrogen or alkyl.

Preferred is a compound of Formula IX

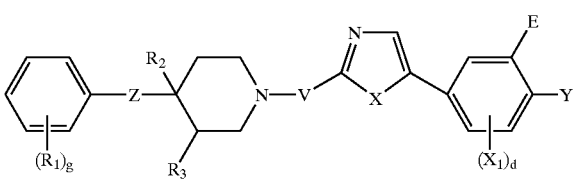

and pharmaceutically acceptable salts thereof wherein $R_1$, g, Z, h, $R_2$, $R_3$, V, $X_1$, d, E, and Y are as defined above for Formula I; and
X is O, S, or N—R, wherein R is hydrogen or alkyl.

Preferred is a compound of Formula X

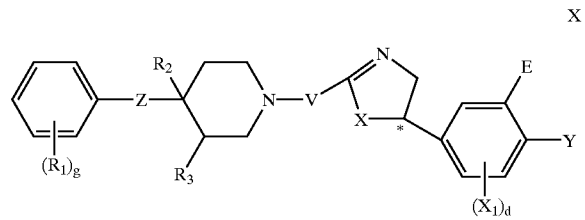

and pharmaceutically acceptable salts thereof wherein $R_1$, g, Z, h, $R_2$, $R_3$, V, $X_1$, d, E, and Y are as defined above for Formula I;
X is O, S, or N—R, wherein R is hydrogen or alkyl; and
* means a chiral center designated R, S, or mixtures thereof.

Preferred is a compound of Formula XI

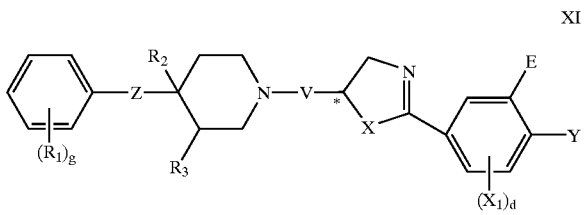

and pharmaceutically acceptable salts thereof wherein $R_1$, g, Z, h, $R_2$, $R_3$, V, $X_1$, d, E, and Y are as defined above for Formula I;
X is O, S, or N—R, wherein R is hydrogen or alkyl; and
* means a chiral center designated R, S, or mixtures thereof.

Preferred is a compound of Formula XII

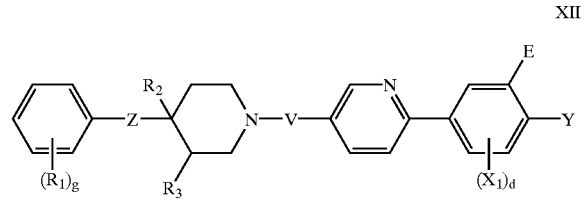

and pharmaceutically acceptable salts thereof wherein $R_1$, g, Z, h, $R_2$, $R_3$, V, $X_1$, d, E, and Y are as defined above for Formula I.

Preferred is a compound of Formula XIII

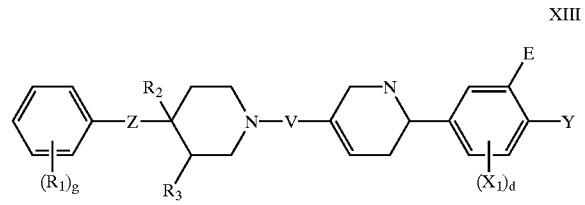

and pharmaceutically acceptable salts thereof wherein $R_1$, g, Z, h, $R_2$, $R_3$, V, $X_1$, d, E, and Y are as defined above for Formula I.

Preferred is a compound of Formula XIV

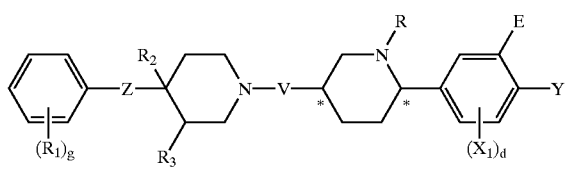

XIV and pharmaceutically acceptable salts thereof wherein $R_1$, g, Z, h, $R_2$, $R_3$, V, $X_1$, d, E, and Y are as defined above for Formula I;
R is hydrogen or alkyl; and
* means a chiral center designated R, S, or mixtures thereof.

Preferred is a compound of Formula XV

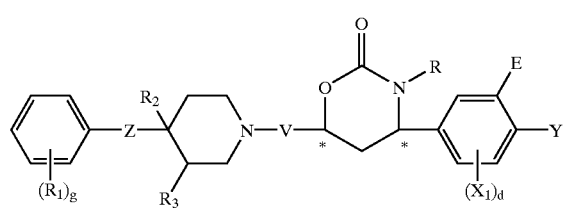

XV and pharmaceutically acceptable salts thereof wherein $R_1$, g, Z, h, $R_2$, $R_3$, V, $X_1$, d, E, and Y are as defined above for Formula I;
R is hydrogen, alkyl, or substituted alkyl; and
* means a chiral center designated R, S, or mixtures thereof.

The invention also provides a pharmaceutical composition comprising a therapeutically effective amount of a compound of Formula I, or a pharmaceutically acceptable salt thereof, together with a diluent, carrier, or excipient.

In a preferred embodiment, the invention provides a pharmaceutical composition comprising a therapeutically effective amount of a compound of Formula II or Formula IV together with a diluent, carrier, or excipient.

In a more preferred embodiment, the invention provides a pharmaceutical composition comprising a therapeutically effective amount of a compound selected from the group consisting of:
(+)-6-{5-[4-(4-Fluorobenzyl)piperidin-1-ylmethyl]-4,5-dihydroisoxazol-3-yl}-3H-benzoxazol-3-one;
(−)-6-{5-[4-(4-Fluorobenzyl)piperidin-1-ylmethyl]-4,5-dihydroisoxazol-3-yl}-3H-benzoxazol-3-one, or
a pharmaceutically acceptable salt thereof., together with a diluent, carrier, or excipient.

The invention also provides a method of treating disorders responsive to the selective blockade of the N-methyl-D-aspartate receptor subtypes in a mammal, including a human, suffering therefrom which comprises administering a compound of Formula I or a pharmaceutically acceptable salt thereof.

In a preferred embodiment, the invention provides a method of treating disorders responsive to the selective blockade of the N-methyl-D-aspartate receptor subtypes in a mammal, including a human, suffering therefrom comprising administering a compound of Formula I or a pharmaceutically acceptable salt thereof, wherein the disorders are selected from stroke, cerebral ischemia, central nervous system disorders, depression, trauma, hypoglycemia, neurodegenerative disorders, anxiety, migraine headache, convulsions, aminoglycoside antibiotics-induced hearing loss, psychosis, glaucoma, CMV retinitis, opioid tolerance or withdrawal, pain, including chronic pain, neuropathic pain, or surgical pain, and urinary incontinence.

In a more preferred embodiment, the invention provides a method of treating disorders responsive to the selective blockade of the N-methyl-D-aspartate receptor subtypes in a mammal, including a human, suffering therefrom comprising administering a compound of Formula I or a pharmaceutically acceptable salt thereof, wherein the disorder is pain.

In another more preferred embodiment, the invention provides a method of treating disorders responsive to the selective blockade of the N-methyl-D-aspartate receptor subtypes in a mammal, including a human, suffering therefrom comprising administering a compound of Formula I or a pharmaceutically acceptable salt thereof, wherein the disorder is Parkinson's disease.

In a still more preferred embodiment, the invention provides a method of treating disorders responsive to the selective blockade of the N-methyl-D-aspartate receptor subtypes in a mammal, including a human, suffering therefrom comprising administering a compound of Formula II or Formula IV.

In a still more preferred embodiment, the invention provides a method of treating disorders responsive to the selective blockade of the N-methyl-D-aspartate receptor subtypes in a mammal, including a human, suffering therefrom comprising administering a compound selected from the group consisting of:
(+)-6-{5-[4-(4-Fluorobenzyl)piperidin-1-ylmethyl]-4,5-dihydroisoxazol-3-yl}-3H-benzoxazol-3-one;
(−)-6-{5-[4-(4-Fluorobenzyl)piperidin-1-ylmethyl]-4,5-dihydroisoxazol-3-yl}-3H-benzoxazol-3-one, or
a pharmaceutically acceptable salt thereof.

In another more preferred embodiment, the invention provides a method of treating disorders responsive to the selective blockade of the N-methyl-D-aspartate receptor subtypes in a mammal, including a human, suffering therefrom comprising administering a compound of Formula I or a pharmaceutically acceptable salt thereof, further comprising administering a dopamine agonist.

In another more preferred embodiment, the invention provides a method of treating disorders responsive to the selective blockade of the N-methyl-D-aspartate receptor subtypes in a mammal, including a human, suffering therefrom comprising administering a compound of Formula I or a pharmaceutically acceptable salt thereof, further comprising administering a dopamine agonist wherein said dopamine agonist is L-DOPA.

In another preferred embodiment, the invention provides a method of treating disorders comprising administering a compound of Formula I or a pharmaceutically acceptable salt thereof in unit dosage form.

Also, the invention provides a compound selected from the group consisting of:
6-(2-Azido-1-hydroxyethyl)-3H-benzoxazol-2-one;
6-[2-Azido-1-(tert-butyldimethylsilanyloxy)ethyl]-3H-benzoxazol-2-one;
6-[2-Amino-1-(tert-butyldimethylsilanyloxy)ethyl]-3H-benzoxazol-2-one;
2-(4-Benzylpiperidin-1-yl)-N-[2-(tert-butyl-dimethylsilanyloxy)-2-(2-oxo-2,3-dihydrobenzoxazol-6-yl)ethyl]acetamide;
2-(4-Benzylpiperidin-1-yl)-N-[2-(tert-butyl-dimethylsilanyloxy)-2-(2-oxo-2,3-dihydrobenzoxazol-6-yl)ethyl]thioacetamide;
2-(4-Benzylpiperidin-1-yl)-N-[2-hydroxy-2-(2-oxo-2,3-dihydrobenzoxazol-6-yl)ethyl]thioacetamide;

1-Chloro-3-[4-(4-fluorobenzyl)piperidin-1-yl]propan-2-ol;
1-Chloro-3-(4-benzylpiperidin-1-yl)propan-2-ol;
2-{3-[4-(4-Fluorobenzyl)piperidin-1-yl]-2-hydroxypropyl}isoindole-1,3-dione;
2-[3-(4-Benzylpiperidin-1-yl)-2-hydroxypropyl]isoindole-1,3-dione;
1-Amino-3-[4-(4-fluorobenzyl)piperidin-1-yl]propan-2-ol bis-hydrochloride salt;
1-Amino-3-[4-benzylpiperidin-1-yl]propan-2-ol bis-hydrochloride salt;
{3-[4-(4-Fluorobenzyl)piperidin-1-yl]-2-hydroxypropyl}carbamic acid benzyl ester;
[3-(4-Benzylpiperidin-1-yl)-2-hydroxypropyl]carbamic acid benzyl ester;
{2-(tert-Butyldimethylsilanyloxy)-3-[4-(4-fluorobenzyl)piperidin-1-yl]propyl}carbamic acid benzyl ester;
{2-(tert-Butyldimethylsilanyloxy)-3-[4-benzylpiperidin-1-yl]propyl}carbamic acid benzyl ester;
{2-(tert-Butyldimethylsilanyloxy)-3-[4-(4-fluorobenzyl)piperidin-1-yl]propylamine;
Methyl 2-oxo-2,3-dihydrobenzoxazole-6-carboxylate;
2-Oxo-2,3-dihydrobenzoxazole-6-carboxylic acid;
2-Oxo-2,3-dihydrobenzoxazole-6-carboxylic acid [3-(4-benzylpiperidin-1-yl)-2-(tert-butyldimethylsilanyloxy)propyl]amide;
2-Oxo-2,3-dihydrobenzoxazole-6-carboxylic acid [3-(4-(4-fluorobenzyl)piperidin-1-yl)-2-(tert-butylimethylsilanyloxy)propyl]amide;
2-Oxo-2,3-dihydrobenzoxazole-6-carbothioic acid [3-(4-benzylpiperidin-1-yl)-2-(tert-butyldimethylsilanyloxy)propyl]amide;
2-Oxo-2,3-dihydrobenzooxazole-6-carbothioic acid [3-(4-benzylpiperidin-1-yl)-2-hydroxypropyl]amide;
6-(2-Azido-1-hydroxyethyl)-3H-benzoxazol-2-one;
6-[2-Azido-1-(tert-butyldimethylsilanyloxy)ethyl]-3H-benzoxazol-2-one;
6-[2-Amino-1-(tert-butyldimethylsilanyloxy)ethyl]-3H-benzoxazol-2-one;
2-(4-Benzylpiperidin-1-yl)-N-[2-(tert-butyldimethylsilanyloxy)-2-(2-oxo-2,3-dihydrobenzoxazol-6-yl)ethyl]acetamide;
2-(4-Benzylpiperidin-1-yl)-N-[2-(tert-butyldimethylsilanyloxy)-2-(2-oxo-2,3-dihydrobenzoxazol-6-yl)ethyl]thioacetamide; and
2-(4-Benzylpiperidin-1-yl)-N-[2-hydroxy-2-(2-oxo-2,3-dihydrobenzoxazol-6-yl)ethyl]thioacetamide.

Also, the invention provides a process for preparing the compound of Formula I and pharmaceutically acceptable salts thereof comprising the steps of:

1) aminating a precursor alkyl halide;
2) cyclizing the product of Step 1;
3) recovering the desired compound of Formula I; and
4) converting, if desired, to a pharmaceutically acceptable salt.

Also, the invention provides a process for preparing the compound of Formula I and pharmaceutically acceptable salts thereof comprising the steps of:

1) halogenating an unsaturated side chain of a precursor to the compound;
2) cyclizing the product of Step. 1;
3) recovering the desired compound of Formula I; and
4) converting, if desired, to a pharmaceutically acceptable salt.

DETAILED DESCRIPTION OF THE INVENTION

As recited above, one aspect of the present invention is a compound of Formula I

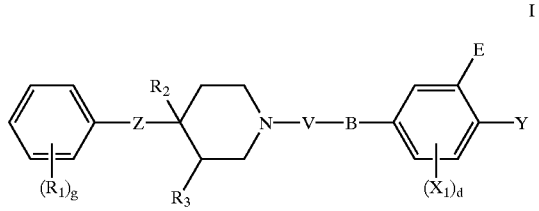

and a pharmaceutically acceptable salt thereof, wherein $R_1$, g, Z, h, $R_2$, $R_3$, V, B, $X_1$, d, E, and Y are as defined above.

All of the references cited herein, including patents, are incorporated herein by reference.

The following definitions apply to terms used in this specification and claims.

The term "patient" means a mammal, including a human.

Preferred patients are humans, cats, and dogs.

The term "$IC_{50}$" means the concentration of test compound required to inhibit activity of a receptor or enzyme by 50%.

The term "L-DOPA" means 3-hydroxy-L-tyrosine.

The term "$(X_1)_d$" wherein d is an integer of from 0 to 2 means the group $X_1$ is present 0 to 2 times on the phenylene to which it is attached. The groups $X_1$ are independently the same or different. Illustrative examples of substituted phenylenes are drawn below.

d is 0:

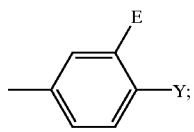

d is 1:

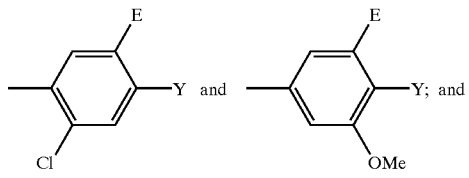

d is 2:

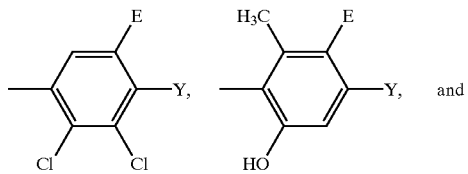

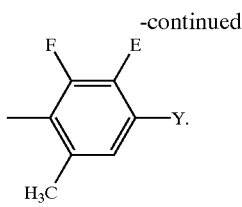

Likewise the term "$(R_1)_g$" wherein g is an integer of from 0 to 3 means the group $R_1$ is present 0 to 3 times on the phenyl to which it is attached. The groups $R_1$ are independently the same or different. Illustrative examples of substituted phenyls are drawn below.

g is 0:

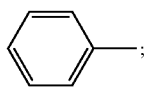

g is 1:

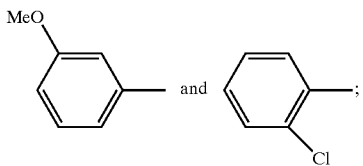

g is 2:

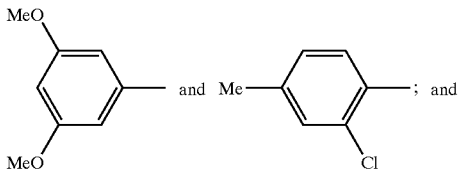

g is 3:

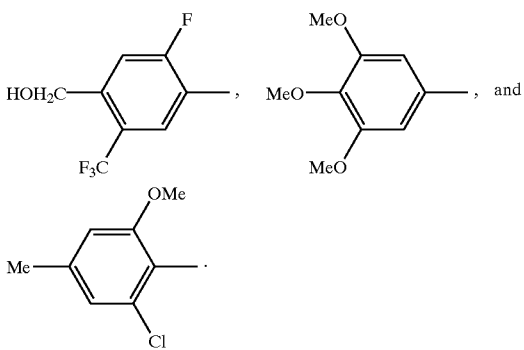

The term "comprising", which is synonymous with the terms "including", "containing", or "characterized by", is inclusive or open-ended and does not exclude additional, unrecited elements or method steps from the scope of the invention that follows.

The phrase "consisting of", is closed-ended and excludes any element, step, or ingredient not specified in the description of the invention that follows.

The phrase "consisting essentially of" limits the scope of the invention that follows to the specified elements or steps and those further elements or steps that do not materially affect the basic and novel characteristics of the invention.

The phrase "filter aid" means a filter medium comprising small particulates. Illustrative examples of filter aids include kieselguhr and CELITE (Celite Corporation, Lompoc, Calif.), a diatomaceous earth filter aid.

The term "alkyl" means a straight or branched, unsubstituted or substituted, hydrocarbon group having from 1 to 12 carbon atoms. Preferred alkyl groups are $C_1$–$C_6$ alkyl. Typical examples of unsubstituted alkyl groups include methyl (i.e., $CH_3$—), ethyl, 1-propyl, and 2-propyl, 1-butyl, 2-butyl, 2-methyl-1-propyl, 1,1-dimethylethyl, 1-pentyl, 2-pentyl, 3-pentyl, 2,2-dimethylpropyl, 1-hexyl, 2-hexyl, 3-hexyl, 4-methyl-1-pentyl, 1-heptyl, 2-heptyl, 3-heptyl, 4-heptyl, 5-methyl-1-hexyl, 1-octyl, 2-octyl, 3-octyl, 4-octyl, 6-methyl-1-heptyl, 5,5-dimethylhexyl, 1-nonyl, 2-nonyl, 1-decyl, 2-decyl, 1-undecyl, 2-undecyl, 1-dodecyl, and 5-dodecyl. Substituted alkyl groups are described below.

The term "alkenyl" means a straight or branched, unsubstituted or substituted, hydrocarbon group having from 2 to 12 carbon atoms and 1 or 2 sites of unsaturation. Preferred groups are $C_2$–$C_6$ alkenyl. Illustrative examples of unsubstituted alkenyl groups include ethenyl [i.e., $CH_2$=C(H)—], 1-propenyl, 2-propenyl, 1-buten-1-yl, 2-buten-1-yl, 1-penten-1-yl, 2-penten-1-yl, 1-penten-3-yl, 1-penten-5-yl, 1-hexen-1-yl, 1-hexen-4-yl, 2-hexen-1-yl, 3-hexen-1-yl, 2-octen-3-yl, 5-nonen-2-yl, 4-undecen-4-yl, and 5-dodecen-2-yl. Substituted alkenyl groups are defined below.

The term "alkoxy" means a straight or branched, substituted or unsubstituted, alkyl group of from 1 to 12 carbon atoms linked through an oxygen atom. Preferred is $C_1$–$C_6$ alkoxy. Illustrative examples of unsubstituted alkoxy groups include methoxy (i.e., $CH_3$—O—), ethoxy, isopropoxy, tert-butoxy, iso-pentoxy, octyloxy, and 7,7-dimethyloctyloxy. Substituted alkoxy groups are defined below.

The term "aryl" means an unsubstituted or substituted aromatic carbocyclic ring having 6 or 10 carbon atoms. Illustrative examples of unsubstituted aryl groups include phenyl (i.e., $C_6H_5$—), 1-naphthyl, and 2-naphthyl. Substituted aryl groups are defined below.

The term "aralkyl" means an unsubstituted or substituted aromatic carbocyclic ring having 6 or 10 carbon atoms (i.e., an aryl group) linked through an alkylene group, wherein alkylene is as defined below. Illustrative examples of unsubstituted aralkyl groups include benzyl, 2-phenylethyl, 3-phenylpropyl, 4-phenylbutyl, 3-methyl-3-phenylpropyl, 1-naphthylmethyl, 1-naphthylethyl, 3-(1-naphthyl)-propyl, 4-(1-naphthyl)-butyl, 4-(2-naphthyl)-butyl, 4-phenylheptyl, and 12-(2-hydroxyphenyl)-dodec-3-yl. Substituted aralkyl groups are defined below.

The term "alkylene" means a straight or branched hydrocarbon chain diradical of from 1 to 12 carbon atoms. Preferred groups are $C_1$–$C_6$ alkylene. Illustrative examples of alkylene groups include methylene (i.e., —$CH_2$—), 1,2-ethylene, 1,2-propylene, 1,3-propylene, 2,2-dimethyl-hexane-1,6-diyl, and dodecan-1,12-diyl.

The term "cycloalkyl" means an unsubstituted or substituted, saturated carbocyclic ring having from 3 to 7 carbon atoms. Illustrative examples of unsubstituted cycloalkyl groups include cyclopentyl, cyclopropyl, cyclohexyl or cycloheptyl. Substituted cycloalkyl is defined below.

As discussed above, the groups alkyl, alkenyl, alkoxy, aryl, aralkyl, and cycloalkyl may be substituted. These substituted groups are respectively termed: "substituted alkyl", "substituted alkenyl", "substituted alkoxy", "substituted aryl", "substituted aralkyl", and "substituted cycloalkyl".

The groups can be substituted with from 1 to 3 substituents independently selected from halogen, OH, O—($C_1$–$C_6$ alkyl), OC(O)—(C₁-C₆ alkyl), —(C₁-C₆ alkylene)-OH, —(C₁-C₆ alkylene)-O—(C₁-C₆ alkyl), NH₂, N(H)—(C₁C₆ alkyl), N—(C₁-C₆ alkyl)₂, NHC(O)—(C₁-C₆ alkyl), —(C₁-C₆ alkylene)-NH₂, —(C₁-C₆ alkylene)-N(H)—(C₁-C₆ alkyl), —(C₁-C₆ alkylene)-N—(C₁-C₆ alkyl)₂, SH, S—(C₁-C₆ alkyl), S—C(O)—(C₁-C₆ alkyl), —(C₁-C₆ alkylene)-SH, —(C₁-C₆ alkylene)-S—(C₁-C₆ alkyl), unsubstituted cycloalkyl, C(O)—(C₁-C₆ alkyl), CO₂H, CO₂—(C₁-C₆ alkyl), C(O)NH₂, C(O)NH—(C₁-C₆ alkyl), and C(O)N—(C₁-C₆ alkyl)₂, wherein (C₁-C₆ alkyl) means a straight or branched hydrocarbon radical having from 1 to 6 carbon atoms, (C₁-C₆ alkylene) means a straight or branched hydrocarbon chain diradical of from 1 to 6 carbon atoms, and unsubstituted cycloalkyl is as defined above. Further, 1 of the 3 substituents in substituted alkyl, substituted alkenyl (on saturated carbons only), substituted alkoxy, substituted aralkyl (on saturated carbon atoms only) and substituted cycloalkyl may be oxo. Examples of these substituted groups are provided below.

Illustrative examples of substituted alkyl groups include HOCH₂, CF₃, (CH₂)₄SCH₃, (CH₂)₈NH₂, C(CH₃)₂CH [CO₂C(CH₃)₃]CH3, CF₂OH, and CH(CO₂H)CH₂CH₂C(O)NMe₂.

Illustrative examples of substituted alkenyl groups include 2-fluoro-ethen-1-yl [i.e., CH(F)=C(H)—], methyl propenoate-2-yl, and 5-iso-butoxy-1-penten-5-yl.

Illustrative examples of substituted alkoxy groups include fluoromethoxy (i.e., FCH₂—O—), 2-ethoxycarbonylethoxy, 4-aminocarbonyl-oxybutyl, and 8-thio-nonyloxy [i.e., CH₃CH(SH)—(CH₂)₇—O—].

Illustrative examples of substituted aryl groups include 2-fluorophenyl, 2,4,6-trimethoxyphenyl, 4-chloro-2-methylphenyl, 5,6-dichloro-naphth-1-yl, and 8-(dimethylaminomethyl)-naphth-2-yl.

Illustrative examples of substituted aralkyl groups include 4-fluorophenylmethyl, 2-(2,4,6-trimethoxyphenyl)-ethyl, 3-(2-carboxyphenyl)-propyl, 4-phenyl-4-hydroxy-butyl, 4-(2-dimethylaminomethyl-naphth-1-yl)-butyl, and 12-(2-hydroxyphenyl)-dodec-3-yl.

Illustrative examples of substituted cycloalkyl groups include 3-methyl-cyclopentyl, 4-hydroxy-cyclohexyl, and 1-methoxy-cycloheptyl.

The term "heteroatom" includes nitrogen, oxygen, and sulfur. When the heteroatom is incorporated in a nonaromatic ring, the heteroatom further includes

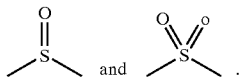

The term "oxo" means =O.

The term "oxo-substituted" means any group which contains a carbon atom that is substituted with an oxo group (i.e., =O). A carbon atom substituted with an oxo group forms a carbonyl group of formula C=O.

The phrase "fused 9- or 10-membered bicyclic ring containing from 0 to 3 heteroatoms" means a group wherein 2 ring systems share 2 and only 2 atoms. Illustrative examples of a fused bicyclic group containing 0 heteroatoms include

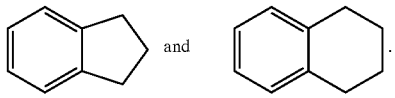

The term "halogen" means bromine, chlorine, fluorine, or iodine.

The term "aminoalkyl" means a H₂N group linked through an alkylene group, wherein alkylene has the meaning as defined above. Illustrative examples of aminoalkyl groups include aminomethyl (i.e., H₂N—CH₂—), 3-aminopropyl, and 1-amino-1,1-dimethylethyl.

The term "alkylaminoalkyl" means an alkyl group, linked through an N(H) group, which in turn is linked through an alkylene group, wherein alkyl and alkylene are as defined above. Illustrative examples of alkylaminoalkyl groups include methylaminomethyl (i.e., CH₃NHCH₂—), 3-(tert-butylamino)-propyl, and 6-(hexylamino)-hexyl.

The term "hydroxyalkyl" means an OH group linked through an alkylene group, wherein alkylene has the meaning defined above. Illustrative examples of hydroxyalkyl groups include hydroxymethyl, 2-hydroxyethyl, and 2-hydroxy-1,1-dimethylethyl.

The term "(aminocarbonyl)-alkyl" means an C(O)NH₂ group linked through an alkylene group, wherein alkylene has the meaning defined above. Illustrative examples of (aminocarbonyl)-alkyl groups include H₂NC(O)—CH₂— and H₂NC(O)—C(CH₃)₃.

The term "(alkylthio)-alkyl-" means an alkyl group linked through a sulfur atom, which in turn is linked through an alkylene group, wherein alkyl and alkylene have the meanings defined above. Illustrative examples of (alkylthio)-alkyl groups include CH₃—S—CH₂—, CH₃CH₂—S—(CH₂)₂—, and CH₃CH(CH₃)CH₂C(CH₃)₂—S—C(CH₃)₂CH₂—.

The term "carboxyalkyl" means a CO₂H group linked through an alkylene group, wherein alkylene has the meaning defined above. Illustrative examples of carboxyalkyl groups include carboxymethyl, 2-carboxyethyl, and 2-carboxy-1,1-dimethylethyl.

The term "amino" means the —NH₂ group.

The term "haloalkyl" means a halogen linked through an alkylene group, wherein halogen and alkylene are as defined above. Illustrative examples of haloalkyl include trifluoromethyl, difluoromethyl, fluoromethyl, and 2,2,2-trichloroethyl.

The term "C(O)-alkyl" means an alkyl group as defined above linked through a carbonyl carbon atom. Illustrative examples of C(O)-alkyl groups include acetyl (i.e., C(O)CH₃), 2,2-dimethylpropionyl, and dodecanoyl.

The term "heterocyclene" means a 4-, 5-, or 6-membered, carbon-linked, unsubstituted or substituted with, for example, alkyl, carboxylic acid, or ester, heterocyclic diradical ring, containing from 1 to 3 heteroatoms which are N, O, or S, selected from the group consisting of:

(i) 1-aza-2-cyclobutanon-3,4-diyl of formula

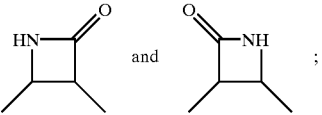

(ii) a 5-membered aromatic, nonaromatic dihydro, or nonaromatic tetrahydro ring having carbon atoms and from 1 to 3 heteroatoms selected from N, O, and S;

(iii) a 5-membered oxo-substituted nonaromatic tetrahydro ring having carbon atoms and 1 or 2 heteroatoms selected from N, O, and S;

(iv) a 6-membered aromatic, nonaromatic tetrahydro, or nonaromatic hexahydro ring having carbon atoms and 1 or 2 heteroatoms, which heteroatoms are nitrogen, and (v) a 6-membered nonaromatic oxo-substituted hexahydro ring having carbon atoms and 1 or 2 heteroatoms which are nitrogen and 0 or 1 heteroatom which is oxygen;

wherein the radical atoms of the heterocyclene are carbon atoms, and further wherein when B is a nonaromatic heterocyclene containing sulfur, said sulfur may further comprise

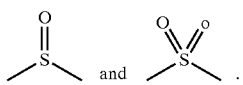

Illustrative examples of 5- and 6-membered heterocyclenes include:
1) A 5-membered heterocyclic ring having one heteroatom such as, for example, the following rings:

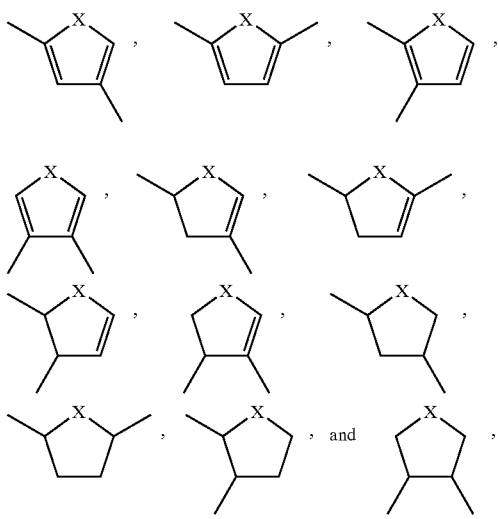

wherein X is O, S, or N—R wherein R is H or alkyl.
2) A 5-membered, substituted or unsubstituted, wherein "substituted" is defined as above, heterocyclic ring having 2 heteroatoms such as, for example, the following rings:

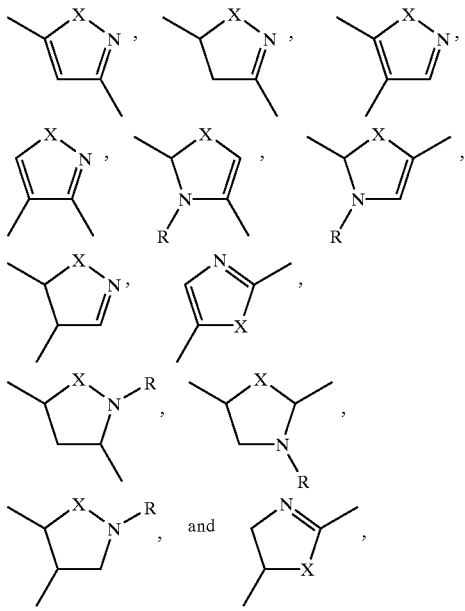

wherein X and R are as defined above.

3) A 5-membered heterocyclic ring having 3 heteroatoms such as, for example, the following rings:

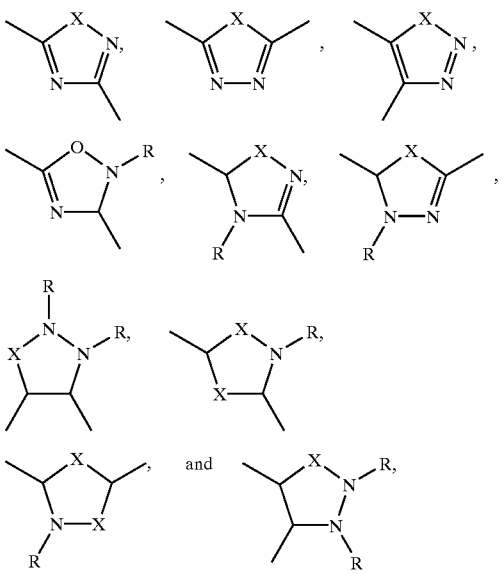

wherein X and R are as defined above.
4) A 6-membered aromatic heterocyclic ring having 1 to 3 nitrogen atoms such as, for example, following rings:

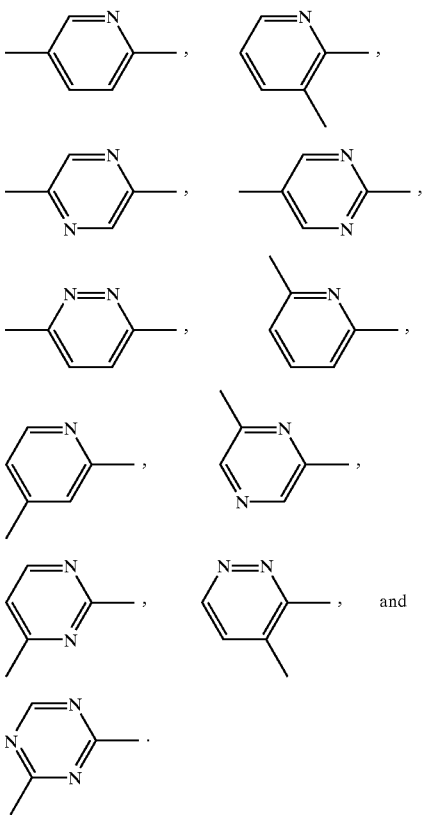

5) A 6-membered nonaromatic tetrahydro heterocyclic ring having 1 or 2 nitrogen atoms such as, for example, the following rings:

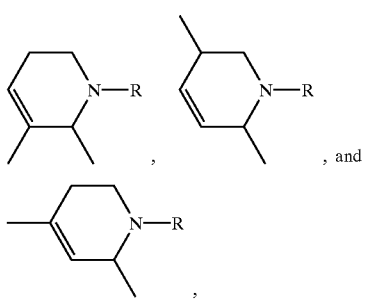

wherein R is independently hydrogen or alkyl;

6) A 6-membered nonaromatic hexahydro heterocyclic ring having 1 or 2 nitrogen atoms such as, for example, the following rings:

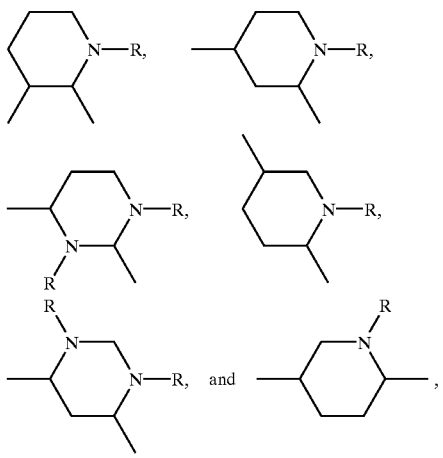

wherein R is independently hydrogen or alkyl;

7) A 5-membered oxo-substituted heterocyclic nonaromatic tetrahydro ring having 1 or 2 heteroatoms O, S, or N—R such as, for example, the following rings:

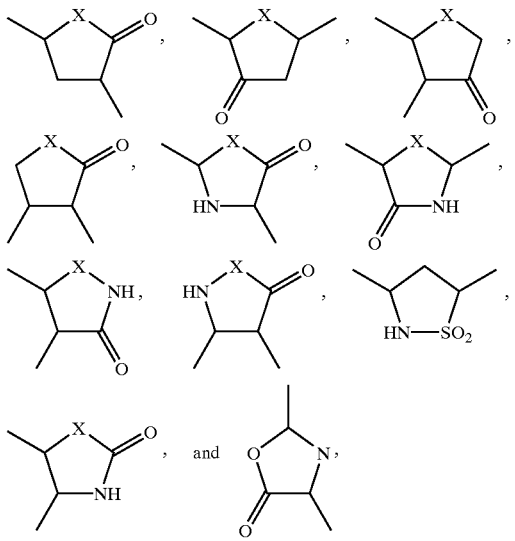

wherein X and R are as defined above.

8) A 6-membered oxo-substituted hexahydro nonaromatic heterocyclic rings having 1 or 2 nitrogen atoms, and 0 or 1 heteroatoms selected from O and S, such as, for example, the following rings:

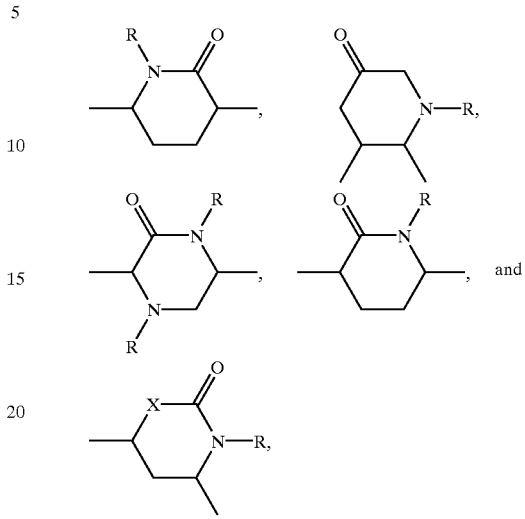

wherein R and X are as defined above.

It is to be appreciated that the above rings do not represent all possible isomers or rings that are described above by the term "heterocyclene".

It is also to be appreciated that the compounds of Formula I may have chiral centers, in which case all stereoisomers thereof, both separately and as racemic and/or diastereoisomeric mixtures, are included.

Some of the compounds of Formula I are capable of further forming nontoxic pharmaceutically acceptable acid-addition and/or base salts. All of these forms are within the scope of the present invention.

For example, pharmaceutically acceptable acid addition salts of the compounds of Formula I include salts derived from inorganic acids such as hydrochloric, nitric, phosphoric, sulfuric, hydrobromic, hydriodic, hydrofluoric, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihyrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science,* 1977;66:1–19.

The acid addition salts of basic invention compounds are prepared by contacting the free base form of the invention compounds with a sufficient amount of the desired acid to produce the salt in the conventional manner.

Pharmaceutically acceptable base salts are formed with metals or amines, such as alkali and alkaline earth metals or organic amines. Examples of metals used as cations are sodium, potassium, magnesium, calcium, and the like.

Examples of suitable amines are N,N-dibenzylethylenediamine, chloroprocaine, choline, diethanolamine, dicyclohexylamine, ethylenediamine, N-methylglucamine, and procaine (see, for example, Berge, supra., 1977).

Base salts of acidic invention compounds are prepared by contacting the free acid form of the invention compounds with a sufficient amount of the desired base to produce a salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the invention may be prepared by a number of methods well known to a person of average skill in the arts of organic and medicinal chemistries.

It should be appreciated that the organic and medicinal chemistry arts provide the skilled artisan with electronically searchable literature, reaction, and reagent databases and a wide variety of commercially available starting materials. For example, see the databases of the Chemical Abstracts service (Columbus, Ohio); Katritzky, Alan R., *Handbook of Heterocyclic Chemistry*, Pergamon Press, Ltd., 1985, Volumes 4 and 5; and The Aldrich Catalog (Sigma-Aldrich Corporation, St. Louis, Mo.).

For examples of the preparation of optically pure $\Delta^2$-isoxazolines (i.e., chiral $\Delta^2$-isoxazolines that consist of only one enantiomer, or substantially one enantiomer), see Yang, K-S, et al., *Tetrahedron Letters*, 2000;41:1453–1456 or Shimizu, M. et al., *Chemistry Letters*, 1996:455–456.

As described above, some of the invention compounds possess chiral centers. It should be appreciated that a person skilled in the medicinal and organic chemistry arts is able to prepare chiral invention compounds by classical resolution techniques and/or asymmetric synthesis.

It should also be appreciated for purposes of synthesizing the compounds of the invention that reactive functional groups present in starting materials, reaction intermediates, or reaction products may be protected during chemical reactions using protecting groups which render the reactive functional groups substantially inert to the reaction conditions (see for example, *Protective Groups in Organic Synthesis*, 2nd ed., Green T W and Wuts P G, John Wiley & Sons, New York, N.Y. 1991). Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), $\beta,\beta,\beta$-trichloroethoxycarbonyl (TCEC), $\beta$-iodoethoxycarbonyl; aryloxycarbonyl groups, such as benzyloxycarbonyl (CBZ), p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl may all be utilized. The protecting group may be removed, after completion of the synthetic reaction of interest, by procedures known to those skilled in the art. For example, a BOC group may be removed by acidolysis, a trityl group by hydrogenolysis, TBDMS by treatment with fluoride ions, and TCEC by treatment with zinc. Use of protecting groups in organic synthesis is well within the skill of the average artisan.

It should be appreciated that reagents, solvents, and starting materials necessary for the preparation of the compounds of the invention may be purchased from a number of commercial sources or may be readily prepared by a number of methods well known to one of average skill in the art of organic chemistry. Further, reactions used to prepare the invention compounds can be carried out under a wide variety of conditions comprising solvents, reagents, catalysts, temperatures, time, atmosphere, and pressure.

Many different methods may be used to prepare the invention compounds. However for purposes of practicing the invention, which comprises compounds, pharmaceutical compositions, and methods of treating certain disorders and diseases, it does not matter how the compounds are made. Nevertheless, novel methods of preparing the invention compounds are valuable as they may afford improvements in ease of synthesis or purification, cost of preparation, or process time. As discussed above, the invention provides novel methods of making the invention compounds.

For example, one method of preparing the compounds of the invention is described below in Scheme 1.

Scheme 1

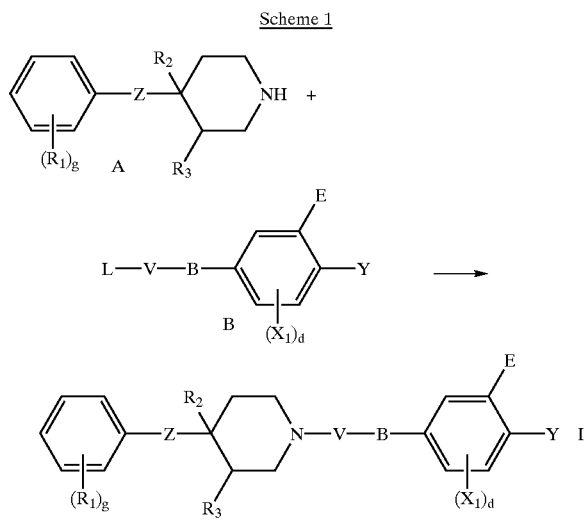

wherein $R_1$, g, Z, h, $R_2$, $R_3$, V, B, $X_1$, d, E, and Y are as defined above and L is a leaving group such that when V is $(CH_2)_n$ or $(CH_2)_m$—C=O, wherein m is not 0, L is, for example, halogen, $CH_3CO_2$—, $CF_3CO_2$—, $CF_3SO_3$—, p-toluyl-$SO_3$—, and the like; and when V is C=O, L is, for example, halogen, hydroxy, which can form intermediates activated for displacement by a compound of formula A by reaction with coupling agents such as, for example, carbonyldiimidazole (CDI), N,N'-dicyclohexylcarbodiimide (DCC), and the like, benzotriazol-1-yl, imidazol-1-yl, $CH_3CO_2$—, and the like.

In Scheme 1, a compound of formula A, wherein $R_1$, g, and $R_2$ are as defined above, is allowed to react with a compound of formula B, wherein L is a leaving group which is displaced by a compound of formula A, to provide a compound of Formula I. In a preferred procedure, a compound of formula A is dissolved or suspended in an aprotic, polar solvent such as, for example, N,N-dimethylformamide (DMF), ethyl acetate, dimethylsulfoxide (DMSO), acetonitrile, nitromethane, acetone, and the like, and optionally a 1 to 2 molar equivalents of a non-nucleophilic base such as, for example, triethylamine, diisopropylethylamine, sodium hydride, and the like is added, followed by addition of a compound of formula B as a neat material (i.e., only the material itself in solid or liquid form) or in a solution of an aprotic, polar solvent such as, for example, the aprotic, polar solvents recited above, at an addition rate that maintains a desired reaction temperature, and the mixture is stirred in air or under an inert atmosphere such as, for example, nitrogen or argon, to give a compound of Formula I. In another preferred procedure, a compound of formula A is dissolved or suspended in an aprotic, nonpolar solvent such as, for example, tetrahydrofuran (THF), diethylether, hexanes, and the like, and about one molar equivalent of a strong base such as, for example, n-butyl lithium, sec-butyl lithium, tert-butyl lithium, potassium hexamethyldisilazide (KHMDS), and the like is added, followed by addition of a compound of formula B as a neat material or in a solution of a nonpolar, aprotic solvent such as, for example, the nonpolar, aprotic solvents recited above, at an addition rate that maintains a desired reaction temperature, and the mixture is stirred to give a compound of Formula I. In still another preferred procedure, a compound of formula B, wherein L—V— is HO—C(O)—, is dissolved or suspended in an aprotic solvent such as, for example, THF, DMF, ethyl acetate, and the like, and about 1 molar equivalent of a coupling agent such as, for example, CDI, DCC, bis(2-oxo-3-oxazolidinyl)phosphinic chloride (BOP—Cl), and the like, followed by addition of a compound of formula A as a neat material or in a solution of an aprotic solvent such as, for example, the aprotic solvents recited above, at an addition rate that maintains a desired reaction temperature, and the mixture is stirred to give a compound of Formula I. In Scheme 1, the preferred molar ratio of a compound of formula A to a compound of formula B is about 1:1.

Another method of preparing the compounds of the invention is described below in Scheme 2.

Scheme 2

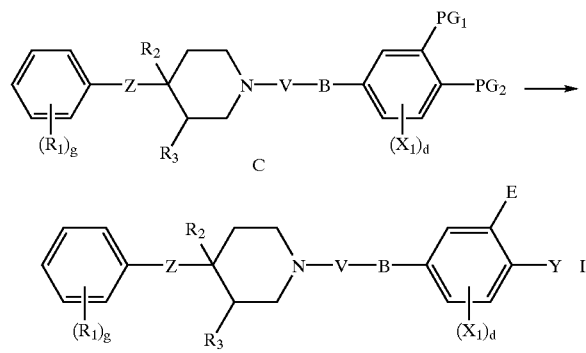

wherein $R_1$, g, Z, h, $R_2$, $R_3$, V, B, $X_1$, d, E, and Y are as defined above, and $PG_1$ and $PG_2$ are protecting groups which may be deprotected to provide the groups E and Y, respectively, of compounds of Formula I. Illustrative examples of $PG_1$ are hydrogen (when E is H), —O-benzyl, —S-benzyl, —NH-benzyl, —NH-(4-methoxybenzyl), —NH—BOC, —NH—CBZ, —O—TBDMS, —CH$_2$-halo, C(O)—CH$_2$-halo, —CO$_2$Me, C(O—CH$_2$)$_2$, CH$_2$CH$_2$CO$_2$Me, and the like. Illustrative examples of $PG_2$ are —NH-benzyl, —NH-(4-methoxybenzyl), —NH—BOC, —NH—CBZ, CO$_2$Me, —O-benzyl, —O—TBDMS, and the like.

In Scheme 2, a compound of formula C is deprotected to give a compound of Formula I. In a preferred procedure, a compound of formula C, wherein $PG_1$ and/or $PG_2$ is —O-benzyl, —S-benzyl, —NH-benzyl, —NH—CBZ, and the like, is dissolved or suspended in a suitable solvent such as, for example, acetic acid, ethanol, THF, dichloromethane, and the like, and allowed to react with a deprotecting reagent such as, for example, a mixture of hydrogen gas and a suitable hydrogenation catalyst such as, for example, palladium on carbon, palladium on barium sulfate, platinum on carbon, sponge nickel, and the like, under pressure, phosphorous tribromide, hydrochloric acid, titanium tetrachloride, and the like, at an addition rate that maintains a desired reaction temperature, to give a compound of Formula I. Examples 1, 3, 4a, 4b, 5, and 9 are representative of the chemistry described in Scheme 2.

Another method of preparing the compounds of the invention is described below in Scheme 3.

Scheme 3

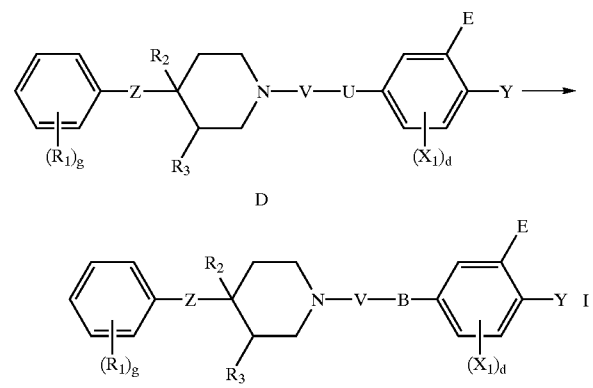

wherein $R_1$, g, Z, h, $R_2$, $R_3$, V, B, $X_1$, d, E, and Y are as defined above, and U is —C(H)=C(H)— or —C≡C—.

In Scheme 3, a compound of formula D is allowed to react with a 3- or 4-membered cyclization reagent to give a compound of Formula I, wherein B is a 5- or 6-membered heterocyclene, respectively. In a preferred procedure, a compound of formula D is dissolved or suspended in an aprotic solvent such as, for example, THF, dichloromethane, acetone, DMF, and the like, and allowed to react with a 3-membered cyclizing reagent such as, for example, an alkylazide, alkyldiazomethane, acetonitrile oxide, prepared by reaction of an aldoxime such as, for example, acetaldoxime [i.e., CH$_3$C(H)=N—OH] with a radical generating agent such as, N-bromosuccinimide (NBS), N-chlorosuccinimde (NCS), and the like, or a 4-membered cyclizing reagent such as, for example, H$_2$C=C(H)—C(H)=N—EDG, wherein EDG is an electron donating group such as, for example, —N(CH$_3$)$_2$, —OMe, and the like, to give a compound of Formula I. Example 2 is representative of the chemistry described in Scheme 3.

Another method of preparing the compounds of the invention is described below in Scheme 4.

Scheme 4

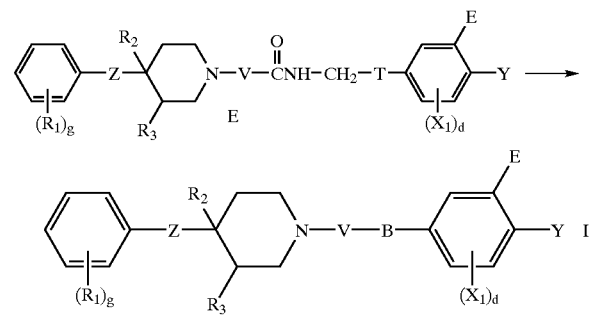

wherein $R_1$, g, Z, h, $R_2$, $R_3$, V, $X_1$, d, E, and Y are as defined above, B is oxazole, dihydrooxazole, thiazole, or dihydrothiazole, and T is C=O or C(H)OH.

In Scheme 4, a compound of formula E is allowed to react with a reagent and/or catalyst under cyclizing conditions to provide a compound of Formula I. In a preferred procedure, a compound of formula D is dissolved in an aprotic solvent such as, for example, THF, ethyl acetate, DMF, DMSO, and the like, and a dehyrdating reagent such as, for example, anhydrous magnesium sulfate, anhydrous calcium chloride, activated 3 angstrom molecular sieves, trimethoxymethane, oxalyl chloride, $PCl_5$, phosphorous pentoxide and the like, is added and optionally an acid catalyst such as, for example, trifluoroacetic acid, para-toluenesulfonic acid, and the like, is added, and the mixture is stirred to provide a compound of Formula I, wherein B is oxazole or dihydrooxazole. In another preferred procedure, a compound of formula D is dissolved in an aprotic solvent such as, for example, THF, ethyl acetate, DMF, DMSO, and the like, and a sulfurating reagent (i.e., a reagent that introduces a sulfur atom) such as, for example, $P_2S_5$, [2,4-bis(4-methoxyphenyl)-1,3-dithian-2,4-diphosphetane-2,4-disulfide] (i.e., Lawesson's reagent), and the like, is added, and the mixture is stirred to provide a compound of Formula I, wherein B is thiazole or dihydrothiazole. Examples 6(a)–6(f) and 8 are representative of the chemistry described in Scheme 4.

Another method of preparing the compounds of the invention is described below in Scheme 5.

Scheme 5

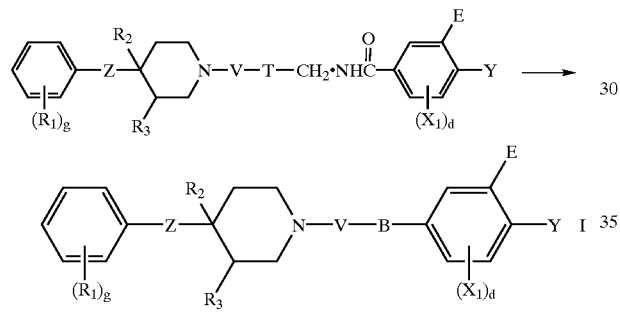

wherein $R_1$, g, Z, h, $R_2$, $R_3$, V, $X_1$, d, E, and Y are as defined above, B is oxazole, dihydrooxazole, thiazole, or dihydrothiazole, and T is C=O or C(H)OH.

In Scheme 5, a compound of Formula F is allowed to react with a reagent and/or catalyst under cyclizing conditions to provide a compound of Formula I. Preferred procedures are as described above in Scheme 4. Examples 7(a) and 7(b) are representative of the chemistry described in Scheme 5.

Another method of preparing the compounds of the invention is described below in Scheme 6.

Scheme 6

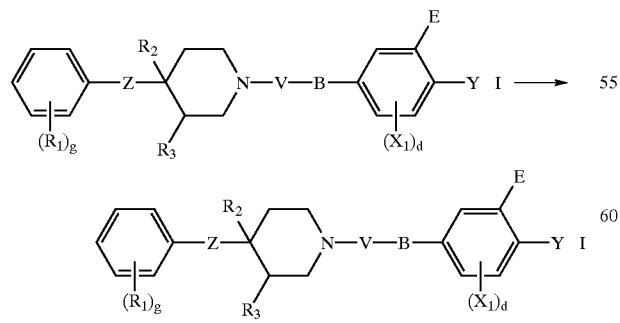

wherein $R_1$, g, Z, h, $R_2$, $R_3$, V, B, $X_1$, d, E, and Y are as defined above.

In Scheme 6, a compound of Formula I is allowed to react with a reagent to provide a different compound of Formula I. In a preferred procedure, a compound of Formula I wherein V is $(CH_2)_mC=O$ is dissolved or suspended in a suitable aprotic, nonpolar solvent such as, for example, THF, methyl-tert-butylether (MTBE), hexanes, and the like, and a reducing agent such as, for example, lithium aluminum hydride, sodium borohydride, sodium triacetoxyborohydride, diisobutylaluminum hydride (DIBAL), and the like, is added at an addition rate that maintains a desired reaction temperature, and the mixture is stirred to give a compound of Formula I wherein V is $(CH_2)_n$.

Another method of preparing the compounds of the invention is described below in Scheme 7.

Scheme 7

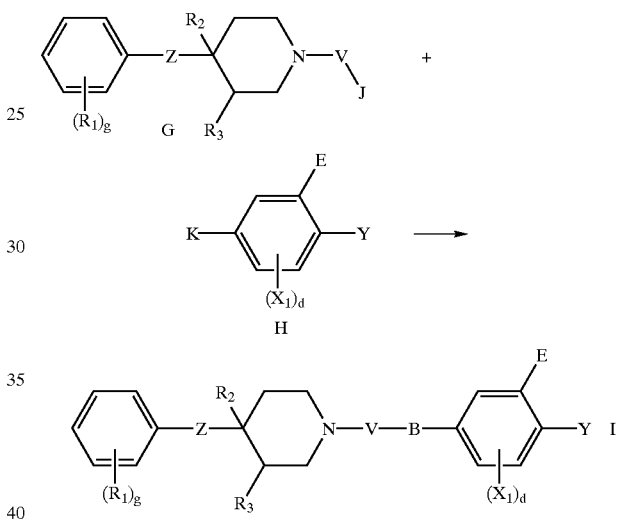

wherein $R_1$, g, Z, h, $R_2$, $R_3$, V, $X_1$, d, E, and Y are as defined above, B is isoxazole, dihydroisoxazole (i.e., isoxazoline), dihydrothiazoline, or oxazole; J is C(H)=$CH_2$ or C≡C—H, and K is C(Cl)=N—OH.

In Scheme 7, a compound of formula G is allowed to react with a compound of formula H under [3+2] cyclization conditions to provide a compound of formula I. In a preferred procedure, a compound of formula G and a compound of formula H are dissolved or suspended in a solvent such as, for example, methanol, ethanol, THF, ethyl acetate, toluene, dichloromethane, and the like, and optionally a nonnucleophilic base such as, for example, triethylamine, diisopropylethylamine, sodium hydride, and the like is added, and the mixture is stirred to provide a compound of Formula I. Examples 10 to 16 are representative of the chemistry described in Scheme 7.

Examples of the preparation of the invention compounds are described below.

EXAMPLE 1

6-[5-(4-Benzylpiperidin-1-ylmethyl)-4,5-dihydroisoxazol-3-yl]-3H-benzoxazol-2-one

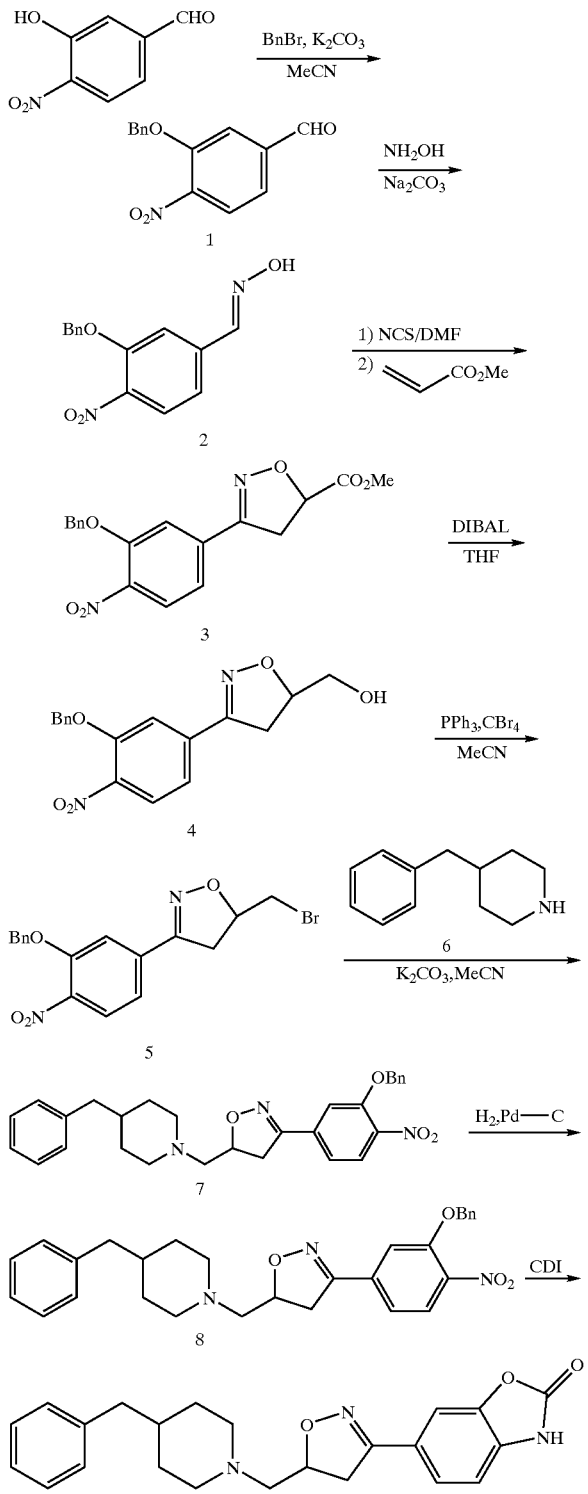

Step 1: A mixture of 3-hydroxy-4-nitrobenzaldehyde (10.0 g, 0.0598 mol), benzyl bromide (7.20 mL, 0.0598 mol) and anhydrous potassium carbonate (18.20 g, 0.1316 mol) in 250 mL MeCN was heated at 60° C. for 5 hours with vigorous stirring. The reaction mixture was filtered, and the filtrate was concentrated. The residue was taken up in chloroform, and an orange precipitate was removed. The filtrate was reconcentrated to an oil which crystallized on standing to give 1 (15.38 g, 100%): TLC Rf=0.58 (1:1 hexanes/EtOAc).

Step 2: To a suspension of compound of formula 1 (3.0 g, 0.0117 mol) in 30 mL isopropanol was added hydroxylamine hydrochloride (812 mg, 0.0117 mol), followed by sodium carbonate (2.47 g, 0.0234 mol). After addition was complete the reaction mixture was vigorously stirred at 40° C. for 30 minutes (all starting material went into solution) and concentrated. The residue was taken up in water, and the aqueous mixture was washed 2× with EtOAc. The organic washings were combined and washed with saturated $NaCl_{(aq)}$, dried over magnesium sulfate and concentrated to a yellow solid which was used without further purification to give 2 (2.63 g, 82%); TLC Rf=0.55 (1:1 hexanes/EtOAc); CI-MS (m/z): 273 $[M+H]^+$.

Step 3: Compound of formula 2 (2.63 g, 9.66 mmol) was dissolved in 30 mL N,N-dimethylformamide (DMF), and N-chlorosuccinimide (NCS, 1.29 g, 9.66 mmol) was added. The reaction mixture was stirred at room temperature under nitrogen for 4 hours and concentrated. The residue was partitioned between water and EtOAc and after thorough mixing the aqueous layer was discarded, and the organic layer was washed with saturated $NaCl_{(aq)}$, dried over magnesium sulfate, filtered and concentrated to an oil. The crude chlorooxime was taken up in 30 mL 1:1 (v/v) water/tetrahydrofuran (THF) and methyl acrylate (1.18 mL, 12.6 mmol) was added, followed by adding sodium bicarbonate (2.46 g, 29.0 mmol). The reaction mixture was stirred at room temperature for 1.5 hours and extracted with EtOAc. The organic extract was dried over magnesium sulfate, filtered, and concentrated. The crude product was purified by flash chromatography (silica gel 60, 230–400 mesh, 3:2 Hexanes/Ethyl acetate) to give 3 (3.19 g, 93%) as a yellow oil: TLC Rf=0.40 (1:1 hexanes/EtOAc); APCI-MS (m/z): 357 $[M+H]^+$.

Step 4: To a solution of compound of formula 3 (3.10 g, 8.70 mmol) in 30 mL anhydrous THF, cooled to 0° C. under nitrogen, is added slowly 26.10 mL (26.10 mmol) 1.0 molar (1.0 M) diisobutylaluminum hydride (DIBAL or DiBAlH) solution in cyclohexane (note: effervescence). After addition was complete, the reaction mixture was stirred at 0° C. for 1 hour and quenched by slow addition of MeOH. The reaction mixture was partitioned between saturated aqueous potassium sodium tartrate and EtOAc and stirred for 30 minutes. The organic layer was removed, and the aqueous layer was extracted with EtOAc. The combined organic layers were dried over magnesium sulfate, filtered and concentrated to a yellow-orange oil which was used without further purification to give 4 (2.76 g, 97%): TLC Rf=0.13 (1:1 hexanes/EtOAc); APCI-MS (m/z): 329 $[M+H]^+$.

Step 5: To a solution of triphenylphosphine (3.42 g, 12.98 mmol) in 30 mL MeCN is added under nitrogen carbon tetrabromide (4.29 g, 12.98 mmol), followed by compound of formula 4 (2.13 g, 6.49 mmol). After stirring at room temperature for 1.5 hours an additional 2.57 g (9.74 mmol) triphenylphosphine and 3.22 g (9.74 mmol) carbon tetrabromide was added, and stirring was continued for 15 minutes. The reaction mixture was concentrated and the crude product was purified by flash chromatography (4:1 Hexanes/Ethyl acetate to 3:2 Hexanes/Ethyl acetate) to give 5 (1.57 g, 62%) as a yellow, crystalline solid: TLC Rf=0.54 (1:1 hexanes/EtOAc); APCI-MS (m/z): 391 and 393 $[M+H]^+$.

Step 6: A mixture of 4-benzylpiperidine (6) (0.56 mL, 3.26 mmol), compound of formula 5 (1.16 g, 2.96 mmol) and anhydrous potassium carbonate (1.35 g, 9.78 mmol) in 30 mL MeCN was heated at reflux for 24 hours. The reaction mixture was concentrated, and the residue was partitioned between water and EtOAc. The organic layer was washed with water, dried over magnesium sulfate, filtered and concentrated. The crude product was flash chromatographed (EtOAc) to give 7 (1.36 g, 95%) as a yellow oil which crystallized on standing: TLC Rf=0.36 (EtOAc); APCI-MS (m/z): 486 [M+H]$^+$; Anal. Calcd for $C_{29}H_{31}N_3O_4$: C, 71.73; H, 6.43; N, 8.65. Found: C, 71.70; H, 6.59; N, 8.41.

Step 7: A mixture of compound of formula 7 (410 mg, 0.84 mmol) and 50 mg 20% Pd on C catalyst in 50 mL 1:1 (v/v) MeOH/THF was hydrogenated for 11 hours under a hydrogen pressure of 47.8 psi. The catalyst was filtered off (CELITE), and the filtrate was concentrated to give 8 as a brown, glassy solid; (307 mg (100%): TLC Rf=0.10 (EtOAc); APCI-MS (m/z): 366 [M+H]$^+$.

Step 8: A mixture of compound of formula 8 (330 mg, 0.90 mmol) and N,N'-carbonyldiimidazole (218 mg, 1.35 mmol) in 10 mL anhydrous THF was refluxed under nitrogen for 1 hour. The reaction mixture was concentrated, and the residue was taken up in EtOAc. The organic layer was washed with water, saturated aqueous NaCl, dried over magnesium sulfate, filtered and concentrated. The crude product was flash chromatographed (3% MeOH in CHCl$_3$ to 5% MeOH in CHCl$_3$) to give 6-[5-(4-benzylpiperidin-1-ylmethyl)-4,5-dihydroisoxazol-3-yl]-3H-benzoxazol-2-one (176 mg, 50%) as an oil which crystallized on standing: (176 mg, 50%): TLC Rf=0.23 (9:1 CHCl$_3$/MeOH); APCI-MS (m/z): 392 [M+H]$^+$; Anal. Calcd for $C_{23}H_{25}N_3O_3$: C, 70.57; H, 6.44; N, 10.73. Found C, 70.04; H, 6.52; N, 10.63.

EXAMPLE 2

6-[5-(4-Benzylpiperidin-1-ylmethyl)-3-methylisoxazol-4-yl]-3H-benzoxazol-2-one

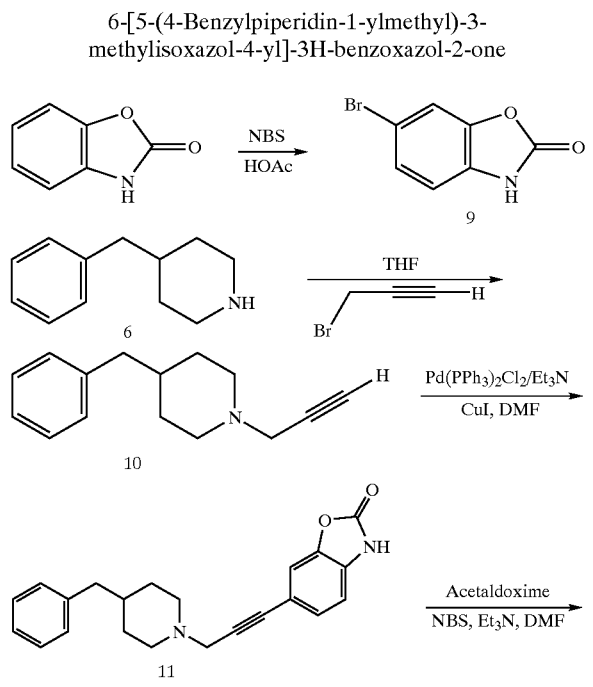

Step 1: To a solution of benzoxazolinone (20 g, 0.148 mol) in 220 mL glacial acetic acid was added N-bromosuccinimide (NBS, 26.36 g, 0.148 mol), and the reaction mixture was stirred at room temperature for 63 hours before pouring into 1500 mL water. The precipitated product was washed thoroughly with water upon collection and recrystallized from EtOH to give 6-bromo-3H-benzoxazol-2-one (9) (25.09 g, 79%): Theory: C, 39.28; H, 1.88; N, 6.54; Br, 37.33. Found: C, 39.36; H, 2.02; N, 6.36; Br, 37.43. MP 192–194° C.

Step 2: A mixture of 4-benzylpiperidine (6) (25 mL, 0.14 mol) and propargyl bromide (10.40 g, 0.07 mol, 80% wt. solution in toluene) in 250 mL anhydrous THF was heated at reflux under nitrogen for 19 hours. The reaction mixture was concentrated, and the residue was taken up in chloroform. The organic layer was washed with 1.0N aqueous NaOH, dried over magnesium sulfate, filtered and concentrated. The crude product was flash chromatographed (1:1 Hexanes/Ethyl acetate to 3:2 Hexanes/Ethyl acetate) to give 10 (11.90 g, 80%), as an orange oil, MS(APCI) M+1=214, TLC (0.34, 1:1 Hexanes/Ethyl acetate; iodine stain).

Step 3: A mixture of compound of formula 10 (7.44 g, 0.0349 mol) and compound of formula 8 (8.19 g, 0.0383 mol) with copper (I) iodide (245 mg, 1.29 mmol), dry triethylamine (14.5 mL, 0.1048 mol), and dichlorobis(triphenylphosphine)palladium(II) (476 mg, 0.68 mmol) in 70 mL anhydrous DMF was heated at 80° C. under nitrogen with vigorous stirring for 18 hours. The reaction mixture was concentrated, and the residue was taken up in acetone and refrigerated for a few hours. The precipitated product was washed with acetone upon collection to give 11 (4.67 g, 39%) as a tan solid, MS(APCI) M+1=347, M−1=345. Melting point (MP) 235–236° C. (dec.), TLC (0.44, EtOAc).

Step 4: To a solution of N-bromosuccinimide (910 mg, 5.11 mmol) in 7.0 mL anhydrous DMF containing 2 drops pyridine was slowly added under nitrogen acetaldoxime (0.32 mL, 5.11 mmol). After addition was complete (5 minutes), the reaction mixture was stirred for 30 minutes at room temperature after which time compound of formula 11 (700 mg, 2.03 mmol) was added in one portion. The reaction mixture was heated to 90° C. and triethylamine (0.70 mL, 5.11 mmol) was added in one portion. Heating was continued for 24 hours, and the reaction mixture was concentrated. The residue was allowed to stand in a small amount of acetone and over a period of time 212 mg of unreacted compound of formula 11 precipitated and was filtered off. The filtrate was concentrated, and the residue was taken up in chloroform. The organic layer was washed with water, dried over magnesium sulfate, filtered and concentrated. The crude product was flash chromatographed (EtOAc) to give 6-[5-(4-benzyl-piperidin-1-ylmethyl)-3-methyl-isoxazol-4-yl]-3H-benzoxazol-2-one as an orange oil which solidified on standing, 100 mg (12%), MS(APCI) M+1=404, M−1= 402. Theory: C, 71.44; H, 6.25; N, 10.41. Found: C, 68.81; H, 6.20; N, 10.07. HPLC (C-18, 1:1 Water/Acetonitrile, isocratic) retention time (RT)=15.34 min (93.8%).

EXAMPLE 3

6-{5-[4-(4-Fluorobenzyl)piperidin-1-ylmethyl]-4,5-dihydroisoxazol-3-yl}-3H-benzoxazol-2-one hydrochloride

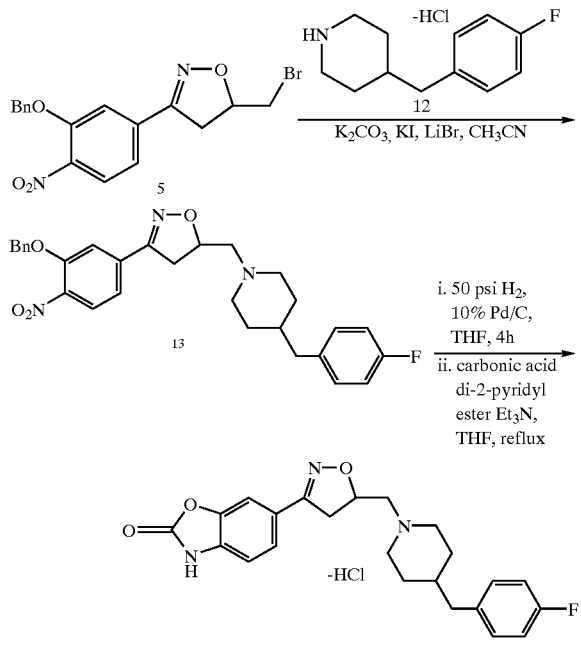

Step 1: To a solution of bromide of formula 5 (2.84 g, 7.26 mmol) and amine of formula 12 (1.67 g, 7.26 mmol) in THF (25 mL) was added $K_2CO_3$ (2.25 g, 16.3 mmol), KI (120 mg, 0.726 mmol), and LiBr (150 mg, 1.72 mmol). The mixture was warmed to 50° C. overnight (ca. 12 hours). After cooling to ambient temperature, the reaction solvent was removed under reduced pressure. The residue was partitioned between water and ethyl acetate. Warming was necessary to form a homogenous organic layer. The organic extract was washed with brine, dried ($Na_2SO_4$), filtered, and concentrated to give amine of formula 13 as a yellow residue. Purification by chromatography (silica, 1:99 to 5:95 MeOH/$CH_2Cl_2$) gave amine of formula 13 (2.36 g, 65%) as a pale yellow solid.

Step 2: To a solution of amine of formula 13 (1.25 g, 2.48 mmol) in THF (80 mL) was added 10% Pd/C (200 mg). The mixture was shaken under 50 pounds per square inch (psi) of $H_2$ for 4 hours then rapidly filtered through CELITE under reduced pressure into a round bottom flask. The flask was capped with a septum and purged with nitrogen. To the clear solution was added carbonic acid di-2-pyridyl ester (590 mg, 2.78 mmol) and $Et_3N$ (800 µL, 5.45 mmol). The solution was refluxed overnight (ca. 12 hours). Although no change in $R_F$ (TLC: 1:9 MeOH/$CH_2Cl_2$, Rf=0.22) was observed, a color change from green to red was observed using ninhydrin that distinguished the starting material from the product. The solvent was removed under reduced pressure to afford a yellow residue. Purification by chromatography (silica gel, 1:99 to 5:95 MeOH/$CH_2Cl_2$) gave a yellow product. The colored product was taken up in MeOH and the solution acidified with 1 M HCl/$Et_2O$. This solution was dripped into 200 mL of $Et_2O$. The resulting suspension was briefly sonicated, and then the solid was collected by filtration to give (±)-6-{5-[4-(4-fluorobenzyl)piperidin-1-ylmethyl]-4,5-dihydroisoxazol-3-yl}-3H-benzoxazol-2-one hydrochloride (728 mg, 66%) as a white solid.

EXAMPLES 4(a) AND 4(b)

4(a): (+)-6-{5-[4-(4-fluorobenzyl)piperidin-1-ylmethyl]-4,5-dihydroisoxazol-3-yl}-3H-benzoxazol-2-one

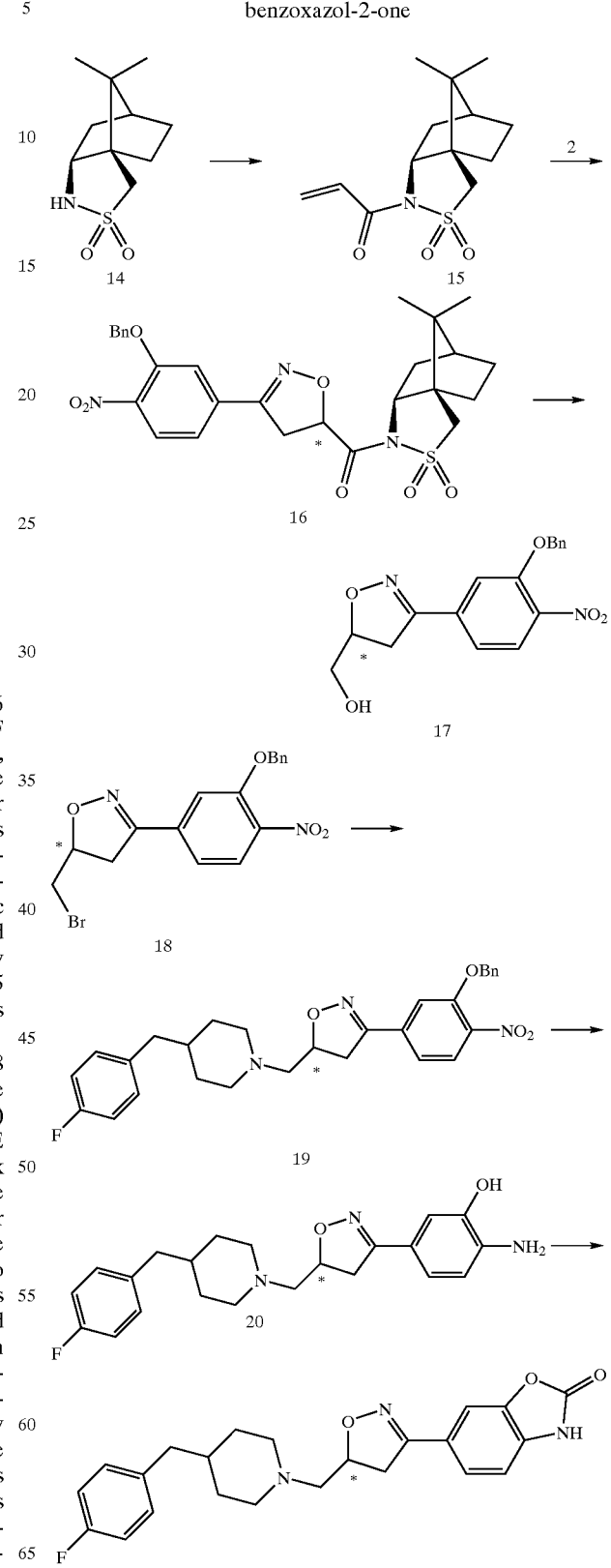

Step 1: Washed (heptane) NaH (1.45 g, 36.3 mmol, 60% in mineral oil) in toluene (150 mL) was treated with the (1R)-sultam 14 (5.20 g, 24.2 mmol) at room temperature under $N_2$. After stirring at room temperature for 1.5 hours, $Cu^ICl$ (239 mg, 2.42 mmol) was added followed by acryloyl chloride (4.38 g, 4.84 mmol, 3.93 mL). After stirring for 3 hours at room temperature, the reaction was quenched with $H_2O$ (1 mL) and the solvents removed. The mixture was taken up in EtOAc and passed through a 'plug' (~20 g) of silica gel, and the EtOAc removed. The product was purified by chromatography ($CH_2Cl_2$) to yield compound 15 as a white solid (3.92 g, 60%).

See *J. Org. Chem.*, 1990;55:4585 for spectral data $R_f(EtOAc/C_7)$–0.62

$R_f(2\% MeOH/CH_2Cl_2)$–0.50.

Step 2: The oxime 15 (3.86 g, 14.20 mmol) and NCS (1.90 g, 14.2 mmol) were stirred in DMF (75 mL) for 3 hours at room temperature. The DMF was removed and the product taken up in EtOAc, washed with brine and dried ($MgSO_4$). After removal of the solvent the material was taken up in THF/$H_2O$ (100:100 mL) and the sultam (IIa, 3.82 g, 14.20 mmol) and $NaHCO_3$ (3.78, 45 mmol) were added. After 1 hour the mixture was diluted with EtOAc, washed with $H_2O$, brine and dried ($MgSO_4$). The crude material obtained was purified by recrystallization (EtOAc) to afford compound 16 as a very pale yellow 'fluffy' crystals (5.17 g, 68% from 3 crops of crystals).

Product from (1R)-sultam $-[\alpha]_D^{23}=+224°$ (c=0.30, MeCN) m/z 540.0 (MH$^+$), $\nu_{max}$ 2761, 1698, 1519, 1338, 1273, 849, 737 cm$^{-1}$, $\delta_H$ 1.00 (3H, s, $CH_3$), 1.22 (3H, s, $CH_3$), 1.40 (2H, m, $CH_2$), 1.92 (3H, m, alkyl), 2.10 (1H, dd, CH, J 8.0, 13.6 Hz), 2.20 (1H, dd, CH, J 3.6, 13.6 Hz), 3.48 (1H, d, CHHSO$_2$, J 14.0 Hz), 3.59 (1H, dd, CHH, J 11.2, 17.2 Hz), 3.59 (1H, d, CHHSO$_2$, J 13.6 Hz), 3.71 (1H, dd, CHN, J 6.8, 17.2 Hz), 5.26 (2H, s, OCH$_2$), 5.76 (1H, dd, CHN, J6.8, 11.2 Hz), 7.18 (1H, dd, aromatic (arom.) J 1.6, 8.4 Hz), 7.32–7.48 (5H, m, Ph), 7.58 (1H, d, arom., J 1.2 Hz), 7.88 (1H, d. arom., J 7.6 Hz).

Step 3: DiBAlH reduction of compound 16 as in Example 1, Step 4; and purification by chromatography (0–70% EtOAc/$C_7$) gave 17 (2.19 g, 71%).

Step 4: Bromination of compound 17 as in Example 1, Step 5 gave 18.

Step 5: Coupling of compound 18 as in Example 1, Step 6 gave 19: $[\alpha]_D^{24}=+57°$ (c=0.42, $CH_2Cl_2$).

Step 6: Reduction of compound 19 as in Example 1, 7 gave 20.

Step 7: Benzoxazol-2-one ring formation of compound 20 as in Example 1, Step 8 gave (+)-6-{5-[4-(4-fluorobenzyl) piperidin-1-ylmethyl]-4,5-dihydroisoxazol-3-yl}-3H-benzoxazol-2-one: $[\alpha]_D^{24}=+102°$ (c=0.31, MeOH).

Example 4(b)

(−)-6-{5-[4-(4-Fluorobenzyl)piperidin-1-ylmethyl]4, 5-dihydroisoxazol-3-yl}-3H-benzoxazol-2-one

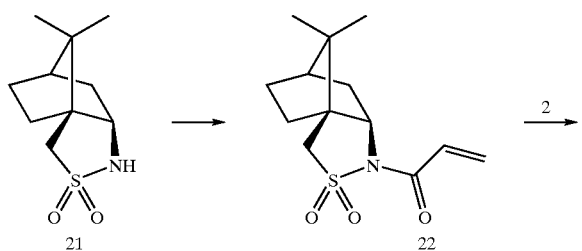

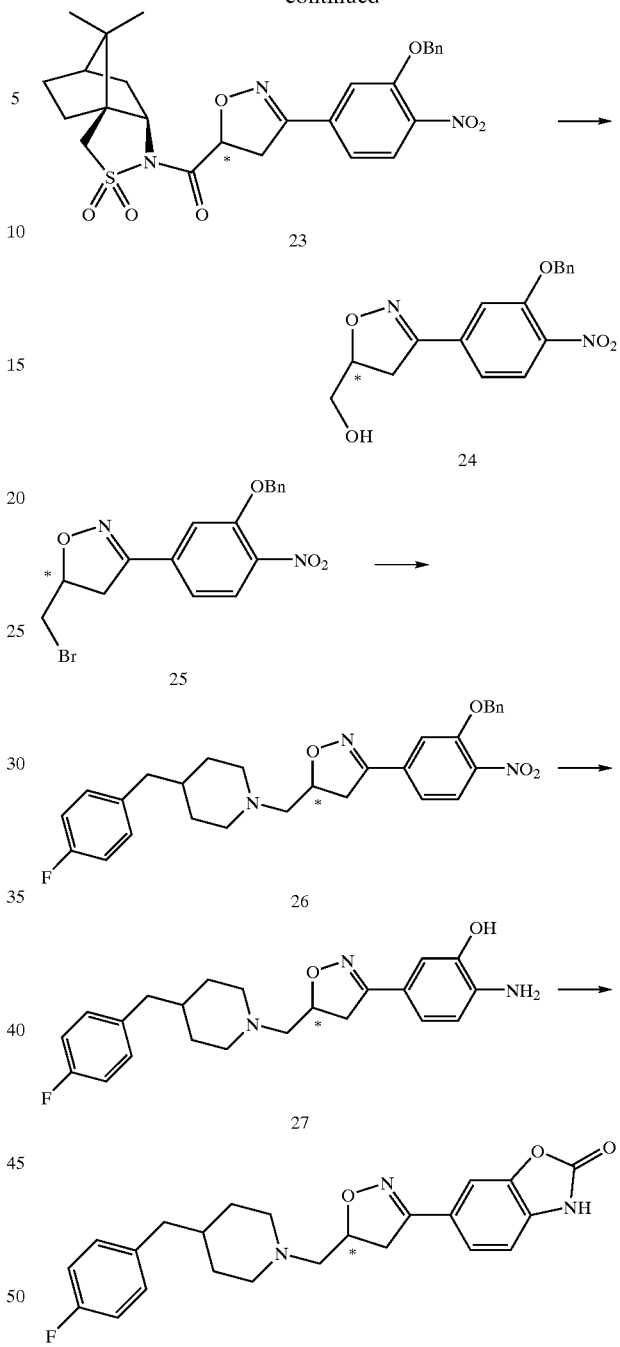

Step 1: Compound 22 was prepared in a manner similar to Example 4a, Step 1, except (1S)-sultam (21) was used in place of the (1R)-sultam.

Step 2: Compound 23 was prepared in a manner similar to Example 4a, Step 2: $[\alpha]_D^{23}=-224°$ (c=0.27, MeCN).

Step 3: DiBAlH reduction of compound 23 as in Example 1, Step 4 gave 24.

Step 4: Bromination of compound 24 as in Example 1, Step 5 gave 25.

Step 5: Coupling of compound 25 as in Example 1, Step 6 gave 26: $[\alpha]_D^{24}=-69°$ (c=0.46, $CH_2Cl_2$).

Step 6: Reduction of compound 26 as in Example 1, Step 7 gave 27.

Step 7: Benzoxazol-2-one ring formation of compound 27 as in Example 1, Step 8 gave (−)-6-{5-[4-(4-fluorobenzyl)piperidin-1-ylmethyl]-4,5-dihydroisoxazol-3-yl}-3H-benzoxazol-2-one: $[\alpha]_D^{23}$=−105° (c=0.44, MeOH).

EXAMPLE 5

6-{3-[4-(4-Fluorobenzyl)piperidin-1-ylmethyl]-4,5-dihydroisoxazol-5-yl}-3H-benzoxazol-2-one

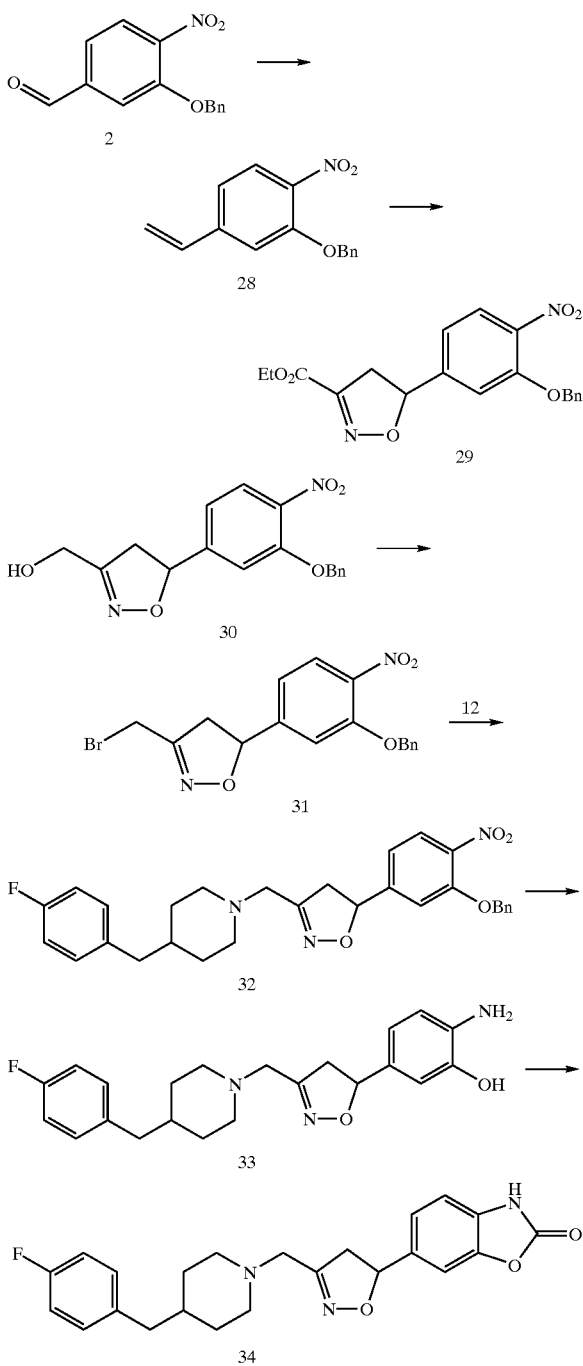

Step 1: Butyllithium (16.0 mL, 40 mmol, 2.5 M in hexanes) was added to a suspension of methyltriphenylphosphonium bromide (12.50 g, 35.0 mmol) in THF (300 mL at 0° C. After stirring for 1 hour, a solution of 2 (7.72 g, 30.04 mmol) was added, and the mixture stirred at room temperature for 3 hours. The solvent was removed, and the crude material was taken up in EtOAc and triturated with heptane, the solids were filtered off (×5). The filtrate was then purified by chromatography (0–10% EtOAc in heptane) to give 28 as a yellow oil (3.04 g, 40%).

m/z 254.09 (M–H⁻)

$\nu_{max}$ 1601, 1585, 1514, 1345 cm$^{-1}$ $\delta_H$ 5.26 (2H, s, CH$_2$O), 5.45 (1H, d, CH=, J 10.4 Hz), 5/82 (1H, d, CH=, J 17.6 Hz), 6.68 (1H, dd, dd, CH=, J 10.8, 17.6 Hz), 7.07 (1H, dd, arom., J 1.6, 8.4 Hz), 7.11 (1H, s, arom.), 7.34 (1H, m, arom.), 7.39 (2H, m, arom.), 7.48 (2H, m, arom.), 7.88 (1H, d, arom., J 8.4 Hz).

Step 2: Compound 28 (1.50 g, 5.88 mmol), ethyl 2-chloro-2-(hydroxyimino)acetate (888 mg, 5.88 mmol), NaHCO$_3$ (988 mg, 11.76 mmol) were stirred at room temperature in THF/H$_2$O (10/5 mL). After 1 hour a further aliquot (888 mg, 5.88 mmol) of ethyl 2-chloro-2-(hydroxyimino)acetate was added, and stirring continued for a further 1 hour. The mixture was then diluted with EtOAc, washed with brine and dried (MgSO$_4$). Purification by chromatography (0–40% EtOAc in heptane) gave 29 as a yellow oil which solidified on standing (1.91 g, 88%).

m/z 371.15 (MH⁺)

$\nu_{max}$ 1722, 1609, 1593, 1519, 1251 cm$^{-1}$ $\delta_H$ 1.39 (3H, t, CH$_3$, J 7.2 Hz), 3.12 (1H, dd, CHH, J 8.0, 18.0 Hz), 3.70 (1H, dd, CHH, J 12.0, 17.6 Hz), 4.37 (2H, q, CH$_2$, J 7.2 Hz), 5.25 (2H, s, CH$_2$O), 5.80 (1H, dd, CH, J 8.0, 11.6 Hz), 6.94 (1H, dd, arom., J 1.2, 8.0 Hz), 7.12 (1H, s, arom.), 7.32–7.47 (5H, m, Ph), 7.88 (1H, d, arom., J 8.0 Hz).

Step 3: DiBAlH (12.90 mL, 12.90 mmol, 1 M in THF) was added to a solution of 29 (1.91 g, 5.16 mmol) in THF (50 mL) at 0° C. After 1 hour a further aliquot of DiBAlH (6.50 mL, 6.50 mmol, 1 M in THF) was added and the mixture stirred for another 1 hour. MeOH (1 mL) was added followed by saturated NaHCO$_3$ (20 mL) and the mixture stirred for 20 minutes. The solids were filtered off and the filtrate taken up in EtOAc, washed with brine and dried (MgSO$_4$). The material was purified by chromatography (0–50% EtOAc in heptane) to give 30 as a straw colored oil (66 mg, 39%).

m/z 329.21 (MH⁺)

$\nu_{max}$ 3390, 1609, 1519, 1352 cm$^{-1}$ $\delta_H$ 1.84 (1H, t, OH, 6.0 Hz), 2.93 (1H, dd, CHH, J 7.2, 17.2 Hz), 3.54 (1H, dd, CHH, J 11.2, 17.2 Hz), 4.43 (2H, d, CH$_2$OH, J 6.0 Hz), 5.26 (2H, d, CH$_2$O, J 3.6 Hz), 5.65 (1H, dd, CH, J 7.2, 11.2 Hz), 6.93 (1H, dd, arom., J 1.2, 8.0 Hz), 7.15 (1H, d, arom., J 1.2 Hz), 7.32–7.48 (5H, m, Ph), 7.86 (1H, d, arom., J 8.0 Hz).

Step 4: Triphenylphosphine (799 mg, 3.05 mmol) and carbontetrabromide (1.01 g, 3.05 mmol) were added to a solution of 30 (667 mg, 2.03 mmol) in MeCN (20 mL) and the resulting mixture stirred at room temperature for 2 hours. The solvent was removed and the crude material purified by chromatography (0–50% EtOAc in heptane) to 31 as a yellow oil (719 mg, 90%).

m/z 393.11/391.11 (MH⁺)

$\nu_{max}$ 1608, 1519, 1350 cm$^{-1}$ $\delta_H$ 3.00 (1H, dd, CHH, J 7.2, 17.2 Hz), 3.60 (1H, dd, CHH, J 11.2, 17.2 Hz), 4.18 (2H, s, CH$_2$Br), 5.25 (2H, s, CH$_2$O), 5.68 (1H, dd, CH, J 7.6, 11.2 Hz), 6.94 (1H, d, arom., J 8.4 Hz), 7.13 (1H, s, arom.), 7.32–7.47 (5H, m, Ph), 7.87 (1H, d, arom., J 8.0 Hz).

Step 5: Compound 31 (7.15 mg, 1.83 mmol), 4-(4-fluorobenzyl)piperidine hydrochloride (12) (504 mg, 2.19 mmol) and anhydrous K$_2$CO$_3$ (507 mg, 3.66 mmol) in MeCN (10 mL) were stirred and heated to reflux for 16 hours. The solution was then diluted with EtOAc, washed with brine and dried (MgSO$_4$). The product was purified by chromatography (0–70% EtOAc in heptane) to yield 32 as a yellow oil (662 mg, 72%).

m/z 504.26 (MH$^+$)

$v_{max}$ 2902, 1608, 1509, 850 cm$^{-1}$ $\delta_H$ 1.89 (2H, m, alkyl), 1.45 (1H, m, alkyl), 1.60 (2H, m, alkyl), 1.97 (2H, m, alkyl), 2.47 (2H, d, ArCH$_2$, J 7.2 Hz), 2.67 (1H, d, CH, J 11.2 Hz), 2.80 (1H, d, CH, J 10.8 Hz), 2.90 (1H, dd, CHH, J 7.2, 17.2 Hz), 3.21 (2H, dd, CH$_2$N, J 14.0, 22.0 Hz), 3.49 (1H, dd, CHH, J 11.2, 17.2 Hz), 5.22 (2H, dd, CH$_2$O, J 12.0, 16.0 Hz), 5.59 (1H, dd, CH, J 7.2, 11.2 Hz), 6.95 (3H, m, arom.), 7.06 (2H, m, arom.), 7.15 (1H, S, arom.), 7.31–7.47 (5H, m, Ph), 7.86 (1H, d, arom., J 8.0 Hz).

Step 6: Compound 32 (595 mg, 1.38 mmol) and Pd—C (10%, 150 mg) in MeOH (100 mL) were (in two batches) subjected to hydrogenation at 50 psi and 30° C. for 1 hour. The catalyst was removed by filtration through a 'filter aid' and yielded 33 as an orange colored glass upon removal of the solvent (490 mg, 90%).

m/z 383.18 (MH$^+$)

$v_{max}$ 3370, 2923, 1509, 1219 cm$^{-1}$ $\delta_H$ 1.25 (2H, bm, alkyl), 1.60 (4H, m, alkyl, NH$_2$), 1.98 (1H, m, alkyl), 2.48 (2H, d, ArCH$_2$, J 6.8 Hz), 2.83 (2H, m, alkyl), 2.94 (1H, dd, CHH, J 8.8, 17.6 Hz), 3.23 (2H, s, CH$_2$N), 3.32 (1H, dd, CHH, J 10.8, 17.2 Hz), 3.67 (1H, bs, OH), 5.42 (1H, dd, CH, J 8.8, 10.8 Hz), 6.70 (2H, s, arom.), 6.73 (1H, s, arom.), 6.96 (1H, s, arom.), 7.06 (2H, m, arom.).

Step 7: Compound 33 (490 mg, 1.28 mmol) and carbonyldiimidazole (CDI) (311 mg, 1.92 mmol) in THF (20 mL) were heated to reflux for 1 hour. The mixture was diluted with EtOAc, washed with brine and dried (MgSO$_4$). The compound was purified by chromatography (0–4% MeOH in CH$_2$Cl$_2$) and repeated (0–100% EtOAc in heptane) to yield 6-{3-[4-(4-fluorobenzyl)piperidin-1-ylmethyl]-4,5-dihydroisoxazol-5-yl}-3H-benzoxazol-2-one as a yellow foam (220 mg, 42%).

m/z 410.20 (MH$^+$)

$v_{max}$ 1776, 1509, 1219 cm$^{-1}$ $\delta_H$ 1.26 (2H, bm, alkyl), 1.43–1.65 (3H, m, alkyl), 1.98 (1H, m, alkyl), 2.48 (2H, d, ArCH$_2$, J 7.2 Hz), 2.75 (1H, d, CHH, J 11.6 Hz), 2.84 (1H, dd, CHH, J 10.8 Hz), 2.96 (1H, dd, CHH, J 8.0, 17.6 Hz), 3.23 (2H, s, CH$_2$N), 3.24 (2H, s, CH$_2$N), 3.44 (1H, dd, CHH, J 10.8, 17.2 Hz), 5.58 (1H, dd, CH, J 8.0, 10.8 Hz), 6.93–7.16 (6H, m, arom.), 7.20 (1H, s, arom.), 7.99 (1H, bs, NH).

EXAMPLE 6

6-{2-[4-(4-Fluorobenzyl)piperidin-1-ylmethyl]thiazol-5-yl}-3H-benzoxazol-2-one

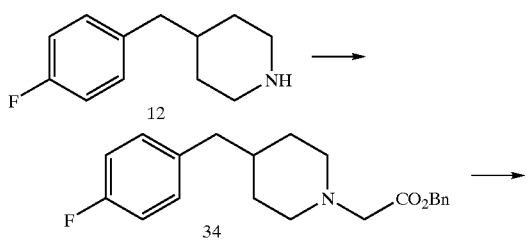

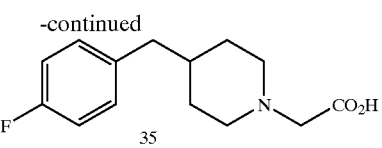

Step 1: To a stirring solution of 4-(4-fluorobenzyl)piperidine (12) (10.0 g, 51.744 mmol) in dichloromethane (10 mL) at 0° C. was added triethylamine (7.21 mL, 51.744 mmol), followed by benzyl-2-bromoacetate (8.20 mL, 51.744 mmol). The resulting solution was allowed to warm to room temperature stirring for 20 hours, then heated to 30° C. for a further 6.5 hours. The reaction mixture was evaporated to dryness in vacuo to give a yellow gum. This was adsorbed onto silica gel, and subjected to column chromatography [EtOAc/Heptane (1:10)] to give 34 (5.07 g, 29%) as a colorless oil:

m/z (APCI+) 342 (MH$^+$, 100%), $\delta_H$ 1.36 (2H, t, J 6.8), 1.25 (2H, t, J 3.6 Hz), 1.36 (2H, dt, J 3.6 Hz), 1.50 (1H, m), 1.60 (2H, d, J 12.4 Hz), 2.10 (2H, dt, J 2.4, 12 Hz), 2.49 (2H, d, J 6.8 Hz), 2.89 (2H, d, J 11.2 Hz), 3.20 (2H, s, N—CH$_2$—CO), 5.14 (2H, s, OCH$_2$Ph), 6.94 (2H, t, J 8.4 Hz), 7.05 (2H, dt, J 2 and 5.2 Hz), 7.32–7.35 (5H, m).

HPLC R$_t$=1.73 min; 69.5%; (5–100% MeCN in H$_2$O (both +0.1% trifluoroacetic acid) over 2.5 minutes at 3 mL/min, held at 100% MeCN for 0.5 minute; Prodigy ODS III 5μ, 50×4.6 mm).

Step 2: To a solution of 34 (5.07 g, 14.85 mmol) in methanol (60 mL) was added 5% palladium on activated carbon (2.50 g, 50% by wgt.) and hydrogenated at 48 psi/25° C. for 15 hours. The reaction mixture was then filtered through CELITE, the catalyst washed with methanol (3×25 mL) and the filtrate condensed to dryness in vacuo to give a pale yellow solid. The solid was subject to column chromatography [MeOH/DCM (1:9)] to give 35 (1.70, 46.6%) as a colorless solid:

m/z (APCI+) 252 (MH$^+$, 100%) and 266 ([M+MeOH]+, 50%), m/z (APCI−) 250 ([M−H]$^-$, 100%).

$v_{max}$ (KBr) 1608 (C=O), 1502s, 1379s cm$^{-1}$ $\delta_H$ 1.71 (1H, m), 1.78 (2H, m), 2.58 (2H, d, J 6.4 Hz), 2.72 (2H, m), 3.48 (2H, d, J 4.8 Hz), 3.68 (2H, d, J 12.0 Hz), 4.1 (1H, s, OH), 6.95 (2H , t, J 8.6 Hz), 7.07 (2H, dt, J 2.0, 5.6 Hz), HPLC R$_t$=1.36 min; 100%; (5–100% MeCN in H$_2$O (both +0.1% trifluoroacetic acid) over 2.5 minutes at 3 mL/minute, held at 100% MeCN for 0.5 minute; Prodigy ODS III 5μ, 50×4.6 mm).

Step 3: To a stirred slurry of aluminum trichloride (49.34 g, 370.05 mmol) in 1,2-dichloroethane (150 mL) at 0° C. under nitrogen was added chloroacetyl chloride (33.43 g, 23.58 mL, 296.04 mmol) dropwise over 30 minutes. After 1 hour, a suspension of 2-benzoxalinone (36) (20.0 g, 148.02 mmol) in 1,2-dichloroethane (50 mL) was added over 30 minutes. The resulting suspension was stirred at 0° C. for 2.5 hours, then heated to 50° C. for 20 hours. The mixture was then poured onto crushed ice, stirred for 30 minutes, and the resulting mixture filtered. The residue was dried in vacuo at 60° C. for 3 -days to give 37 as a pale brown solid (13.70 g, 43%).

$\delta_H$ (d$_6$-Me$_2$SO) 5.16 (2H, s, CH$_2$Cl), 7.23 (1H, d, arom., J 8.0 Hz) 7.84 (1H, dd, arom., J 1.5, 8.0 Hz) 7.88 (1H, s, arom.)

HPLC retention time (R$_t$=1.53 min; 79.71%; (5–100% MeCN in H$_2$O (both +0.1% trifluoroacetic acid) over 2.5 minutes at 3 mL/minute, held at 100% MeCN for 0.5 minute; Prodigy ODS III 5μ, 50×4.6 mm.

Step 4: To a stirred solution of 37 (6.00 g, 28.4 mmol) in DMF (60 mL) was added sodium azide (1.85 g, 28.5 mmol). After 3 hours, the DMF was removed under reduced pressure to give a solid which was washed well with water, filtered and dried to yield 38 as a brown solid (4.5 g, 73%).

m/z 217.09 (M−H$^-$)

$v_{max}$ 3405, 2921, 2135, 1770, 1660, 1606, 1442, 1268, 1240, 1190, 920 cm$^{-1}$ $\delta_H$ (DMSO) 4.86 (2H, s, CH$_2$), 7.22 (1H, d, arom., J 8.1 Hz), 7.79–7.82 (1H, m, arom.), 7.83 (1H, s, arom.) NH not seen.

Step 5: A solution of 38 (100 mg, 0.46 mmol) and Pd—C (5%, 15 mg) in methanol (20 mL) and concentrated HCl (6 drops) was subjected to hydrogenation at 10 psi and 25° C. for 25 minutes. The catalyst was removed by filtration through a 'filter aid' and the solvent removed to give 39 (85 mg, 81%) as a pale brown solid.

m/z 192.97 (MH$^+$)

$v_{max}$ 3374, 2967, 1767, 1695, 1623, 1495, 1419, 1268, 1149 cm$^{-1}$ $\delta_H$ (DMSO) 4.56 (2H, s, CH$_2$), 7.27 (1H, d, arom., J 8.3 Hz), 7.89 (1H, d, arom., J 8.1 Hz), 7.93 (1H, s, arom.), 8.34 (3H, s, NH$_3^+$), 12.34 (1H, s, NH).

Step 6: To a stirring solution of 35 (2.43 g, 9.68 mmol) in dimethylformamide (50 mL) was added N,N-diisopropylethylamine (DIPEA) (3.37 g, 19.36 mmol) followed by O-benzotriazol-1-yl-N,N,N',N'-tetramethyluronium hexafluorophosphate (HBTU) (3.67 g, 9.68 mmol). After 45 minutes, 39 (1.86 g, 9.68 mmol) was added, and the resulting solution stirred at room temperature for 3 hours. The reaction mixture was condensed to dryness in vacuo, redissolved in EtOAc, and washed with saturated aqueous sodium bicarbonate solution. A precipitate formed in the partition, this was filtered and dried. The organic phase was then was then dried with magnesium sulfate and condensed to dryness in vacuo. The resulting brown oil and the filtered solid were combined, adsorbed onto silica gel, and subject to column chromatography [MeOH/DCM (0–5% MeOH over 60 minutes)] to give 40 (0.493 g, 12%) as a tan solid:

$v_{max}$ (KBr) 3401w, 3079w, 1777s, 1675w, 1621s, 1510m, 1451m, 1270s, 947m, 844s.

NMR $\delta_H$ (DMSO-d$_6$) 1.45 (2H, dd, J 11.2 Hz), 1.70 (3H, m), 2.53 (2H, d, J 5.5 Hz) 2.94 (2H, m), 3.37 (4H, m), 3.93 (2H, s), 4.41 (4H, s), 4.73 (2H, d, J 5.6 Hz), 7.12–7.17 (2H, t, arom., J 8.8 Hz), 7.21 (3H, m, arom.), 7.87–7.97 (2H, m, arom.), 8.85 (1H, brs, amide NH), m/z (APCI+) 426 (MH$^+$, 100%), 251 (Acid$^+$, 25%) m/z (APCI−) 424 ([M−H]$^-$, 100%).

Step 7: Purified by preparative HPLC (10–100% ACN (0.1% TFA) over 30 minutes, held at 100% for 5 minutes at 20 mL/min, YMC-PACK ODS-A, 5 micron, 100×30 mm, 254 nm) to give 6-{2-[4-(4-fluorobenzyl)piperidin-1-ylmethyl]thiazol-5-yl}-3H-benzoxazol-2-one (0.031 g, 6%) as a yellow solid:

$v_{max}$ (KBr) 3420br, 3124br, 2921ms, 1613w, 1511w, 1466s (C(S)NH), 1333ms (NC(S)N), 1190s, 807ws, m/z (APCI+) 421 (MH$^+$, 100%), 248 (10%)

m/z (APCI−) 419 ([M−H]$^-$, 100%), 246 (10%),

NMR $\delta_H$ (DMSO-d$_6$) 1.23 (2H, m), 1.51 (1H, m), 1.54 (2H, d, J 12.2 Hz), 2.04 (2H, t, J 11.0 Hz), 2.88 (2H, d, J 11.2 Hz), 3.26 (2H, d, J 10.0 Hz), 3.75 (2H, s) 7.15 (4H, d, arom., J 8.0 Hz), 7.25 (3H, t, arom., J 8.3 Hz), 7.40 (1H, d, arom., J8.3 Hz), 8.0 (1H, s, arom.)

HPLC R$_t$=5.94 minutes, 97.48% (20% to 100% ACN (0.1% TFA) in 20 minutes, held at 100% ACN for 1 minute at 1.5 mL/min, 40° C. liquid chromatography-mass spectrometry (LC-MS) Prodigy ODS(3), 3 micron, 150×4.6 mm 250 nm.

EXAMPLE 7

6-{2-[4-(4-Fluorobenzyl)piperidin-1-ylmethyl]thiazol-5-yl}-3H-benzothiazol-2-one

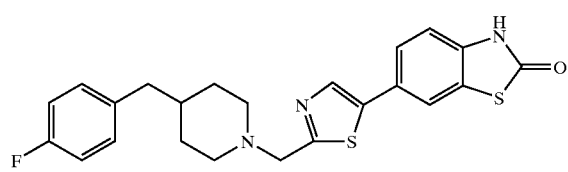

Step 1: Treatment of 2-hydroxybenxothiazole with chloroacetyl chloride and aluminum trichloride, following the procedure described in Example 6, Step 3, gave 6-(2-chloroethanoyl)-3H-benzothiazol-2-one: $\delta_H$ (d$_6$-Me$_2$SO)

5.14 (2H, s, CH₂Cl), 7.23 (1H, d, arom., J 8.5 Hz), 7.92 (1H, dd, arom., J 9.0, 2.0 Hz), 8.27 (1H, d, arom., J 1.5 Hz) and 12.34 (1H, s, NH):

m/z (APCI−) 228 and 226 (each [M-H]⁻, 25 and 55%).

Step 2: Treatment of 6-(2-chloroethanoyl)-3H-benzothiazol-2-one with sodium azide, following the procedure described in Example 6, Step 4, gave 6-(2-azidoethanoyl)-3H-benzothiazol-2-one (6.95 g, 96%):

m/z 233.08 (M-H⁻)

$v_{max}$ 3441, 2117, 1676, 1595, 1399, 1343, 1269, 1214, 1067 cm⁻¹

$\delta_H$ (DMSO) 4.84 (2H, s, CH₂), 7.23 (1H, d, arom., J 8.3 Hz), 7.85–7.88 (1H, m, arom.), 8.20 (1H, s, arom.), NH not seen; and Step 3: 6-(2-Azidoethanoyl)-3H-benzothiazol-2-one (0.5 g, 2.14 mmol) and Pd—C (5%, 0.17 g) in methanol (40 mL) and concentrated HCl (0.5 mL) were subjected to hydrogenation at 20 psi and 25° C. for 1 hour. The catalyst was removed by filtration through a 'filter aid' and the solvent removed to give 6-(2-aminoethanoyl)-3H-benzothiazol-2-one hydrochloride as a light brown solid (0.5 g, 96%).

m/z 209.04 (MH⁺)

$v_{max}$ 3405, 2958, 1681, 1642, 1591, 1222, 1179, 814 cm⁻¹

$\delta_H$ (DMSO) 4.53 (2H, s, CH₂), 7.31(1H, d, arom., J 8.5 Hz), 7.94–7.97 (1H, m, arom.), 8.33 (1H, s, arom.), 8.43 (3H, s, NH₃⁺), 12.61 (1H, s, NH).

Step 4: Coupling of 6-(2-aminoethanoyl)-3H-(-benzothiazol-2-one hydrochloride with 35 following the procedure described in Example 6, Step 6, gave 2-[4-(4-fluorobenzyl)piperidin-1-yl]-N-[2-oxo-2-(2-oxo-2,3-dihydrobenzothiazol-6-yl)ethyl]acetamide:

$v_{max}$ (KBr) 3404m, 3346m, 4047, 1708s (ketone C═O), 1681s and 1653s (2×amide C═O), 1596m, 1508m, 1218m and 841s cm⁻¹

NMR $\delta_H$ (DMSO-d₆) 1.40–1.60 (2H, m), 1.71–1.80 (3H, m), 2.97–2.99 (2H, m), 3.45 (2H, d, J 11 Hz, CH₂C₆H₄F), 3.98 [2H, s, C(O)CH₂N], 4.73 [2H, d, J 5 Hz, C(O)CH₂NH], 7.10 (2H, t, J 8.5 Hz), 7.21–7.24 (3H, m), 7.93 (1H, dd, J 8 and 1 Hz), 8.31 (1H, d, J 1 Hz), 8.90 (1H, brs), 9.57 (1H, brs) and 12.43 (1H, brs), m/z (APCI+) 442 (MH⁺, 100%), m/z (APCI−) 440 ([M-H]⁻, 50%) and 413 (100), HPLC R$_t$=8.98 min; 97.24%; (20–100% MeCN in H₂O (both +0.1% trifluoroacetic acid) over 15 minutes at 1 mL/min, held at 100% MeCN for 5 minutes; Prodigy ODS III 5μ, 250×4.6 mm, 40° C.).

Step 5: To a stirred solution of 2-[4-(4-fluorobenzyl) piperidin-1-yl]-N-[2-oxo-2-(2-oxo-2,3-dihydrobenzothiazol-6-yl)ethyl]acetamide (0.50 g, 1.13 mmol) in 1,4-dioxan (30 mL) was added [2,4-bis(4-methoxyphenyl)-1,3-dithia-2,4-diphosphetane-2,4-disulfide] (Lawesson's reagent) (0.69 g, 1.70 mmol). The resulting suspension was heated at reflux for 24 hours. The reaction mixture was condensed to dryness in vacuo, redissolved in EtOAc, and washed with saturated aqueous sodium hydrogen carbonate, and saturated brine. The organic phase was dried (MgSO₄) and condensed to dryness in vacuo. The material was then subject to column chromatography [silica gel, EtOAc/Heptanes (0–50% EtOAc over 60 min)] gave 6-{2-[4-(4-fluorobenzyl)piperidin-1-ylmethyl]thiazol-5-yl}-3H-benzothiazol-2-one (0.087 g, 18%) as an off-white solid:

$v_{max}$ (KBr) 2918ms, 2852m, 1681s (ketone C═O), 1599m, 1507s, 1454ms, 1214m, 1214ms, 804ms, m/z (APCI+) 440 (MH⁺, 100%), 249 (10%)

m/z (APCI−) 438 ([M-H]⁻, 100%), 247 (10%),

NMR $\delta_H$ (DMSO-d₆) 1.18–1.26 (2H, dd, J 8.8, 11.7 Hz), 1.48 (1H, m), 1.56 (2H, d, J 12.9 Hz), 2.09 (2H, t, J 11.2 Hz), 2.90 (2H, d, J 11.2 Hz), 3.28 (2H, d, J 9.5 Hz), 3.75 (2H, s), 7.06–7.18 (4H, m), 7.20 (2H, t, J 8.5 Hz), 7.52 (1H, dd, J 2.0 8.3 Hz), 7.91 (1H, s), 7.92 (1H, s), 12.0 (1H, br, NH)

HPLC R$_t$=5.49 Min; 98.023%, (20% to 100% in 12 minutes, held at 100% ACN for 1 minute at 1.5 mL/min, 40 degrees. Prodigy ODS (3), 3 micron, 150×4.6 mm, 250 nm).

EXAMPLE 8

5-[2-(4-Benzylpiperidin-1-ylmethyl)thiazol-5-yl]-1,3-dihydrobenzimidazole-2-thione

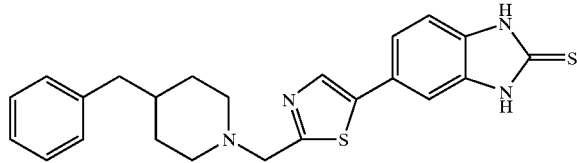

Step 1: To a stirring solution of 4-benzylpiperidine (6) (2.00 g, 11.41 mmol) in dichloromethane (20 mL) at 0° C. was added triethylamine (1.59 mL, 11.41 mmol), followed by benzyl-2-bromoacetate (1.81 mL, 11.41 mmol). After 10 minutes a white precipitate was observed. The reaction mixture was allowed to warm to room temperature. After 45 minutes the reaction mixture was condensed to dryness in vacuo, redissolved in EtOAc (50 mL), the organic phase washed with saturated aqueous sodium hydrogen carbonate (50 mL), and saturated brine (50 mL). The organic phase was dried (MgSO₄) and condensed to dryness to give (4-benzylpiperidin-1-yl)acetic acid benzyl ester (3.69 g, 100%) as a pale yellow oil:

m/z (APCI+) 324 (MH⁺, 100%), $\delta_H$ 1.36 (2H, dt, J 3.2, 8.8 Hz), 1.42 (1H, M) 1.60 (2H, d, J 13.2), 2.10 (2H, dt, J 2, 9.6 Hz), 2.52 (2H, d, J 6.8 Hz), 2.88 (2H, d, J 11.6 Hz), 3.21 (2H, s, N—CH₂—CO), 5.14 (2H, s, OCH₂Ph), 7.17 (2H, d, J 7.2 Hz), 7.24 (2H, d, J 6.0 Hz).

HPLC R$_t$=1.64 min; 68.1%; (5–100% MeCN in H₂O (both +0.1% trifluoroacetic acid) over 2.5 minutes at 3 mL/min, held at 100% MeCN for 0.5 minute; Prodigy ODS III 5μ, 50×4.6 mm).

Step 2: Hydrogenolysis of (4-benzylpiperidin-1-yl)acetic acid benzyl ester, following the procedure described on Example 6, Step 2, gave (4-benzylpiperidin-1-yl)acetic acid (2.66 g, 100%) as a white solid:

$v_{max}$ (KBr) 1626 (C═O), 1403s cm⁻¹ m/z (APCI+) 234 (MH⁺, 100%), $\delta_H$ 1.75–1.85 (5H, m), 2.60 (2H, d, J 5.6 Hz), 2.73 (2H, m), 3.57 (2H, d, J 5.6 Hz), 3.67 (2H, d, J 11.6 Hz), 4.0 (1H, s, OH), 7.12 (2H, d, J 7.2 Hz), 7.20 (1H, d, J 7.2 Hz), 7.26 (2H, t, J 7.2 Hz).

(high performance liquid chromatography) HPLC R$_t$=1.25 min; 100%; (5–100% MeCN in H₂O (both +0.1% trifluoroacetic acid) over 2.5 minutes at 3 mL/min, held at 100% MeCN for 0.5 minute; Prodigy ODS III 5μ, 50×4.6 mm).

Step 3: To a stirred solution of 1,2-phenylenediamine (10.00 g, 0.092 mol) in dimethylformamide (150 cm³) was added 1,1'-carbonyldiimidiazole (CDI, 14.99 g, 0.092 mol).

After 22 hours, the reaction mixture was evaporated and then slurried in ethyl acetate. The resulting mixture was filtered, washed with ethyl acetate, and the residue dried in vacuo to give 1,3-dihydrobenzoimidazol-2-one (12.10 g, 98%) as a white solid:

$\nu_{max}$ (KBr) 1755 (C=O) cm$^{-1}$ $\delta_H$ (DMSO-d$_6$) 6.91 (4H, s, arom.), 10.55 (2H, brs, 2×NH).

Step 4: To a stirred slurry of aluminum trichloride (22.76 g, 170.73 mmol) in 1,2-dichloroethane (20 mL) at 0° C. was added chloroacetyl chloride (15.42 g, 136.57 mmol). After 30 minutes, the substrate (9.16 g, 68.29 mmol) was added in three portions, along with further 1,2-dichloroethane (20 mL). A red-brown color was observed. The reaction mixture was heated at 50° C. for 2 hours. The mixture was then poured onto ice, and the resulting mixture filtered. The residue was washed with ethanol, which gave a white solid (17.00 g). The material was recrystallized by dissolving the crude product in DMF (70 mL), heating to 80° C., adding ethanol (70 mL), cooling to ambient temperature, and then cooling further to 0° C. The resulting precipitate was collected by filtration, washed with ethanol, and dried in vacuo to give 5-(2-chloroethanoyl)-1,3-dihydrobenzimidazol-2-one (8.09 g, 56%) as a light brown solid:

$\nu_{max}$ (KBr) 1747 (C=O), 1687s, 1636s, 1473s, 1398s, 1321s, 1267s, 1202s, 1157s and 1011s cm$^{-1}$ $\delta_H$ (DMSO-d$_6$) 5.12 (2H, s, CH$_2$Cl), 7.04 (1H, d, arom., J 8 Hz), 7.49 (1H, s, arom.), 7.68 (1H, dd, arom., J 8.5, 1.5 Hz), 10.96 (1H, s, arom.) and 11.11 (1H, s, arom.).

Step 5: Treatment of give 5-(2-chloroethanoyl)-1,3-dihydrobenzimidazol-2-one with sodium azide, following the procedure described in Example 6. Step 4, gave 6-(2-azidoethanoyl)-1,3-dihydrobenzimidazol-2-one (5.75 g, 93%):

$\nu_{max}$ 3415, 2106, 1723, 1681, 1476, 1268 cm$^{-1}$ $\delta_H$ (DMSO) 4.84 (2H, s, CH$_2$), 7.04 (1H, d, arom., J 8.3 Hz), 7.45 (1H, d, arom., J 1.2 Hz), 7.63 (1H, dd, arom., J 1.5, 8.1 Hz), 10.90–11.15 (2H, m, NH×2).

Step 6: 6-(2-Azidoethanoyl)-1,3-dihydrobenzimidazol-2-one (1.0 g, 4.6 mmol) and Pd—C (5%, 0.3g) in methanol (150 mL) and concentrated HCl (2mL), were subjected to hydrogenation at 25 psi and 27° C. for 1 hour. The catalyst was removed by filtration through a 'filter aid' and the solvent removed to give 6-(2-aminoethanoyl)-1,3-dihydrobenzimidazol-2-one hydrochloride (1.01 g, 96%) as a brown solid:

m/z 192.10 (MH$^+$)

$\nu_{max}$ 3183, 1681, 1625, 1475, 1276, 1178 cm$^{-1}$ $\delta_H$ (DMSO) 4.54 (2H, d, CH$_2$, J 5.4 Hz), 7.08 (1H, d, arom., J 8.1 Hz), 7.52 (1H, s, arom.), 7.71 (1H, dd, arom., J 1.5, 8.1 Hz), 8.34 (3H, s, NH$_3^+$), 11.08 (1H, s, NH), 11.24 (1H, s, NH).

Step 7: Condensation of 6-(2-aminoethanoyl)-1,3-dihydrobenzimidazol-2-one hydrochloride with (4-benzylpiperidin-1-yl)acetic acid, following the procedure described in Example 6, Step 6, gave 5-[2-(4-benzylpiperidin-1-ylmethyl)thiazol-5-yl]-1,3-dihydrobenzimidazole-2-one:

$\nu_{max}$ (KBr) 3431br, 1730s (ketone C=O), 1691s, 1681s, 1645s, 1528s, 1365s, 1288s, 1232s, 815s and 750s cm$^{-1}$ NMR $\delta_H$ (DMSO-d$_6$) 1.28–1.34 (2H, m), 1.49–1.57 (3H, m), 2.00 (2H, m), 2.87–2.94 (4H, m), 4.61 (2H, d, J 5.5 Hz), 7.04 (1H, d, J 8.5 Hz), 7.16–7.20 (3H, m) 7.27–7.30 (2H, m), 7.48 (1H, s), 7.69 (1H, dd, J 8.5 and 1.5 Hz), 7.98 (brs, 1H, amide NH), 10.94 and 11.11 (each 1H, s, 2×NH):

m/z (APCI+) 407 (MH$^+$, 60%) and 169 (100),

HPLC R$_t$=3.74 min; 96.11%; (20–100% MeCN in H$_2$O (both +0.1% trifluoroacetic acid) over 12 minutes at 1.5 mL/minute, held at 100% MeCN for 1 minute; Prodigy ODS III 3$\mu$, 150×4.6 mm, 40° C.).

Step 8: Treatment of 5-[2-(4-benzylpiperidin-1-ylmethyl)thiazol-5-yl]-1,3-dihydrobenzimidazole-2-thione with Lawesson's reagent, following the procedure described in Example 6, Step 7, gave 5-[2-(4-benzylpiperidin-1-ylmethyl)thiazol-5-yl]-1,3-dihydrobenzimidazole-2-thione.

Purified by preparative HPLC (10–100% ACN (0.1% TFA) over 30 minutes, held at 100% for 5 minutes at 20 mL/minute, YMC-PACK ODS-A, 5 micron, 100×30 mm, 254 nm). Yellow solid (0.031 g, 6%).

$\nu_{max}$ (KBr) 3420br, 3124br, 2921ms, 1613w, 1511w, 1466s (C(S)NH), 1333ms (NC(S)N), 1190s, 807ws, m/z (APCI+) 421 (MH$^+$, 100%), 248 (10%)

m/z (APCI-) 419 ([M-H]$^-$, 100%), 246 (10%),

NMR $\delta_H$ (DMSO-d$_6$) 1.23 (2H, m), 1.51 (1H, m), 1.54 (2H, d, J 12.2 Hz), 2.04 (2H, t, J 11.0 Hz), 2.88 (2H, d, J 11.2 Hz), 3.26 (2H, d, J 10.0 Hz), 3.75 (2H, s) 7.15 (4H, d, arom., J 8.0 Hz), 7.25 (3H, t, arom., J 8.3 Hz), 7.40 (1H, d, arom., J 8.3 Hz), 8.0 (1H, s, arom.)

HPLC R$_t$=5.94 minutes, 97.48%, (20–100% ACN (0.1% TFA) in 20 minutes, held at 100% ACN for 1 minute at 1.5 mL/minute, 40° C. liquid chromatography-mass spectrometry (LC-MS) Prodigy ODS(3), 3 micron, 150×4.6 mm 250 nm.

EXAMPLE 9

6-{2-[4-(4-Fluorobenzyl)piperidin-1-ylmethyl]oxazol-5-yl}-3H-benzothiazol-2-one

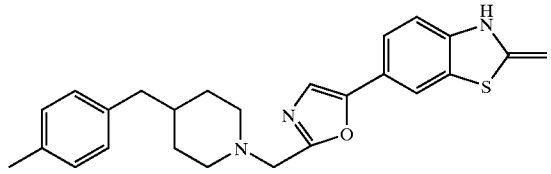

$\nu_{max}$ (KBr) 3436br, 1682 (amide C=O), 1508s, 1468s, 1346s, 1270s, 1175s, 1136s, 1087s, 989s, 947s, 822s, and 783s cm$^{-1}$ NMR $\delta_H$ (DMSO-d$_6$) 1.40–1.50 (2H, m), 1.75–1.79 (3H, m), 3.05–3.10 (2H, m), 3.55–3.58 (2H, m), 4.59 (2H, brs), 7.12 (2H, t, J9 Hz), 7.21 (2H, t, J 8 Hz), 7.67 (1H, dd, J 9 and 1.5 Hz), 7.75 (1H, s), 7.86 (1H, s), 8.00 (1H, d, J 8 Hz) and 9.95 (1H, brs), m/z (APCI-) 422 ([M-H]$^-$100%), HPLC R$_t$=4.55 min; 96.86%; (20–100% MeCN in H$_2$O (both +0.1% trifluoroacetic acid) over 7 minutes at 1.5 mL/minute, held at 100% MeCN for 1 minute; Prodigy ODS III 5$\mu$, 250×4.6 mm, 40° C.).

EXAMPLE 10

6-[2-(4-Benzylpiperidin-1-ylmethyl)oxazol-5-yl]-3H-benzoxazol-2-one

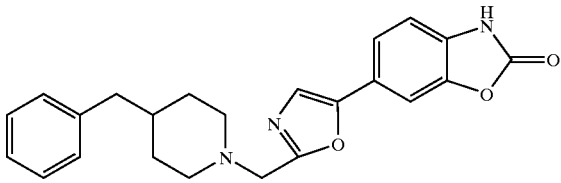

Step 1: Coupling of (4-benzylpiperidin-1-yl)acetic acid with 39, following the procedure described in Example 6, Step 6, gave 2-(4-benzylpiperidin-1-yl)-N-[2-oxo-2-(2-oxo-2,3-dihydrobenzoxazol-6-yl)ethyl]acetamide:

$v_{max}$ (KBr) 3380w, 3091w, 3023m, 2911w, 1773s, 1676w, 1648s, 1616m, 1528m, 1450m, 1424m, 1353w, 1266s, 923m, 912m, and 748m cm$^{-1}$ NMR $\delta_H$ (DMSO-d$_6$) 1.17–1.33 (2H, m), 1.50–1.57 (3H, m), 1.99–2.04 (2H, m), 2.87–2.89 (2H, m), 2.94 (2H, s), 3.29 (2H, s), 4.61 (2H, d, J 5.5 Hz), 7.16–7.21 (4H, m), 7.28 (2H, t, J 8 Hz), 7.84–7.87 (2H, m), and 8.01 (1H, brs, amide NH):

m/z (APCI+) 408 (MH$^+$, 100%), m/z (APCI−) 406 ([M−H]$^-$, 100%), HPLC R$_t$=5.30 min; 96.05%; (20–100% MeCN in H$_2$0 (both +0.1% trifluoroacetic acid) over 20 minutes at 1.5 mL/minute, held at 100% MeCN for 3 minutes; Prodigy ODS III 3$\mu$, 150×4.6 mm, 40° C.).

Step 2: 6-[2-(4-Benzylpiperidin-1-ylmethyl)oxazol-5-yl]-3H-benzoxazol-2-one was prepared from 2-(4-benzylpiperidin-1-yl)-N-[2-oxo-2-(2-oxo-2,3-dihydrobenzoxazol-6-yl)ethyl]acetamide following the procedure described in Example 9, Step 1:

$v_{max}$(KBr) 3435br, 1783s, 1766s, 1495m, 1485m, 1311m, 1286m, 128m, 1053m, 968w, and 753w cm$^{-1}$ NMR $\delta_H$ (DMSO-d$_6$) 1.20–1.40 (2H, m), 1.25–1.70 (3H, m), 2.10–2.40 (2H, m), 2.90–3.10 (2H, m), 3.70–3.85 (2H, m), 7.16–7.26 (4H, m), 7.48–7.63 (3H, m) and 11.82 (1H, brs)

m/z (APCI+) 390 (MH$^+$, 18%) and 169 (100)

HPLC R$_t$=6.26 min; 95.61%; (20–100% MeCN in H$_2$0 (both +0.1% trifluoroacetic acid) over 20 minutes at 1.5 mL/minute, held at 100% MeCN for 3 minutes; Prodigy ODS III 3$\mu$, 150×4.6 mm, 40° C.).

EXAMPLE 11

5-[2-(4-Benzylpiperidin-1-ylmethyl)oxazol-5-yl]-1,3-dihydroindol-2-one

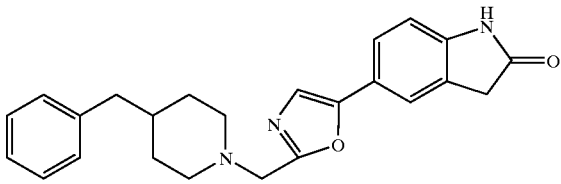

Step 1: 5-(2-Chloroethanoyl)-1,3-dihydroindol-2-one was prepared following the procedure described in Example 6, Step 3:

$\delta_H$(d$_6$-Me$_2$SO) 3.57 (2H, s, ArCH$_2$C(O)NH), 5.08 (2H, s, CH$_2$Cl), 6.93 (1H, d, arom., J 8.0 Hz), 7.83 (1 H, s, arom.), 7.88 (1H, d, arom., J 8.0 Hz) and 10.82 (1H, brs, NH), m/z (APCI−) 210 and 208 (each [M−H]$^-$, 35 and 100%).

Step 2: Treatment of 5-(2-chloroethanoyl)-1,3-dihydroindol-2-one with sodium azide, following the procedure described in Example 6, Step 4, gave 6-(2-azidoethanoyl)-1,3-dihydroindol-2-one (6.58 g, 91%):

m/z 215.08 (M−H$^-$)

$v_{max}$ 3229, 2122, 1715, 1679, 1615, 1236, 1123, 824 cm$^{-1}$ $\delta_H$ (DMSO) 3.57 (2H, s, CH$_2$CO), 4.79 (2H, s, CH$_2$N$_3$), 6.93 (1H, d, arom., J 8.1 Hz), 7.79 (1H, s, arom.), 7.83 (1H, s, arom.,J 8.3 Hz), 10.78 (1H, bs, NH).

Step 3: Reduction of 6-(2-azidoethanoyl)-1,3-dihydroindol-2-one, following the procedure described in Example 6, Step 5, gave 6-(2-aminoethanoyl)-1,3-dihydroindol-2-one hydrochloride (2.96 g, 63%):

m/z 191.05 (MH$^+$)

$v_{max}$ 3401, 3205, 1687, 1619, 1493, 1423, 1312, 1247 cm$^{-1}$ $\delta_H$(DMSO) 3.58 (2H, s, CH$_2$CO), 4.49 (2H, d, CH$_2$, J 5.4 Hz), 6.98 (1H, d, arom., J 8.3 Hz), 7.87 (1H, s, arom.), 7.92 (1H, d, arom., J 8.3 Hz), 8.35 (3H, s, NH$_3^+$), 10.95 (1H, s, NH).

Step 4: Condensation of 6-(2-aminoethanoyl)-1,3-dihydroindol-2-one hydrochloride with (4-benzylpiperidin-1-yl)acetic acid, following the procedure described in Example 6, Step 6, gave 2-(4-benzyl-piperidin-1-yl)-N-[2-oxo-2-(2-oxo-2,3-dihydro-1H-indol-5-yl)ethyl]acetamide:

$v_{max}$ (KBr) 3352br, 3173br, 2918m, 1717s (ketone C═O), 1679s, 1649s, 1621s, 1523s, 1361s, 1252s, 1101s m/z (APCI+) 406 (MH$^+$, 100%), 169 (25%)

m/z (APCI−) 404 ([M−H]$^-$, 100%).

NMR $\delta_H$ (DMSO-d$_6$) 1.31 (2H, dt, J 3.0, 12.4 Hz), 1.51 (1H, m), 1.54–1.57 (2H, d, J 12.4 Hz), 2.86 (2H, d, J 11.6 Hz), 2.92 (2H, s), 3.29 (2H, d, J 9.2 Hz), 3.56 (2H, s), 4.56 (2H, d, J 6 Hz), 6.90 (1H, d, J 8 Hz), 7.18 (3H, m), 7.26 (2H, t, arom., J 7.2 Hz) 7.90 (1H, d, arom., J 8.4 Hz) 7.95 (1H, t, arom., J 5.6)

HPLC R$_t$=4.00 Min; 97.49%, (20–100% ACN (0.1% TFA) in 12 minutes, held at 100% acetonitrile (ACN) for 1 minute at 1.5 mL/minute, 40 degrees. Prodigy ODS (3), 3 micron, 150×4.6 mm, 250 nm.

Step 5:5-[2-(4-Benzylpiperidin-1-ylmethyl)oxazol-5-yl]-1,3-dihydroindol-2- was prepared from 2-(4-benzyl-piperidin-1-yl)-N-[2-oxo-2-(2-oxo-2,3-dihydro-1H-indol-5-yl)ethyl]acetamide following the procedure described in Example 9, Step 1:

$v_{max}$ (KBr) 3439br, 1697s, 1624m, 1485m, 1239m, 1112m, 1050m and 815m cm$^{-1}$ NMR $\delta_H$ (DMSO-d$_6$) 1.15–1.18 (2H, m), 1.20–1.46 (3H, m), 2.02 (2H, t, J 11 Hz, 2.83 (2H, d, J 12 Hz), 3.54 (2H, s), 3.63 (2H, s), 6.89 (1H, d, J 8 Hz), 7.13–7.18 (3H, m), 7.24–7.28 (2H, m), 7.42 (1H, s), 7.49 (1H, d, J 8 Hz), 7.53 (1H, s) and 10.53 (1H, s, amide NH)

m/z (APCI+) 388 (MH+, 100%)

m/z (APCI−) 386 ([M−H]$^-$, 100%)

HPLC R$_t$=4.40 minutes; 99.40%; (20–100% MeCN in H$_2$O (both +0.1% trifluoroacetic acid) over 12 minutes at 1.5 mL/minute, held at 100% MeCN for 1 minute; Prodigy ODS III 3$\mu$, 150×4.6 mm, 40° C.).

EXAMPLE 12

6-{5-[4-(4-Fluorobenzyl)piperidin-1-ylmethyl]-4,5-dihydrothiazol-2-yl}-3H-benzoxazol-2-one

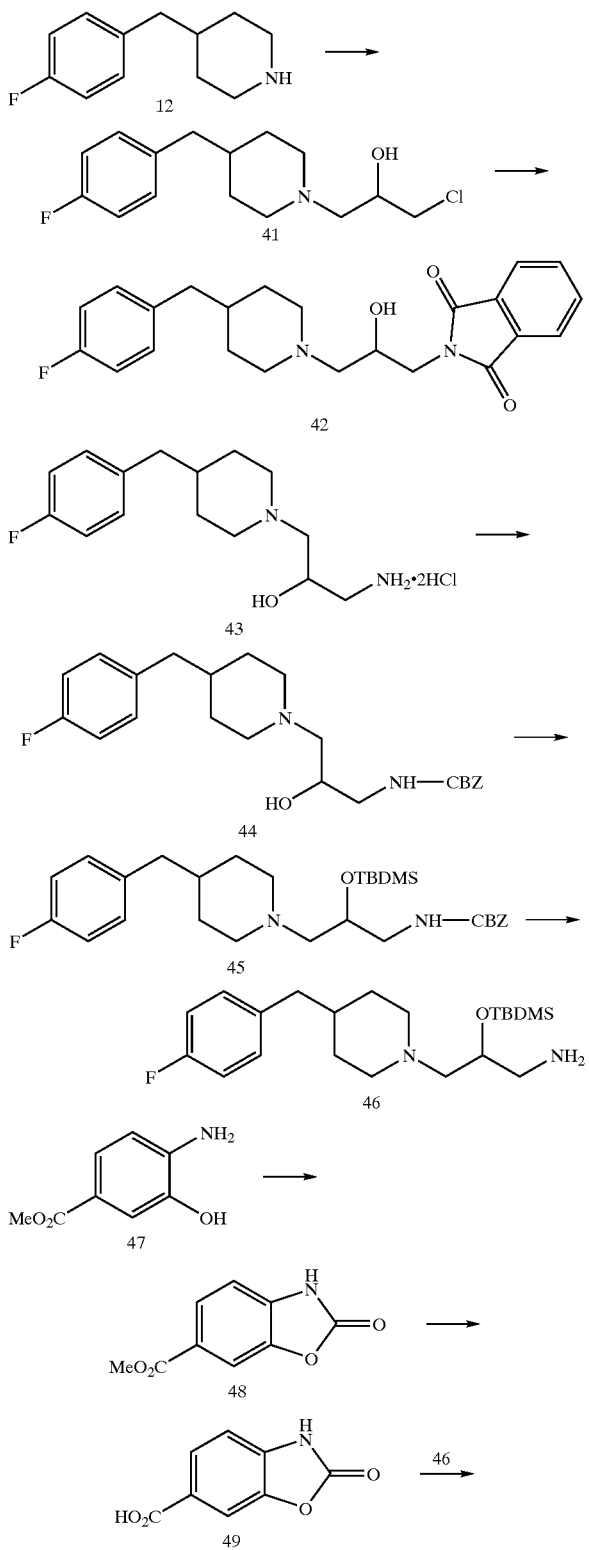

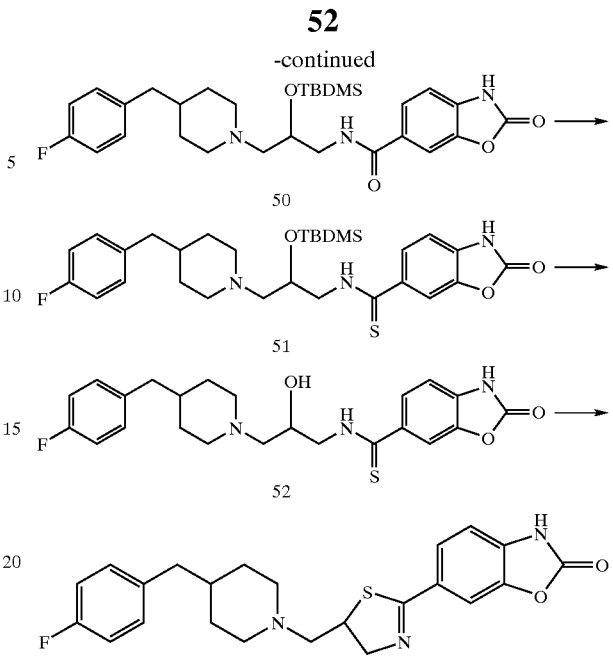

Step 1: 4-(4-Fluorobenzyl)piperidine hydrochloride (12) (20.0 g, 87.1 mmol), epichlorohydrin (8.06 g, 87.0 mmol) and triethylamine (8.80 g, 87.1 mmol) in EtOH (200 mL) were stirred at ambient temperature for 96 hours. The solvent was removed and the material taken up in EtOAc, washed with saturated NaHCO$_3$, brine and dried (MgSO$_4$) to give 41 (16.69 g, 67%) as an orange solid:

$^1$H-NMR (CDCl$_3$) $\delta_H$ inter alia 1.22–1.35 (2H, m), 1.47–1.53 (1H, m), 1.62 (2H, dd, J 13 and 2.5 Hz), 1.95 and 2.24 (each 1 H, dt, J 11.5, 2.5 and 2.5 Hz), 2.42–2.44 (2H, m, CH$_2$Ph), 2.50 (2H, d, J 7 Hz), 2.80 and 2.94 (each 1H, d, J 11.5 Hz), 3.55 (2H, d, J 5 Hz, CH$_2$Cl), 3.87–3.93 (1H, m, CHOH), 6.93–6.99 and 7.06–7.10 (each 2H, m)

m/z (APCI+) 286 (MH$^+$, 100%) and 250 ([M−Cl]$^+$, 60).

Step 2: Compound 41 (16.69 g, 58.46 mmol) and potassium phthalimide (10.81 g, 58.46 mmol) in DMF (100 mL) were heated to 100° C. for 2 hours. The solvent was removed and the material taken up in EtOAc, washed with brine dried (MgSO$_4$) and evaporated. The residue was partially purified by silica gel column chromatography (CH$_2$Cl$_2$) to yield a 1:1 mixture of 42 and phthalimide (13.91 g, 44%) as a white solid:

$^1$H-NMR (CDCl$_3$) $\delta_H$ 1.16–1.30 (2H, m), 1.43–1.51 (3H, m), 1.88 and 2.20 (each 1H, dt, J 11.5 and 2.5 Hz), 2.33–2.43 (2H, m), 2.47 (2H, d, J 7 Hz), 2.78 and 2.89 (each 1H, d, J 4.5 Hz), 3.63–3.82 (2H, m), 3.94–4.02 (1H, m), 6.97 (2H, t, J 11 Hz), 7.05–7.08 (2H, m), 7.69–7.79 (2H, m) and 7.84–7.89 (2H, m)

m/z (APCI+) 267 (MH$^+$, 100%).

Step 3: Compound 42 (13.91 g, 25.6 mmol—impure mixture) and hydrazine hydrate (3.84 g, 76.89 mmol) in ethanol (100 mL) and water (100 mL) were heated under reflux conditions for 3 hours, and then left to stir at ambient temperature for 16 hours. The solvent was removed, and the crude material was acidified with 10% aqueous hydrochloric acid. The precipitate was filtered and the pad washed with water; the filtrate was concentrated to yield 43 (13.5 g, >100%, wet) as a yellow solid which was partially dried in vacuo:

NMR $\delta_H$ (MeOH-d$_4$) inter alia 1.55–1.69 (2H, m), 1.85–1.92 (3H, m), 2.60 (2H, d, J 6.5 Hz), 2.86–3.24 (6H, m), 3.60–3.68 (2H, m), 4.30–4.36 (1H, m), 7.01 (2H, t J 8.5 Hz) and 7.18–7.24 (2H, m)

m/z (APCI+) 267 (MH+, 100%).

Step 4: Benzyl chloroformate (4.26 g, 25.0 mmol) was added to a mixture of 43 (5.92 g, 17.57 mmol) and sodium carbonate decahydrate (21.45 g, 75.0 mmol) in dioxane-water (100–10 mL), and the resulting mixture stirred at ambient temperature for 4 hours. The solvent was removed, the material diluted with EtOAc, washed with water followed by brine, and then dried (MgSO$_4$) and evaporated. The product was purified by column chromatography (silica gel, 0% to 5% MeOH in CH$_2$Cl$_2$) 44 (2.10 g, 30%) as a clear oil which solidified on standing:

m/z 401.21 (MH+)

$v_{max}$ 3339, 2924, 1716, 1509, 1220 cm$^{-1}$.

$^1$H-NMR (CDCl$_3$) $\delta_H$ 1.25 (3H, m, alkyl), 1.60 (2H, m, alkyl), 1.82 (1H, m, alkyl), 2.22 (1H, m, alkyl), 2.28 (2H, d, CH$_2$, J 7.2 Hz), 2.49 (2H, d, CH$_2$, J 7.2 Hz), 2.72 (1H, d, CHH, J 12.0 Hz), 2.93 (1H, d, CHH, J 12.0 Hz), 3.10 (1H, m, CHH), 3.41 (1H, m, CHH), 3.70 (1H, m, CHO), 5.10 (2H, s, CH$_2$O), 5.20 (1H, bs, NH), 6.98 (2H, m, arom.), 7.07 (2H, m, arom.), 7.32 (5H, m, Ph).

Step 5: tert-Butyldimethylsilyl trifluorosulfonate (1.94 g, 7.35 mmol) was added to a cooled (0° C.) solution of 44 (2.10 g, 5.25 mmol) and 2,6-lutidine (1.12 g, 10.50 mmol) in dichloromethane (20 mL). After 15 minutes, the mixture was diluted with dichloromethane, washed with saturated NaHCO$_3$ followed by brine, and then dried (MgSO$_4$) and evaporated to give 45 (2.80 g, quantitative) as a clear oil:

m/z 515.29 (MH+) $v_{max}$ 3350, 1721, 1510, 1255, 1222 cm$^{-1}$.

Step 6: Compound 45 (2.70 g, 5.25 mmol) was hydrogenated at 50 psi and 30° C. in the presence of Pd(OH)$_2$—C (100 mg) in MeOH (20 mL) for 8 hours. The mixture was filtered through a 'filter-aid' and the solvent removed to yield 46 (1.83 g, 92%) as a clear gum:

m/z 381.31 (MH+)

$v_{max}$ 3382, 2928, 1510, 1030, 837 cm$^{-1}$ $^1$H-NMR (CDCl$_3$) $\delta_H$ 0.08 (6H, s, Si(CH$_3$)$_2$), 0.88 (9H, s, $^t$Bu), 1.25 (2H, m, CH$_2$), 1.45 (1H, m, CH), 1.60 (2H, m, CH$_2$), 2.02 (2H, m, CH$_2$), 2.25 (2H, bs, NH$_2$), 2.47 (4H, m, 2×CH$_2$), 2.88 (2H, d, CH$_2$, J 4.4 Hz), 2.89 (2H, bt, CH$_2$, J 12.0 Hz), 3.81 (1H, m, CHO).

Step 7: Methyl 4-amino-3-hydroxybenzoate (47) (11.01 g, 65.9 mmol) and CDI (11.21 g, 69.2 mmol) were stirred in DMF (75 mL) at room temperature for 1 hour. The DMF was then removed and the mixture diluted with EtOAc, washed with 0.5 M NaOH, 10% HCl, brine and dried (MgSO$_4$) to give 48 (7.52 g, 59%) as a brown solid:

m/z 191.98 (M–H)–

$v_{max}$ 3402, 1746, 1708, 1290 cm$^{-1}$ $^1$H-NMR (CDCl$_3$) $\delta_H$ (DMSO-d$_6$) 3.85 (3H, s, OCH$_3$), 7.19 (1H, d, arom., J 8.4 Hz), 7.76 (1H, d, arom., J 1.6 Hz), 7.82 (1H, dd, arom., J 1.6, 8.4 Hz), 12.07 (1H, bs, NH).

Step 8: Compound 48 (8.0 g, 41.5 mmol) and LiOH.H$_2$O (3.49 g, 83.0 mmol) in MeOH—H$_2$O (100–10 mL) were heated under reflux conditions for 4 hours. An aliquot of LiOH.H$_2$O (1.75 g, 42.0 mmol) was added and the heating continued for a further 3 hours. The solvent was removed, and the solids were slurried in 10% HCl then filtered and washed with H$_2$O and dried in vacuo to give 49 (7.40 g, quantitative) as a brown solid:

m/z 177 (M–H)–

$v_{max}$ 3431, 3120, 1769, 1685, 1619, 1427, 1296 cm$^{-1}$

NMR $\delta_H$ (DMSO-d$_6$) 7.17 (1H, d, arom., J 8.4 Hz), 7.40 (1H, d, arom., J 1.2 Hz), 7.80 (1H, dd, arom., J 1.2, 8.4 Hz), 12.02 (1H, bs, NH), 13.89 (1H, bs, OH).

Step 9: Compound 49 (980 mg, 69%) as a brown foam:

m/z 542.27 (MH+)

$^1$H-NMR (CDCl$_3$) $\delta_H$ 0.12 (3H, s, SiCH$_3$), 0.13 (3H, s, SiCH$_3$), 0.89 (9H, s, Si$^t$Bu), 1.66 (1H, bs, alkyl), 1.80 (2H, bs, alkyl), 2.40 (2H, bs, alkyl), 2.57 (2H, m alkyl), 2.79 (1H, bs, alkyl), 2.96 (1H, bs, alkyl), 3.31 (1H, bs, allyl), 3.53 (2H, bs, alkyl), 3.66 (2H, m, alkyl), 4.20 (1H, bs, CHO), 6.96–7.12 (5H, m, arom.), 7.58 (1H, s, arom.), 7.66 (1H, d, arom., J 8.0 Hz), 7.99 (1H, bs, NH).

Step 10: Compound 50 (980 mg, 1.81 mmol) and Lawesson's reagent (366 mg, 906 $\mu$mol) in dioxane (5 mL) were heated under reflux conditions for 1 hour. A further aliquot of Lawesson's reagent (732 mg, 1.81 mmol) was added, and heating continued for 1.5 hours. The solvent was removed and the product was diluted with EtOAc, washed extensively with saturated NaHCO$_3$, brine, and dried. The product was purified by chromatography (silica gel, 0–50% EtOAc in heptane) to give 6-[5-(4-(4-fluorobenzyl)piperidin-1-ylmethyl)-4,5-dihydro-thiazol-2-yl]-3H-benzoxazol-2-one (194 mg, 25%) as a white solid:

m/z 426.18 (MH+)

$v_{max}$ 1773, 1509 cm$^{-1}$ $^1$H-NMR (CDCl$_3$) $\delta_H$ 1.25 (2H, m, alkyl), 1.56 (3H, m, alkyl), 1.97 (2H, t, CH$_2$, J 11.2 Hz), 2.56 (4H, m, alkyl), 2.89 (2H, bm, alkyl), 4.11 (1H, 1, CHS, J 6.4 Hz), 4.35 (2H, m, CH$_2$N), 6.96 (2H, m, arom.), 7.06 (3H, m, arom.), 7.63 (1H, dd, arom., J 1.0, 8.0 Hz), 7.73 (1H, d, arom., J 1.2 Hz)

HPLC Rt=3.81 minutes, 99.10% (20–100% MeCN in H2O (both +0.1% formic acid) over 7 minutes at 1.5 mL/min; Prodigy ODS III 3$\mu$, 150×4.6 mm, 40° C.)

EXAMPLE 13

6-[5-(4-Benzylpiperidin-1-ylmethyl)-4,5-dihydrothiazol-2-yl]-3H-benzoxazol-2-one

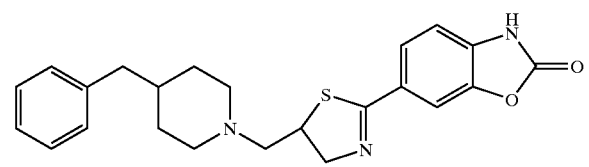

Step 1: Treatment of amine 6 with epichlorohydrin, following the procedure described in Example 12, Step 1, gave crude 1-chloro-3-(4-benzylpiperidin-1-yl)propan-2-ol (29.03 g, >100%) as a clear, colorless oil:

$v_{max}$ (neat) 3300 (brs, OH), 2921s, 1603m, 1494m, 1453s, 1091s, 1058s, 747s $^1$H-NMR (CDCl$_3$) $\delta_H$ 1.24–1.30 (2H, m), 1.50–1.60 (1H, m), 1.61–1.65 (2H, m), 1.93, 2.24 (each 1H, dt, J 11.5 and 2 Hz), 2.36–2.46 (2H, m), 2.53 (2H, d, J 7 Hz, CH$_2$N), 2.78, 2.92 (each 1H, d, J 12 Hz, CH$_2$Ph), 3.53–3.55 (2H, m, CH$_2$Cl), 3.86–3.92 (1H, m, CHOH), 7.09–7.29 (5H, m, Ph)

m/z (APCI+) 270 and 268 (each MH+, 40 and 100%) and 232 ([M–Cl]+, 40).

Step 2: Treatment of 1-chloro-3-(4-benzylpiperidin-1-yl)propan-2-ol with potassium phthalimide, following the procedure described in Example 12, Step 2, gave 2-[3-(4-benzylpiperidin-1-yl)-2-hydroxypropyl]isoindole-1,3-dione (32.44 g, 86%) as a white solid:

¹H-NMR (CDCl₃) $\delta_H$ 1.13–1.35 (2H, m), 1.45–1.49 (1H, m), 1.50–1.58 (2H, m), 1.87 and 2.19 (each 1H, dt, J 11.5, 11.5 and 2 Hz), 2.31–2.45 (2H, m), 2.50 (2H, d, J 7 Hz, NCH₂CH(OH), 2.76 and 2.86 (each 1H, d, J 12 Hz), 3.68 and 3.79 (each 1H, dd, J 13.5 and 4.5 Hz, CH₂N), 3.96–4.03 (1H, m, CHOH), 7.10–7.28 (5H, m, Ph), 7.68–7.75, and 7.82–7.86 (each 2H, m, phthalimide)

m/z (APCI+) 379 (MH+, 100%).

Step 3: Treatment of 2-[3-(4-benzylpiperidin-1-yl)-2-hydroxypropyl]-isoindole-1,3-dione with hydrazine hydrate, following the procedure described in Example 12, Step 3, gave 1-amino-3-[4-benzylpiperidin-1-yl]propan-2-ol bis-hydrochloride salt (24.32 g) as a yellow hygroscopic solid:

$v_{max}$ (KBr) 3418br, 2934br, 1712m, 1603m, 1494m, 1454m, 1066m, 945m and 748m NMR $\delta_H$ (CD₃OD) 1.59–1.62 (2H, m), 1.86–1.93 (3H, m), 2.61 (2H, d, J 6.5 Hz), 2.90–3.31 (6H, m), 3.60–3.64 (2H, m), 4.30–4.40 (1H, m, CHOH), 7.17–7.20 (2H, m) and 7.22–7.26 (2H, m).

m/z (APCI+) 249 (MH⁺, 100%).

Step 4: To a stirring solution of 1-amino-3-(4-benzylpiperidin-1-yl)propan-2-ol (2.00 g, 6.23 mmol) in 1,4-dioxan/H₂O (4:1, 25 mL) was added solid sodium hydroxide (0.28 g, 6.85 mmol). On full dissolution of the sodium hydroxide, dibenzyl dicarbonate (1.96 g, 6.85 mmol) was added. The resulting solution was stirred for 22 hours. The reaction mixture was condensed to dryness in vacuo to give a yellow gum. This was redissolved in EtOAc, washed with saturated aqueous sodium bicarbonate solution, and saturated brine. The organic phase was dried (MgSO₄) and condensed to dryness in vacuo to give a yellow oil. The oil was subject to column chromatography [silica gel, MeOH-DCM (0–20% MeOH over 30 minutes)] to give [3-(4-benzylpiperidin-1-yl)-2-hydroxypropyl]carbamic acid benzyl ester (1.64 g, 69%) as an orange solid:

m/z (APCI+) 383 (MH⁺, 100%)

¹H-NMR (CDCl₃) $\delta_H$ 1.2–1.3 (2H, m), 1.5 (1H, m), 1.60 (2H, d, J 13.1 Hz), 1.85 (1H, t, J 11.2 Hz), 2.20 (1H, t, J 11.2 Hz), 2.27 (2H, d, J 6.8 Hz), 2.51 (2H, d, J 7.0 Hz), 2.70 (1H, d, J 11.2 Hz), 2.90 (1H, d, J 11.2 Hz), 3.10 (1H, m), 3.40 (1H, d, J 3.6 Hz), 3.70 (1H, d, J 3.4 Hz), 5.10 (2H, s, CH₂O), 5.25 (1H, s, NH), 7.11 (2H, d, arom., J 7.2 Hz), 7.18 (1H, t, arom., J 7.6 Hz), 7.25–7.35 (7H, m, arom.)

HPLC R$_t$=1.62 min; 71.1%; (5–100% MeCN in H₂O (both +0.1% trifluoroacetic acid) over 2.5 minutes at 3 mL/minute, held at 100% MeCN for 0.5 minute; Prodigy ODS III 5μ, 50×4.6 mm).

Step 5: Treatment of [3-(4-benzylpiperidin-1-yl)-2-hydroxypropyl]carbamic acid benzyl ester with tert-Butyldimethylsilyl trifluorosulfonate, following the procedure described in Example 12, Step 5, gave {2-(tert-butyldimethylsilanyloxy)-3-[4-benzylpiperidin-1-yl]propyl}carbamic acid benzyl ester as a yellow oil:

m/z 497.42 (MH⁺)

$v_{max}$ 3353, 2927, 1726, 1253, 1100, 836 cm⁻¹

¹H-NMR (CDCl₃) $\delta_H$ 0.05 (6H, s, Si(CH₃)₂), 0.86 (9H, s, Si$^t$Bu), 1.25 (2H, m, alkyl), 1.45 (1H, m, CH), 1.60 (2H, m, alkyl), 1.90 (2H, m, alkyl), 2.33 (2H, d, 2×CH, J 6.0 Hz), 2.48 (2H, d, CH₂, J 7.2 Hz), 2.83 (2H, bd, CH₂, J 10.4 Hz), 3.27 (2H, m, CH₂), 3.82 (1H, m, CHO), 5.10 (2H, s, CH₂O), 5.85 (1H, bm, NH), 7.11 (2H, m, arom.), 7.18 (1H, m, arom.), 7.28–7.37 (5H, m, arom.).

Step 6: Hydrogenation of {2-(tert-butyldimethylsilanyloxy)-3-[4-benzylpiperidin-1-yl]propyl}carbamic acid benzyl ester, following the procedure described in Example 12, Step 6, gave {2-(tert-butyldimethylsilanyloxy)-3-[4-benzylpiperidin-1-yl]-propylamine as a white semi-solid:

m/z 363.19 (MH⁺)

$v_{max}$ 2927, 1252, 1075, 836, 770 cm⁻¹

¹H-NMR (CDCl₃) $\delta_H$ 0.075 (3H, s, SiCH₃), 0.08 (3H, s, SiCH3), 0.89 (9H, Si$^t$Bu), 1.28 (1H, m, alkyl), 1.63 (5H, m, alkyl, NH₂), 1.92 (2H, m, alkyl), 2.30 (2H, d, 2×CH), 2.51 (2H, d, CH₂, J 6.8 Hz), 2.69 (1H, dd, CH, J 5.2, 12.8 Hz), 2.78 (0.5H, d, 0.5×CH, J 4.4 Hz), 2.82 (2.5H, m, alkyl), 3.73 (1H, m, CHO), 7.14 (2H, m, arom.), 7.20 (1H, m, arom.), 7.26 (2H, m, arom.).

Step 7: Compound 49 (271 mg, 1.51 mmol), HBTU (574 mg, 1.51 mmol) and DIPEA (391 mg, 3.03 mmol) were stirred in DMF (5 mL) for 10 minutes, then {2-(tert-butyldimethylsilanyloxy)-3-[4-(benzyl)piperidin-1-yl]propylamine (548 mg, 1.51 mmol), was added and stirring continued for 1 hour. The solvent was removed, and the mixture diluted with EtOAc, washed with saturated NaHCO₃, brine and dried (MgSO₄). The crude material was purified by chromatography (silica gel, CH₂Cl₂) to give 2-oxo-2,3-dihydrobenzoxazole-6-carboxylic acid [3-(4-benzylpiperidin-1-yl)-2-(tert-butyldimethyl-silanyloxy)propyl]amide (786 mg, 99%) as a brown foam:

m/z 542.22 (MH⁺)

$v_{max}$ 3376, 2929, 1781, 1640, 1494, 840 cm⁻¹.

Step 8: 2-Oxo-2,3-dihydrobenzoxazole-6-carboxylic acid [3-(4-benzylpiperidin-1-yl)-2-(tert-butyldimethyl-silanyloxy)propyl]amide (686 mg, 1.31 mmol) and Lawesson's reagent (530 mg, 1.31 mmol) in dioxane (5 mL) were heated under reflux conditions for 2 hours. The solvent was removed, and the product was purified by chromatography (silica gel, 0–50% EtOAc in heptane) to give 2-oxo-2,3-dihydrobenzoxazole-6-carbothioic acid [3-(4-benzylpiperidin-1-yl)-2-(tert-butyldimethylsilanyloxy)propyl]amide (559 mg, 79%): as a green gum:

m/z 540.33 (MH⁺)

$v_{max}$ 3218, 1771, 1595, 1495, 1255, 1108 cm⁻¹

¹H-NMR (CDCl₃) $\delta_H$ aliphatics of little use due to rotamers, 7.07 (1H, d, arom., J 7.2 Hz), 7.20 (1H, d, arom., 7.2 Hz), 7.21–7.29 (5H, m, Ph), 7.74 (1H, s, arom.).

Step 9: Tetrabutylammonium fluoride (TBAF) (1.24 μmol, 1.24 mL, 1 M in THF) was added to a mixture of 2-oxo-2,3-dihydrobenzoxazole-6-carbothioic acid [3-(4-benzylpiperidin-1-yl)-2-(tert-butyldimethylsilanyloxy)propyl]amide (336 mg, 623 μmol) and 4 Å molecular sieves (1 g) in THF (2 mL). After stirring at room temperature for 1.5 hours, the mixture was diluted with EtOAc, washed with saturated NaHCO₃, brine and dried (MgSO₄) to yield 2-oxo-2,3-dihydrobenzoxazole-6-carbothioic acid [3-(4-benzylpiperidin-1-yl)-2-hydroxypropyl]amide (280 mg, quantitative) as a solid yellow foam:

m/z 426.29 (MH⁺)

$v_{max}$ 3306, 2924, 1770, 1660, 1264, 1059 cm⁻¹

¹H-NMR (CDCl₃) $\delta_H$ some TBAF still present, hence aliphatics unclear; 2.52 (2H, d, CH₂, J 7.2 Hz), 2.80 (1H, d, CHH, J 11.2 Hz), 2.99 (1H, d, CHH, J 11.2 Hz), 3.25 (2H, m, CH₂), 3.83 (1H, m, OH), 4.07 (1H, m, CHO), 7.05 (1H, d, arom., J 8.4 Hz), 7.12 (2H, d, arom., J 8.4 Hz), 7.20 (1H, d, arom., J 7.2 Hz), 7.28 (2H, m, arom.), 7.59 (1H, d, arom., J 8.0 Hz), 7.12 (1H, d, arom., J 1.6 Hz), 8.42 (1H, bs, NH).

Step 10: 2-Oxo-2,3-dihydrobenzoxazole-6-carbothioic acid [3-(4-benzylpiperidin-1-yl)-2-hydroxypropyl]amide (240 mg, 565 μmol) and Burgess reagent (134 mg, 565 μmol) in THF (5 mL) were heated under reflux conditions for 1 hour. The mixture was diluted with EtOAc, washed with saturated NaHCO$_3$, brine and dried (MgSO$_4$). Purification by chromatography (silica gel, CH$_2$Cl$_2$) gave the product as a yellow foam (91 mg), this was then repurified by chromatography (silica gel, 0–50% EtOAc in heptane) to give 6-[5-(4-benzylpiperidin-1-ylmethyl)-4,5-dihydrothiazol-2-yl]-3H-benzoxazol-2-one (52 mg, 23%) as an off white solid:

m/z 408.21 (MH$^+$)

$v_{max}$ 3261, 1777, 1494, 1447, 1273 cm$^{-1}$ $^1$H-NMR (CDCl$_3$) $\delta_H$ 1.31 (4H, m, alkyl), 1.60 (3H, m, alkyl), 1.97 (2H, t, CH$_2$, J 7.2 Hz), 2.53 (4H, 2×d, alkyl, J 6.4, 7.2 Hz), 2.90 (2H, bs, alkyl), 4.12 (1H, m, CHS), 4.35 (2H, m, CH$_2$N), 7.03 (1H, d, arom., J 8.0 Hz), 7.13–7.30 (5H, m, Ph), 7.62 (1H, dd, arom., J 1.6, 8.0 Hz), 7.73 (1H, d, arom., J 1.6 Hz).

EXAMPLE 14

6-[2-(4-Benzylpiperidin-1-ylmethyl)-4,5-dihydrothiazol-5-yl]-3H-benzoxazol-2-one

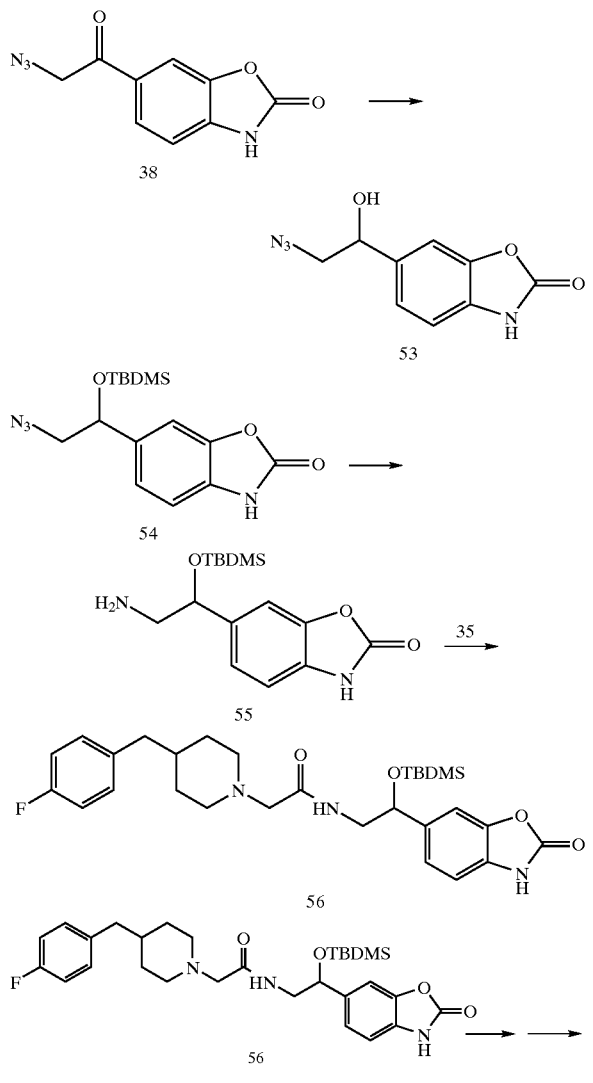

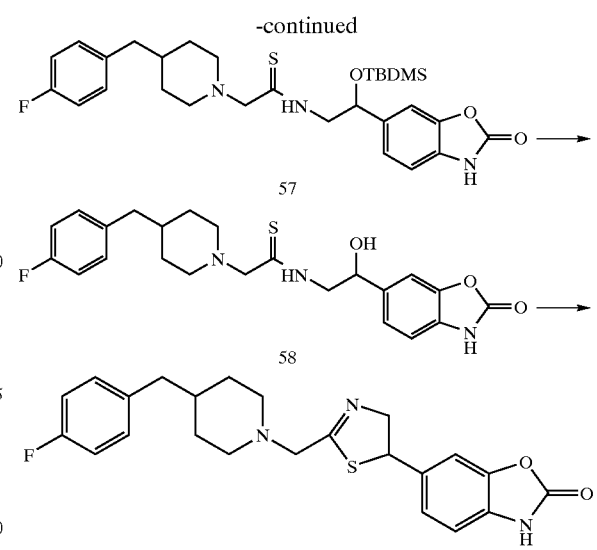

Step 1: Sodium borohydride (603 mg, 15.46 mmol) was added to a solution of 38 (3.37 g, 15.46 mmol) in EtOH-MeOH (50–50 mL) at 0° C. and stirred and allowed to warm to room temperature over 1 hour. The solvent was removed and the mixture diluted with EtOAc, washed with brine and dried (MgSO$_4$) to give 53 (2.09 g, 61%) as an orange/brown solid:

m/z 219.07 (M–H)$^-$ $v_{max}$ 3258, 2105, 1758 cm$^{-1}$

NMR $\delta_H$ (DMSO-d$_6$) 3.34 (2H, ddd, CH$_2$, J 4.0, 7.6, 12.8 Hz), 4.80 (1H, ddd, CHO, J 3.6, 4.4, 7.2 Hz), 5.48 (1H, d, OH, J 4.8 Hz), 7.04 (1H, d, arom., J 8.0 Hz), 7.17 (1H, dd, arom., J 0.8, 7.6 Hz), 7.30 (1H, s, arom.), 11.60 (1H, bs, NH).

Step 2: 2,6-Lutidine (1.02 g, 9.5 mmol) was added to a solution of 53 (2.09 g, 9.5 mmol) in TBF (50 mL) at 0°0 C., followed by TBDMSOTf (2.51 g, 9.50 mmol) and the solution allowed to warm to room temperature. After 2 hours, a further aliquot of TBDMSOTf (1.25 g, 4.75 mmol) was added and the solution stirred for a further 1 hour. The mixture was diluted with EtOAc, washed with saturated NaHCO$_3$, 10% HCl, brine and dried (MgSO$_4$). The material was partially purified by chromatography (silica gel, 0–30% EtOAc in heptane) to yield 54 (3.20 g, quantitative)as a yellow oil:

m/z 449.24 (M+TBDMS+H$^+$)

$v_{max}$ 3227, 2102, 1771, 1260, 838 cm$^{-1}$

NMR $\delta_H$ (DMSO-d$_6$) 0.10 (3H, SICH$_3$), 0.10 (3H, s, SiCH$_3$), 0.87 (9H, s, Si$^t$Bu), 3.32 (2H, m, CH$_2$),4.97 (1H, dd, CHO, J 3.6, 6.8 Hz), 7.06 (1H, d, arom., J 7.6 Hz), 7.18 (1H, dd, arom., J 1.2 8.0 Hz), 7.29 (1H, s, arom.), 11.62 (1H, bs, NH).

Step 3: Compound 54 (3.20 g, 9.5 mmol assumed) and 10% Pd—C (400 mg) in MeOH (50 mL) were hydrogenated at 50 psi and 30° C. for 2 hours. The mixture was filtered through Kieselguhr, the filter cake was then washed with DMF (~300 mL), and these washings were concentrated to yield 55 (1.81 g, 62%) as an off-white solid:

m/z 309.18 (MH$^+$)

$v_{max}$ 3418, 1677, 1582, 1263 cm$^{-1}$

NMR $\delta_H$ (DMSO-d$_6$) 0.12 (3H, SICH$_3$), 0.05 (3H, s, SiCH$_3$), 0.85 (9H, s, Si$^t$Bu), 2.62 (1H, dd, CH$_2$, J 5.2, 6.4 Hz), 4.62 (1H, dd, CHO, J 5.2, 6.4 Hz), 7.01 (1H, d, arom., J 8.0 Hz), 7.06 (1H, dd, arom., J 1.6 8.0 Hz), 7.17 (1H, s, arom.).

Step 4: Compound 35 (1.69 g, 5.88 mmol), HBTU (2.29 g, 5.88 mmol) and DIPEA (3.03 g, 23.51 mmol) in DMF (25 mL) were stirred at room temperature for 10 minutes, then 55 (1.81 g, 5.88 mmol) was added, and the mixture stirred at room temperature for 4 hours. The solvent was removed and the mixture taken up in EtOAc, washed with saturated NaHCO$_3$, brine and dried (MgSO$_4$). The product was purified by chromatography (silica gel, 0–5% MeOH in CH$_2$Cl$_2$) to yield 56 (1.32 g, 42%) as a fawn colored foam:

m/z 542.30 (MH$^+$)

$v_{max}$ 3351, 1778, 1657, 1509 cm$^{-1}$ $^1$H-NMR (CDCl$_3$) $\delta_H$ 0.09 (3H, SICH$_3$), 0.08 (3H, s, SiCH$_3$), 0.94 (9H, s, Si$^t$Bu), 1.27 (2H, m, alkyl), 1.58 (3H, m, alkyl), 2.04 (1H, t, CH, J 11.2 Hz), 2.18 (1H, t, CH, J 10.8 Hz), 2.51 (2H, d, CH$_2$, J 6.8 Hz), 2.75 (2H, m, alkyl), 2.92 (2H, m, alkyl), 3.28 (1H, m, alkyl), 3.56 (1H, m, alkyl), 4.82 (1H, dd, CHO, J 4.4, 6.0 Hz), 6.91–7.00 (3H, m, arom.), 7.09 (3H, m, arom.), 7.22 (1H, s, arom.), 7.56 (1H, bm, CONH), 8.36 (1H, bs, NH).

Step 5: Compound 56 (1.32 g, 2.44 mmol) and Lawesson's reagent (493 mg, 1.22 mmol) in dioxane (10 mL) were stirred and heated to reflux for 1.5 hours. A further aliquot of Lawesson's reagent (493 mg, 1.22 mmol) was added and heating continued for 1 hour. The mixture was diluted with EtOAc, washed with saturated NaHCO$_3$, brine and dried (MgSO$_4$). The crude material was purified by chromatography (silica gel, 0–50% EtOAc/heptane) to give 57 (806 mg, 59%) as a cream colored oil which solidified on standing:

m/z 557.31 (MH$^+$)

$v_{max}$ 3250, 1776, 1509, 1259, 836 cm$^{-1}$ $^1$H-NMR (CDCl$_3$) $\delta_H$ 0.07 (3H, SICH$_3$), 0.07 (3H, s, SiCH$_3$), 0.90 (9H, s, Si$^t$Bu), 1.18 (2H, m, alkyl), 1.47–1.65 (3H, m, alkyl), 2.04 (1H, dt, CH, J 2.2, 11.6 Hz), 2.22 (1H, dt, CH, J 2.2, 11.6 Hz), 2.51 (2H, d, CH$_2$, J 6.8 Hz), 2.57 (1H, d, CHH, J 12.0 Hz), 2.72 (1H, d, CHH, J 12.0 Hz), 3.40 (2H, dd, CH$_2$, J 17.6, 25.2 Hz), 3.80 (1H, m, alkyl), 4.03 (1H, m, alkyl), 5.09 (1H, dd, CHO, J 4.0, 6.0 Hz), 6.98 (3H, m, arom.), 7.09 (2H, m, arom.), 7.16 (1H, d, arom., J 8.0 Hz), 7.29 (1H, s, arom.), 7.90 (1H, s, CONH), 9.56 (1H, bs, NH).

Step 6: Compound 57 (806 mg, 1.45 mmol) in THF (10 mL) was treated with TBAF (1 M in THF, 2.90 mL, 2.90 mmol) and stirred at room temperature for 4 hours. The mixture was diluted with EtOAc, washed with 10% citric acid, saturated NaHCO$_3$, brine and dried (MgSO$_4$). The product was purified by chromatography (silica gel, 0–2% MeOH/CH$_2$Cl$_2$) to give 58 as a fawn colored foam (348 mg, 64%):

m/z 444.19 (MH$^+$)

$v_{max}$ 3210, 1766, 1509 cm$^{-1}$ $^1$H-NMR (CDCl$_3$) $\delta_H$ 1.15 (2H, m, alkyl), 1.49–1.61 (3H, m, alkyl), 2.15 (2H, t, alkyl, J 12.0 Hz), 2.49 (2H, d, CH$_2$, J 7.2 Hz), 2.68 (2H, t, CH$_2$, J 12.4 Hz), 2.76 (1H, bs, OH), 3.44 (2H, dd, CH$_2$, J 18.0, 19.2 Hz), 3.76 (1H, dd, CHH, J 8.0, 14.0 Hz), 4.25 (1H, dd, CHH, J 2.8, 14.0 Hz), 5.13 (1H, dd, CHO, J 3.2, 7.2 Hz), 6.95–7.00 (2H, m, arom.), 7.03–7.09 (3H, m, arom.), 7.22 (1H, d, arom., J 8.4 Hz), 7.33 (1H, s, arom.), 9.69 (1H, bs, NH).

Step 7: Compound 58 (348 mg, 786 μmol) and Burgess reagent (187 mg, 786 μmol) in THF (10 mL) were stirred and heated to reflux for 4 hours. An aliquot of Burgess Reagent (37 g, 157 μmol) was added and heating continued for a further 2 hours. Diluted with EtOAc, washed with saturated NaHCO$_3$, brine and dried (MgSO$_4$). The product was purified by chromatography (silica gel, 0–2% MeOH/CH$_2$Cl$_2$) and then again using (silica gel, 0–75% EtOAc/heptane) to yield 6-{2-[4-(4-fluorobenzyl)piperidin-1-ylmethyl]-4,5-dihydrothiazol-5-yl}-3H-benzoxazol-2-one (98 mg, 29%) as a white solid:

m/z 426.26 (MH$^+$)

$v_{max}$ 3111, 1771, 1622, 1509, 1219 cm$^{-1}$ $^1$H-NMR (CDCl$_3$) $\delta_H$ 1.34 (2H, m, alkyl), 1.49 (1H, m, alkyl), 1.59 (2H, m alkyl), 2.06 (2H, dd, alkyl, J 9.6, 19.2 Hz), 2.50 (2H, d, CH$_2$, J 7.2 Hz), 2.93 (2H, dd, CH$_2$, J 10.8, 10.8 Hz), 3.39 (2H, dd, CH$_2$, J 16.2, 16.2 Hz), 4.37 (1H, dd, CHH, J 4.8, 15.6 Hz), 4.58 (1H, dd, CHH, J 9.2, 16.0 Hz), 4.87 (1H, dd, CHO, J 5.2, 9.2 Hz), 6.94 (3H, m, arom.), 7.06 (3H, m, arom.), 7.15 (1H, d, arom., J 1.2 Hz), 8.41 (1H, bs, NH).

General Methods for Examples 15–36

HCl salts were prepared by treatment of a MeOH solution of the amine with excess HCl in Et$_2$O (1 M). The salts were isolated either by filtration if they precipitated directly from the etherial solution, or by first removal of the solvent under reduced pressure, and then crystallization (Et$_2$O/MeOH).

Purity was determined by reversed phase HPLC by the following methods:

Method A: column: YMC J'Sphere C18, ODS-M80, 150× 4.6 mm, 4μ; solvent A: 0.1% H$_3$PO$_4$ in 95:5 H$_2$O/CH$_3$CN; solvent B: 0.1% H$_3$PO$_4$ in 95:5 CH$_3$CN/H$_2$O; gradient: 10–100% B over 15 minutes; flow: 1 mL min$^{-1}$; detection: 210 nm.

Method B: column: YMC J'Sphere C18, ODS-M80, 150× 4.6 mm, 4μ; solvent A: 0.1% H$_3$PO$_4$ in 95:5 H$_2$O/MeOH; solvent B: 0.1% H$_3$PO$_4$ in 95:5 MeOH/H$_2$O; gradient: 10–100% B over 15 minutes; flow: 1 mL min$^{-1}$; detection: 215 nm.

Method C: column: SYNERGI MAX-RP C12, 80 Å, 150× 4.6 mm, 4μ; solvent A: 95:5 H$_2$O/CH$_3$CN; solvent B: 95:5 CH$_3$CN/H$_2$O; gradient: 10–100% B over 15 minutes; flow: 1 mL min$^{-1}$; detection: 215 nm.

Method D: column: SYNERGI MAX-RP C12, 80 Å, 150× 4.6 mm, 4μ; solvent A: 95:5 H$_2$O/MeOH; solvent B: 95:5 MeOH/H$_2$O; gradient: 10–100% B over 15 minutes; flow: 1 mL min$^{-1}$; detection: 215 nm.

EXAMPLE 15

6-{5-[4-(4-Fluorobenzyl)piperidin-1-ylmethyl] isoxazol-3-yl}-3H-benzoxazol-2-one

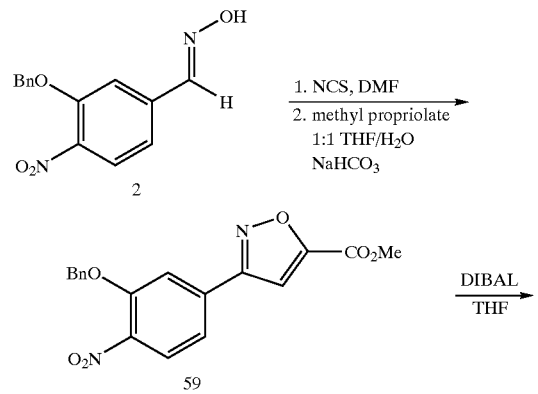

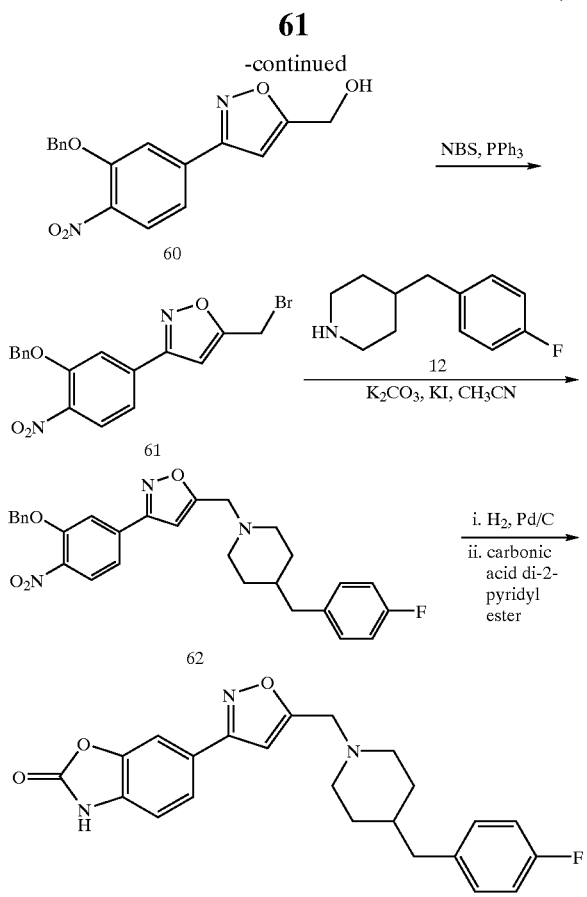

Step 1: A solution of oxime of formula 2 (8.41 g, 30.9 mmol) and freshly crystallized (benzene) N-chlorosuccinimide (4.12 g, 30.9 mmol) in DMF (30 mL) was stirred at room temperature for 1 hour. The reaction was partitioned between EtOAc and H$_2$O. The organic layer was washed with saturated NaCl, dried (Na$_2$SO$_4$), and concentrated under reduced pressure. The residue was dissolved in 1:1 THF/H$_2$O (30 mL). Sodium bicarbonate (7.80 g, 92.7 mmol) and methyl propiolate (2.4 mL, 40.2 mmol) were added, and the reaction mixture was stirred overnight. The reaction was diluted with EtOAc and the organic layer was dried (Na$_2$SO$_4$), and concentrated under reduced pressure. Ester of formula 59 (7.21 g, 66%) was isolated as a yellow solid following trituration with EtOAc/hexanes:

$^1$H NMR (500 MHz, CDCl$_3$): δ 7.96 (d, J 9 Hz, 1H), 7.70 (d, J 2 Hz, 1H), 7.48 (dd, J 8, 1 Hz, 2H), 7.42–7.39 (m, 3H), 7.36–7.33 (m, 1H), 7.25 (s, 1H), 5.32 (s, 2H), 4.01 (s, 3H).

Step 2: To an ice-cold solution of the ester of formula 59 (7.21 g, 20.3 mmol) in THF (100 mL) was added diisobutylaluminum hydride (51.0 mL of a 1.0 M solution in cyclohexane, 51.0 mmol). After 1 hour, the reaction was diluted with MeOH (2 mL) and a saturated solution of Rochelle's salt (50 mL) was added. After stirring briefly, the solution became gel like. The gel dissolved upon addition of EtOAc (150 mL) and the solution was stirred for several hours. The organic layer was washed with H$_2$O and saturated NaCl, dried (Na$_2$SO$_4$) and concentrated under reduced pressure to give the alcohol of formula 60 (6.57 g, 99%) as a yellow solid:

$^1$H NMR (300 MHz, CDCl$_3$): δ 7.96 (d, J 9 Hz, 1H), 7.70 (d, J 2 Hz, 1H), 7.49 (dd, J 8, 1 Hz, 2H), 7.42–7.30 (m, 4H), 6.60 (s, 1H), 5.32 (s, 2H), 4.85 (s, 2H), 2.15 (s, 1H).

Step 3: Triphenylphosphine (6.56 g, 25.0 mmol) and N-bromosuccinimide (4.45 g, 25.0 mmol) were added to an ice-cold solution of alcohol of formula 60 (6.53 g, 20.0 mmol) in THF (50 mL) and the solution was stirred for 1 hour. The mixture was partitioned between EtOAc and saturated NaHCO$_3$. The organic layer was washed with saturated NaCl, dried (Na$_2$SO$_4$), and concentrated under reduced pressure. Purification by chromatography (silica gel, 1:4 hexanes/EtOAc) gave bromide of formula 61 (6.88 g, 88%):

$^1$H NMR (500 MHz, CDCl$_3$): δ 7.94 (d, J 8 Hz, 1H), 7.67 (d, J 2 Hz, 1H), 7.49 (dd, J 8, 1 Hz, 2H), 7.42–7.34 (m, 4H), 6.62 (s, 1H), 5.30 (s, 2H), 4.51 (s, 2H).

Step 4: A solution of bromide of formula 61 (3.42 g, 8.79 mmol), amine of formula 12 (2.01 g, 8.79 mmol), K$_2$CO$_3$ (2.41 g, 17.5 mmol), KI (146 mg, 0.879 mmol), and LiBr (200 mg, 2.30 mmol) in CH$_3$CN (30 mL) was stirred at 50° C. overnight. The reaction solvent was removed under reduced pressure. The residue was partitioned between EtOAc and water. The organic layer was washed with saturated NaCl, dried (Na$_2$SO$_4$), and concentrated under reduced pressure. Purification by chromatography (silica gel, 99:1 to 95:5 CH$_2$Cl$_2$/MeOH) gave compound of formula 62 (3.26 g, 74%) as a pale yellow oil:

$^1$H NMR (300 MHz, CDCl$_3$): δ 7.94 (d, J 8 Hz, 1H), 7.67 (d, J 2 Hz, 1H), 7.49 (dd, J 8, 1 Hz, 2H), 7.42–7.30 (m, 4H), 7.08 (dd, J 8, 7 Hz, 2H), 6.95 (dd, J 8, 7 Hz, 2H), 6.50 (s, 1H), 5.32 (s, 2H), 3.73 (s, 2H), 2.92 (d, J 12 Hz, 2H), 2.51 (d, J 7 Hz, 2H), 2.08 (ddd, J 12, 12, 2 Hz, 2H), 1.67–1.25 (m, 5H).

Step 5: Palladium on charcoal (10% Pd, 200 mg) was added to a solution of compound of formula 62 (2.42 g, 4.80 mmol) in THF (100 mL), and the mixture was shaken under an atmosphere of H$_2$ (g) at 50 psi for 4 hours. The reaction mixture was rapidly filtered through CELITE under reduced pressure into a reaction flask. The flask was capped with a septum and purged with nitrogen. To the clear solution was added carbonic acid di-2-pyridyl ester (1.15 g, 5.28 mmol) and Et$_3$N (1.50 mL, 10.56 mmol), and the solution was refluxed for 6 hours. The solvent was removed under reduced pressure. Purification by chromatography (silica gel, 99:1 to 95:5 CH$_2$Cl$_2$/MeOH) and subsequent crystallization from hot EtOH gave 6-{5-[4-(4-fluorobenzyl)piperidin-1-ylmethyl]isoxazol-3-yl}-3H-benzoxazol-2-one (665 mg, 34%) as an off-white solid:

mp 237–244° C.

IR (KBr): 2934, 2825, 1775 cm$^{-1}$;

$^1$H NMR (300 MHz, DMSO-d$_6$): δ 11.87 (s, 1H), 7.78 (d, J 1 Hz, 1H), 7.70 (dd, J 8, 1 Hz, 1 H), 7.20–7.15 (m, 3H), 7.07 (dd, J 8, 7 Hz, 2H), 6.93 (s, 1H), 3.66 (s, 2H), 2.84 (d, J 11 Hz, 2H), 2.47 (d, J 6 Hz, 2H), 1.99 (dd, J 11, 10 Hz, 2H), 1.54–1.45 (m, 3H), 1.25–1.18 (m, 2H); ESI-MS (m/z): 408 [M+H]$^+$; HPLC: method A, 5.91 minutes (>99%); method B, 11.23 minutes(>99%); Anal. Calcd for C$_{23}$H$_{22}$FN$_3$O$_3$: C, 67.80; H, 5.44; N, 10.31. Found: C, 67.67; H, 5.52; N, 10.11.

EXAMPLE 16

6-{5-[4-(4-Fluorobenzyl)piperidin-1-yl]methyl}-4,5-dihydroisoxazol-3-yl}-3H-benzothiazol-2-one

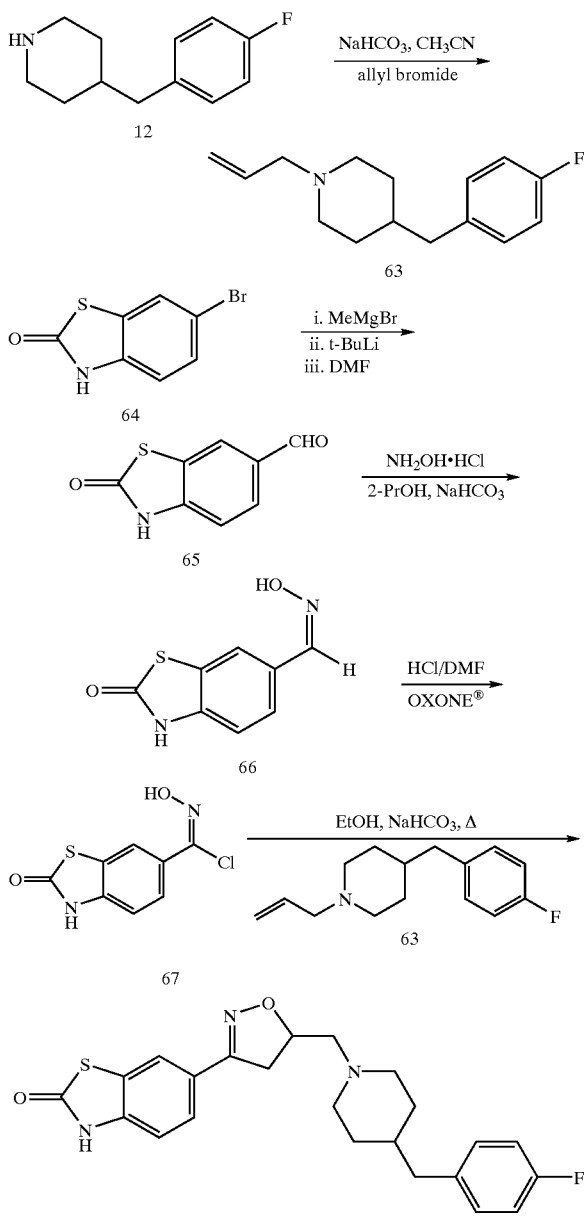

Step 1: 4-(4-Fluorobenzyl)piperidine hydrochloride 12 (2.55 g, 11.1 mmol) and NaHCO$_3$ (2.3 g, 27.7 mmol) were added to a solution of allyl bromide in CH$_3$CN. The mixture was warmed to 40° C. for 3 hours. The solvent was removed under reduced pressure and the residue was partitioned between EtOAc and water. The organic layer was washed with saturated NaCl, dried (Na$_2$SO$_4$), filtered, and the solvent removed under reduced pressure. Purification by flash chromatography (silica gel, 95:5 to 9:1 CH$_2$Cl$_2$/MeOH) gave alkene of formula 63 (1.13 g, 44%) as an oil:

$^1$H NMR (500 MHz, DMSO-d$_6$): δ 7.18–7.14 (m, 2H), 7.08–7.03 (m, 2H), 5.81–5.73 (m, 1H), 5.11 (dd, J 17, 2 Hz, 1H), 5.06 (dd, J 11, 2 Hz, 1H), 2.87 (d, J 6 Hz, 2H), 2.77 (d, J 12 Hz, 2H), 2.47 (d, J 7 Hz, 2H), 1.79 (dt, J 12, 2 Hz, 2H), 1.50–1.39 (m, 3H), 1.15 (tt, J 13, 3 Hz, 2H).

Step 2: To a −78° C. solution of bromide of formula 64 (5.02 g, 21.8 mmol) in THF (50 mL) was added MeMgBr (8.0 mL of a 3.0 M solution in diethyl ether, 24.0 mmol). After 30 minutes, anhydrous THF (170 mL) was added at a rate that maintained the internal reaction temperature below a threshold of −50° C. After the solution returned to −78° C., tert-butyl lithium (50 mL of a 1.7 M solution in pentane, 85 mmol) was added. After 10 minutes, DMF (10 mL, 130 mmol) was added to the yellow mixture, and the cold bath was removed. After 1 hour, the reaction was quenched with water, and the THF was removed under reduced pressure. The residue was partitioned between EtOAc and 1N HCl. The aqueous layer was extracted with three portions of EtOAc. The organic extracts were combined and washed with saturated NaCl, dried (Na$_2$SO$_4$), filtered, and concentrated under reduced pressure to give aldehyde of formula 65 (3.74 g, 96%) as a white solid:

$^1$H NMR (500 MHz, DMSO-d$_6$): δ 12.39 (s, 1H), 9.90 (s, 1H), 8.17 (d, J 1 Hz, 1H), 7.85 (dd, J 8, 1 Hz, 1H), 7.30 (d, J 8 Hz, 1H).

Step 3: A mixture of aldehyde of formula 65 (3.74 g, 20.8 mmol), hydroxylamine hydrochloride (1.60 g, 22.9 mmol), and sodium bicarbonate (2.18 g, 26.0 mmol) in 2-PrOH (75 mL) was heated to 75° C. for 3 hours. After stirring overnight at room temperature, the mixture was diluted with 2-PrOH (200 mL). The solution was filtered and concentrated under reduced pressure to give oxime of formula 66 (4.00 g, 99%), as a white solid:

$^1$H NMR (300 MHz, DMSO-d$_6$): δ 11.96 (s, 1H), 11.15 (s, 1H), 8.10 (s, 1H), 7.79 (d, J 1 Hz, 1H), 7.52 (dd, J 8, 1 Hz, 1H), 7.14 (d, J 8 Hz, 1H).

Step 4: A mixture of oxime of formula 66 (4.00 g, 20.6 mmol) and OXONE® (13.9 g, 22.6 mmol) was stirred in a solution of HCl in DMF (43 mL of a 0.53 M, 22.6 mmol) for 3.5 hours. The reaction mixture was partitioned between EtOAc and 1N HCl. The organic layer was washed with saturated NaCl, dried (Na$_2$SO$_4$), filtered, and concentrated under reduced pressure. The yellow solid was triturated with 1:1 EtOAc/hexanes and filtered to give compound of formula 67 (3.53 g, 75%):

$^1$H NMR (300 MHz, DMSO-d$_6$): δ 12.33 (s, 1H), 12.15 (s, 1H), 8.03 (d, J 2 Hz, 1H), 7.73 (dd, J 8, 2 Hz, 1H), 7.20 (d, J 8 Hz, 1H).

Step 5: Coupling of compound of formula 67 and alkene of formula 63 following the procedure described in Example 17, Step 5, followed by conversion to the HCl salt, gave 6-{5-[4-(4-fluorobenzyl)piperidin-1-yl]methyl)-4,5-dihydroisoxazol-3-yl}-3H-benzothiazol-2-one (484 mg, 41%):

mp 271–276 ° C.

IR (KBr): 3422, 2932, 1686, 1670, 1603 cm$^{-1}$ $^1$H NMR (500 MHz, DMSO-d$_6$): δ 12.19 (s, 1H), 10.58 (s, 1H), 7.88 (s, 1H), 7.60 (d, J 8 Hz, 1H), 7.23–7.20 (m, 3H), 7.11 (dd, J 9, 8 Hz, 2H), 5.30–5.24 (m, 1H), 3.66 (dd, J 17, 11 Hz, 1H), 3.58 (d, J 12 Hz, 1H), 3.48 (d, J 11 Hz, 1H), 3.34–3.17 (m, 3H), 2.95 (m, 2H), 2.53 (d, J 5 Hz, 2H), 1.75–1.74 (m, 3H), 1.64–1.54 (m, 2H); ESI-MS (m/z): 426 [M+H]$^+$; HPLC: method A, 6.05 minutes (>99%); method B, 11.48 minutes (>99%); Anal. Calcd for C$_{23}$H$_{24}$FN$_3$O$_2$S.HCl0.25H$_2$O: C, 59.22; H, 5.51; N, 9.01. Found: C, 59.37; H, 5.38; N, 8.82.

EXAMPLE 17

6-[5-(4-Benzyl-4-hydroxypiperidin-1-ylmethyl)-4,5-dihydroisoxazol-3-yl]-3H-benzoxazol-2-one

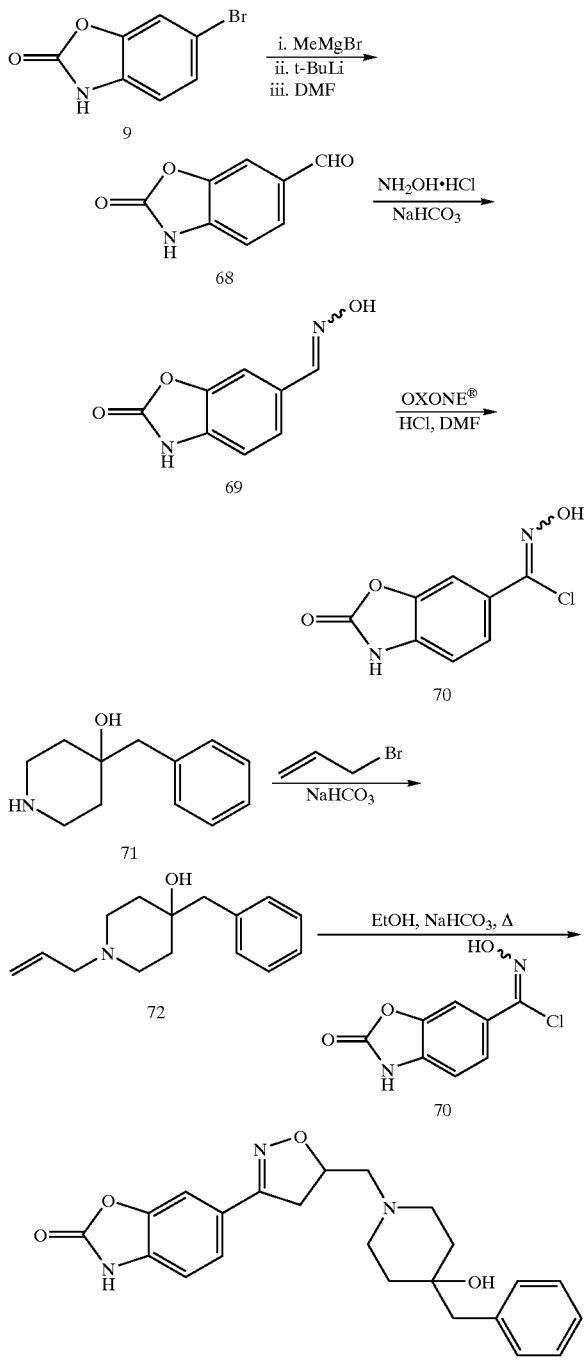

Step 1: To a −78° C. solution of 9 (20.0 g, 93.4 mmol) in THF (180 mL) was added MeMgBr (34.5 mL of a 3.0 M solution in diethyl ether, 103 mmol). After 45 minutes, anhydrous THF (750 mL) was added at a rate that maintained the internal reaction temperature below a threshold of −50° C. After the solution returned to −78° C., tert-butyl lithium (200 mL of a 1.7 M solution in pentane, 118 mmol) was added via a dropping funnel. After 15 minutes, DMF (44 mL, 561 mmol) was added to the yellow mixture, and the cold bath was removed. After 2 hours, the reaction was quenched with water and the THF removed under reduced pressure. The residue was partitioned between EtOAc and 1N HCl. The aqueous layer was extracted with EtOAc (2×). The combined organic extracts were washed with sat. NaCl, dried (Na$_2$SO$_4$), and concentrated under reduced pressure. The crude solid was dissolved in hot EtOAc and hexane was added to the solution until a precipitate formed. The precipitate was collected by filtration to give 68 (12.44 g, 81%) as an off-white solid:

$^1$H NMR (500 MHz, DMSO-d$_6$): δ 12.13 (s, 1H), 9.92 (s, 1H), 7.78 (d, J 8 Hz, 1H), 7.75 (s, 1H), 7.29 (d, J 8 Hz, 1H).

Step 2: A mixture of aldehyde 68 (10.0 g, 61.3 mmol), hydroxylamine hydrochloride (4.26 g, 61.3 mmol), and sodium bicarbonate (5.15 g, 61.3 mmol) in 2-PrOH (75 mL) was heated to 40° C. for 3 hours. After cooling to ambient temperature, the mixture was diluted with 2-PrOH and filtered. Concentration under reduced pressure gave oxime 69 (11.6 g, 100%), as a white solid:

$^1$H NMR (300 MHz, DMSO-d$_6$): δ 11.82 (s, 1H), 11.15 (s, 1H), 8.14 (s, 1H), 7.49 (s, 1H), 7.39 (d, J 8 Hz, 1H), 7.12 (d, J 8 Hz, 1H).

Step 3: A mixture of oxime 69 (11.6 g, 61.3 mmol) and OXONE® (41.4 g, 67.4 mmol) was stirred in HCl (62 mL of a 1.09 M solution in DMF, 67.4 mmol) for 2.5 hours. The reaction mixture was partitioned between EtOAc and water. The aqueous layer was extracted with EtOAc (2×). The combined organic extracts were washed with sat. NaCl, dried (Na$_2$SO$_4$), and concentrated under reduced pressure. Trituration of the yellow solid with EtOAc gave 70 (7.03 g, 54%). The washings were concentrated under reduced pressure and the residue triturated with 3:1 EtOAc/hexanes to give a second crop of 70 (2.34 g, 18%):

$^1$H NMR (300 MHz, DMSO-d$_6$): δ 12.33 (s, 1H), 11.93 (s, 1H), 7.63 (s, 1H), 7.60 (d, J 8 Hz, 1H), 7.18 (d, J 8 Hz, 1H).

Step 4: Alkene of formula 72 was prepared following the procedure described below for alkene of formula 63 in Example 16, Step 1, to give 420 mg, (14%): $^1$H NMR (500 MHz, CDCl$_3$): δ 7.30 (dd, J 8, 7 Hz, 2H), 7.24–7.23 (m, 1H), 7.19 (d, J 7 Hz, 2H), 5.91–5.83 (m, 1H), 5.17 (dd, J 17, 2 Hz, 1H), 5.12 (dd, J 10, 2 Hz, 1H), 3.01 (d, J 6 Hz, 2H), 2.75 (s, 2H), 2.67–2.63 (m, 2H), 2.28 (dt, J 10, 2 Hz, 2H), 1.74 (dt, J 13, 4 Hz, 2H), 1.53 (dd, J 14, 2 Hz, 2H), 1.17 (s, 1H).

Step 5: A solution of alkene of formula 72 (420 mg, 1.81 mmol) in EtOH (10 mL) was added to a mixture of NaHCO$_3$ and compound of formula 70 (425 mg, 2.0 mmol). The mixture was heated to reflux for 2 hours. Methanol and CH$_2$Cl$_2$ were added to dissolve an organic precipitate that had formed during the course of the reaction. Silica gel was added and the solvent was removed under reduced pressure. Purification by flash chromatography (silica gel, 89:10:1 CH$_2$Cl$_2$/MeOH/NH$_4$OH), trituration of the isolated solid with MeOH, and conversion to the HCl salt gave IUPAC: 6-[5-(4-benzyl-4-hydroxypiperidin-1-ylmethyl)-4,5-dihydroisoxazol-3-yl]-3H-benzoxazol-2-one (425 mg, 52%) as a white solid:

mp 166–170° C.

IR (KBr): 3387, 2958, 1773 cm$^{-1}$ $^1$H NMR (500 MHz, DMSO-d$_6$): δ 12.01 (s, 1H), 10.20 (s, 1H), 7.57 (s, 1H), 7.47 (d, J 8 Hz, 1H), 7.30 (dd, J 8, 7 Hz, 2H), 7.24 (d, J 7 Hz, 2H), 7.14 (d, J 8 Hz, 2H), 5.23 (m, 1H), 4.82 (s, 1H), 3.66 (dd, J 17, 11 Hz, 1H), 3.37–3.33 (m, 4H), 3.19–3.16 (m, 2H), 2.74 (s, 2H), 1.93–1.85 (m, 2H), 1.61 (d, J 15 Hz, 2H); ESI-MS (m/z): 408 [M+H]$^+$

HPLC: method A, 4.14 minutes (98.2%); method B, 9.92 minutes (>99%); Anal. Calcd for C$_{23}$H$_{25}$N$_3$O$_4$·1.125 H$_2$O: C, 59.22; H, 6.08; N, 9.01. Found: C, 59.34; H, 5.94; N, 8.96.

EXAMPLE 18

6-{5-[4-(4-Fluorobenzyl)piperidine-1-carbonyl]-4,5-dihydroisoxazol-3-yl}-3H-benzoxazol-2-one

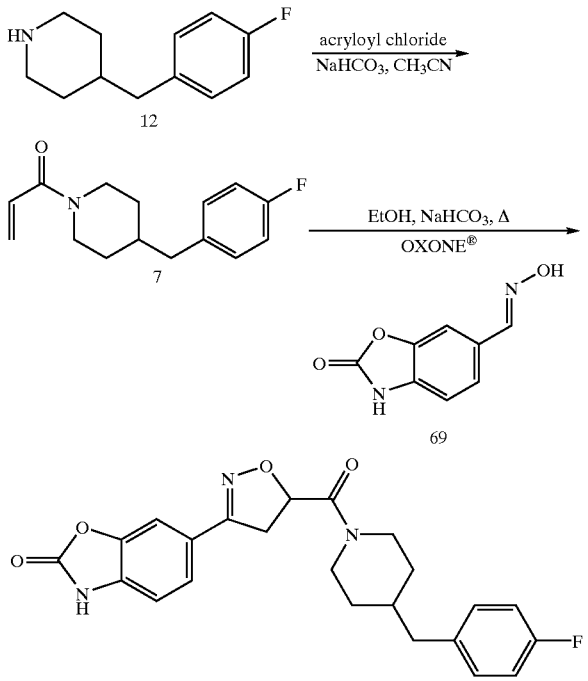

Step 1: A mixture of 4-(4-fluorobenzyl)piperidine hydrochloride 12 (2.09 g, 9.09 mmol), NaHCO$_3$ (765 mg, 9.09 mmol) and acryloyl chloride (815 μL, 10.0 mmol) in CH$_3$CN (15 mL) was stirred at ambient temperature for 6 hours. The solvent was removed under reduced pressure, and the residue was partitioned between EtOAc and water. The organic layer was washed with sat. NaHCO$_3$ and sat. NaCl, dried (Na$_2$SO$_4$), and concentrated under reduced pressure. Purification by flash chromatography (silica, 99:1 to 95:5 CH$_2$Cl$_2$/MeOH) gave 73 (730 mg, 33%) as an oil:

$^1$H NMR (500 MHz, CDCl$_3$): δ 7.09 (dd, J 9, 8 Hz, 2H), 6.96 (dd, J 9, 8 Hz, 2H), 6.56 (dd, J 17, 11 Hz, 1H), 6.25 (dd, J 17, 1 Hz, 1H), 5.65 (dd, J 11, 1 Hz, 1H), 4.65–4.58 (m, 1H), 3.95 (d, J 13 Hz, 1H), 2.98–2.94 (m, 1H), 2.64–2.45 (m, 3H) 1.78–1.70 (m, 3H), 1.29–1.16 (m, 2H).

Step 2: A mixture of oxime 69 (525 mg, 2.95 mmol) and OXONE® (1.90 g, 3.10 mmol) was stirred in HCl (2.85 mL of a 1.09 M solution in DMF, 3.10 mmol) for 1.5 hours. The reaction mixture was partitioned between EtOAc and 1N HCl. The organic layer was washed with sat. NaCl, dried (Na$_2$SO$_4$), and concentrated under reduced pressure. The residue was combined with NaHCO$_3$ (750 mg, 8.85 mmol) and a solution of amide 73 (730 mg, 2.95 mmol) in 1:1 THF/H$_2$O (10 mL) was added. The reaction mixture was stirred for 24 hours at ambient temperature. The solvent was removed under reduced pressure and the residue was partitioned between EtOAc and 1N HCl. The organic layer was washed with sat. NaCl, dried (Na$_2$SO$_4$), and concentrated under reduced pressure. Purification by flash chromatography (silica, 5:2 hexanes/EtOAc to 9:1 CH$_2$Cl$_2$/MeOH) followed by trituration with 3:1 hexanes/EtOAc gave 6-{5-[4-(4-fluorobenzyl)piperidine-1-carbonyl]4,5-dihydroisoxazol-3-yl}-3H-benzoxazol-2-one (507 mg, 40%):

mp 210–213° C.

IR (KBr): 3193, 2931, 1779, 1632 cm$^{-1}$ $^1$H NMR (500 MHz, DMSO-d$_6$): δ 11.84 (s, 1H), 7.59 (s, 1H), 7.50 (d, J 8 Hz, 1H), 7.23–7.20 (m, 2H), 7.16 (d, J 8 Hz, 1H), 7.10 (dd, J 9, 8 Hz, 2H), 5.58–5.51 (m, 1H), 4.35–4.30 (m, 1H), 4.03 (d, J 14 Hz, 1H), 3.90–3.77 (m, 1H), 3.54–3.47 (m, 1H), 3.09–3.00 (m, 1H), 2.64–2.58 (m, 1H), 2.54 (d, J 7 Hz, 2H), 1.79 (m, 1H), 1.68–1.58 (m, 2H), 1.24–1.16 (m, 1H), 1.08–0.97 (m, 1H)

ESI-MS (m/z): 424 [M+H]$^+$

HPLC: method A, 10.06 min (98.6%); Anal. Calcd for C$_{23}$H$_{22}$FN$_3$O$_4$: C, 65.24; H, 5.24; N, 9.92. Found: C, 65.03; H, 5.20; N, 9.87.

EXAMPLE 19

6-(5-{2-[4-(4-Fluorobenzyl)piperidin-1-yl]ethyl}-4,5-dihydroisoxazol-3-yl)-3H-benzoxazol-2-one

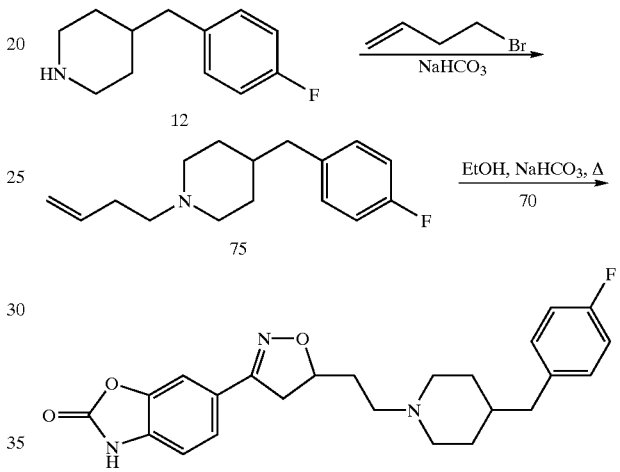

Step 1: Coupling of amine 12 (4.00 g, 17.4 mmol) with 4-bromo-1-butene (3.53 mL, 34.8 mmol) following the procedure described in Example 16, Step 1, followed by conversion to the HCl salt gave alkene 75 (3.57 g, 72%):

$^1$H NMR (500 MHz, DMSO-d$_6$): δ 10.52 (s, 1H), 7.23–7.20 (m, 2H), 7.13–7.07 (m, 2H), 5.83–5.72 (m, 1H), 5.16 (dd, J 17, 2 Hz, 1H), 5.09 (dd, J 10, 2 Hz, 1H), 3.43–3.38 (m, 2H), 3.18–3.14 (m, 1H), 3.04–3.00 (m, 2H), 2.85–2.78 (m, 2H), 2.52–2.47 (m, 3H), 1.80–1.68 (m, 3H), 1.59–1.51(m, 2H).

Step 2: Coupling of 70 (156 mg, 0.734 mmol) and alkene 75 (207 mg, 0.734 mmol) following the procedure described in Example 17, Step 5, followed by conversion to the HCl salt, gave 6-(5-{2-[4-(4-fluorobenzyl)piperidin-1-yl]ethyl}-4,5-dihydroisoxazol-3-yl)-3H-benzoxazol-2-one (200 mg, 58%):

mp 254–258° C.

IR (KBr): 3448, 2934, 2713, 1774 cm$^{-1}$ $^1$H NMR (500 MHz, DMSO-d$_6$): δ 11.90 (s, 1H), 10.09 (s, 1H), 7.55 (s, 1H), 7.46 (d, J 8 Hz, 1H), 7.21 (dd, J 9, 8 Hz, 2H), 7.16 (d, J 8 Hz, 1H), 7.11 (dd, J 9, 8 Hz, 2H), 4.79–4.73 (m, 1H), 3.54 (dd, J 17, 11 Hz, 1H), 3.45 (d, J 11 Hz, 2H), 3.18–3.09 (m, 4H), 2.83 (m, 2H), 2.53–2.49 (m, 2H), 2.06 (dd, J 15, 8 Hz, 2H), 1.73–1.70 (m, 2H), 1.52–1.48 (m, 2H)

ESI-MS (m/z): 424 [M+H]$^+$

HPLC: method A, 5.69 min (98.0%); method B, 10.96 min (98.4%); Anal. Calcd for C$_{24}$H$_{26}$FN$_3$O$_3$.HCl.0.5H$_2$O: C, 61.47; H, 6.02; N, 8.96. Found: C, 61.59; H, 6.02; N, 9.87.

EXAMPLE 20

6-{5-[4-(4-Fluorobenzyl)-4-hydroxypiperidin-1-ylmethyl]-4,5-dihydroisoxazol-3-yl}-3H-benzoxazol-2-one

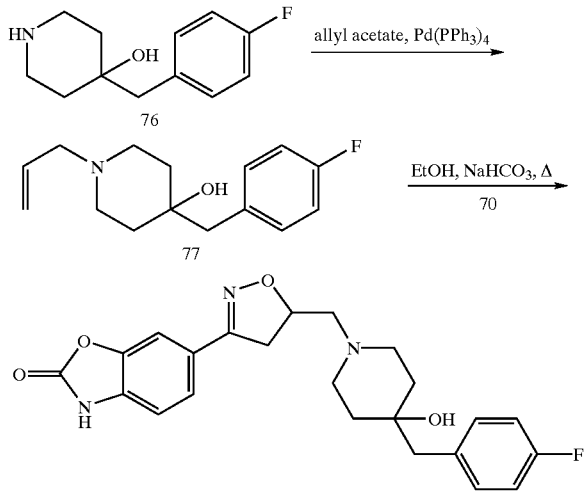

Step 1: To a suspension of the formate salt of amine 76 (14.3 g, 43.4 mmol) in toluene (225 mL) was added allyl acetate (5.2 mL, 47.7 mmol) and Et$_3$N (12.1 mL, 86.8 mmol). Solubility of the amine was problematic. Addition of pyridine (20 mL) and then MeOH (40 mL) resulted in a homogenous solution. The solution was deoxygenated with an argon sparge for 15 minutes, then palladium tetrakis (triphenylphosphine)palladium(0) (500 mg, 0.434 mmol) was added. The reaction mixture was heated to 100° C. in an oil bath for 1 hour and then cooled to ambient temperature. The mixture was filtered and the solution concentrated under reduced pressure. Purification by chromatography (silica, 95:5 to 9:1 CH$_2$Cl$_2$/MeOH) gave 77 (7.15 g, 70%) as a clear oil:

$^1$H NMR (500 MHz, CDCl$_3$): δ 7.17 (dd, J 9, 8 Hz, 2H), 7.02 (dd, J 9, 8 Hz, 2H), 6.23–6.09 (m, 1H), 5.53–5.43 (m, 2H), 3.54 (d, J 7 Hz, 2H), 3.31–3.27 (m, 2H), 3.01 (br. t, J 11 Hz, 2H), 2.83 (s, 2H), 2.37 (dt, J 13, 4 Hz, 2H), 2.06 (s, 1H), 1.71 (br. d, J 13 Hz, 2H).

Step 2: Coupling of 70 (978 mg, 4.16 mmol) and alkene 77 (975 mg, 4.57 mmol) following the procedure described in Example 17, Step 5, followed by conversion to the HCl salt, gave 6-{5-[4-(4-fluorobenzyl)-4-hydroxypiperidin-1-ylmethyl]-4,5-dihydroisoxazol-3-yl}-3H-benzoxazol-2-one (840 mg, 43%):

mp 195–204° C.

IR (KBr): 3380, 2958, 1770, cm$^{-1}$ $^1$H NMR (500 MHz, CD$_3$OD): δ 7.58 (s, 1H), 7.52 (d, J 8 Hz, 1H), 7.29–7.24 (m, 2H), 7.15 (dd, J 8, 2 Hz, 1H), 7.06–7.00 (m, 2H), 5.28–5.23 (m, 1H), 3.71 (dd, J 17, 11 Hz, 1H), 3.52–3.20 (m, 6H), 2.83 (s, 2H), 2.03–1.90 (m 2H), 1.79–1.70 (m, 2H), 1.18 (dt, J 7, 2 Hz, 1H)

APCI-MS (m/z): 426 [M+H]$^+$

HPLC: method A, 5.37 min (96.4%); method B, 10.38 min (98.3%); Anal. Calcd for C$_{23}$H$_{24}$FN$_3$O$_4$.HCl.0.5H$_2$O: C, 58.66; H, 5.56; N, 8.92. Found: C, 58.61; H, 5.60; N, 8.40.

EXAMPLE 21

6-{5-[4-(4-Fluorobenzyl)piperidin-1-ylmethyl]-5-methyl-4,5-dihydroisoxazol-3-yl}-3H-benzoxazol-2-one

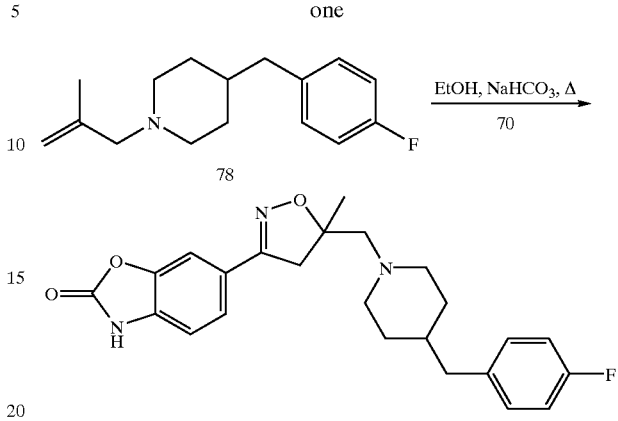

Step 1: A mixture of 4-(4-fluorobenzyl)piperidine hydrochloride (12) (3.05 g, 13.2 mmol) and NaHCO$_3$ (2.76 g, 32.8 mmol) in CH$_3$CN (50 mL) was heated to reflux for 30 minutes. After cooling to ambient temperature, methallyl bromide (1.7 mL, 17 mmol) was added, and the mixture was heated to reflux for 2 hours. The reaction mixture was filtered and concentrated under reduced pressure. Purification by flash chromatography (silica, 98:2 to 9:1 CH$_2$Cl$_2$/MeOH) gave 78 (2.67 g, 81%) as an oil:

$^1$H NMR (300 MHz, DMSO-d$_6$): δ 7.21–7.16 (m, 2H), 7.11–7.05 (m, 2H), 4.81 (m, 2H), 2.75–2.70 (m, 4H), 2.49 (m, 2H), 1.72 (m, 2H), 1.65 (s, 3H), 1.51–1.48 (m, 3H), 1.17–1.13 (m, 2H).

Step 2: Coupling of 70 (610 mg, 2.87 mmol) and alkene 78 (644 mg, 2.60 mmol) following the procedure described in Example 17, Step 5, gave 6-{5-[4-(4-fluorobenzyl)piperidin-1-ylmethyl]-5-methyl-4,5-dihydroisoxazol-3-yl}-3H-benzoxazol-2-one (299 mg, 26%) as a white solid: mp 82–86° C.

IR (KBr): 2925, 1774 cm$^{-1}$ $^1$H NMR (500 MHz, DMSO-d$_6$): δ 11.79 (s, 1H), 7.54 (d, J 1 Hz, 1H), 7.43 (dd, J 8, 1 Hz, 1H), 7.17–712 (m, 3H), 7.05 (dd, J 9, 9 Hz, 2H), 3.38 (d, J 17 Hz, 1H), 3.17 (s, 2H), 3.07 (d, J 17 Hz, 1H), 2.90–2.88 (m, 2H), 2.44 (d, J 7 Hz, 2H), 207–1.97 (m, 2H), 1.49–1.36 (m, 3H), 1.29 (s, 3H), 1.20–1.06 (m, 2H)

APCI-MS (m/z): 424 [M+H]$^+$

HPLC: method A, 6.57 min (97.8%); method B, 11.89 min (96.5%); Anal. Calcd for C$_{24}$H$_{26}$FN$_3$O$_3$.0.75H$_2$O: C, 65.96; H, 6.34; N, 9.62. Found: C, 66.03; H, 6.62; N, 9.25.

EXAMPLE 22

5-[4-(4-Fluorobenzyl)piperidin-1-ylmethyl]-3-(2-oxo-2,3-dihydrobenzoxazol-6-yl)-4,5-dihydroisoxazole-5-carboxylic acid

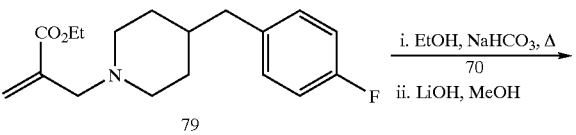

-continued

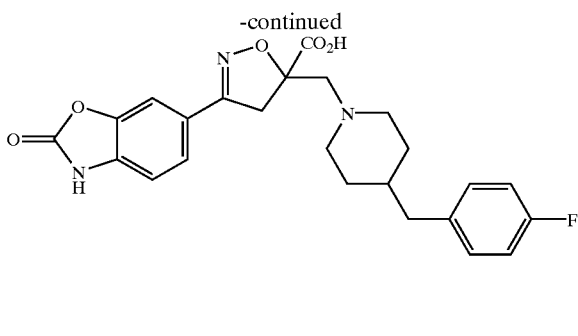

Step 1: To a suspension of the hydrochloride salt of amine 12 (2.06 g, 8.96 mmol) in toluene (50 mL) was added 2-acetoxymethylacrylic acid ethyl ester (1.70 g, 9.86 mmol) and Et$_3$N (1.37 mL, 9.86 mmol). The solution was deoxygenated with an argon sparge for 10 minutes, then palladium tetrakis(triphenylphosphine)-palladium(0) (260 mg, 0.224) was added. The reaction mixture was heated to 100° C. in an oil bath for 1 hour, and then cooled to ambient temperature. The mixture was filtered and then concentrated under reduced pressure. Purification by chromatography (silica, 95:5 to 9:1 CH$_2$Cl$_2$/MeOH) gave a yellow oil. The oil was dissolved in 3:1 EtOAc/hexanes and then acidified with 1N HCl/Et$_2$O to give alkene 79 (7.15 g, 70%) as a white solid:

$^1$H NMR (500 MHz, DMSO-d$_6$): δ 12.44 (s, 1H), 7.07 (dd, J 8, 8 Hz, 2H), 6.96 (dd, J 8, 8 Hz, 2H), 6.89 (s, 1H), 6.84 (s, 1H), 4.25 (q, J 7 Hz, 2H), 3.87 (d, J 5 Hz, 2H), 3.47 (br. d, J 12 Hz, 2H), 2.66–2.62 (m, 2H), 2.60 (d, J 7 Hz, 2H), 2.11–2.03 (m, 2H), 1.79 (br. d, J 14 Hz, 2H), 1.69–1.63 (m, 1H), 1.31 (t, J 7 Hz, 3H).

Step 2: Coupling of 70 (600 mg, 2.82 mmol) and alkene 79 (875 mg, 2.56 mmol) following the procedure described in Example 17, Step 5, gave the ester as an impure solid. The crude ester was saponified with excess LiOH in 1:1 MeOH/THF (15 mL). After stirring overnight, the reaction solvent was removed under reduced pressure. Purification by chromatography (silica, 89:10:1 to 79:20:1 CH$_2$Cl$_2$/MeOH/AcOH) followed by trituration with MeOH gave 5-[4-(4-fluorobenzyl)piperidin-1-ylmethyl]-3-(2-oxo-2,3-dihydrobenzoxazol-6-yl)-4,5-dihydroisoxazole-5-carboxylic acid (275 mg, 85%) as a white solid:

mp 188–194° C.

IR (KBr): 2959, 2921, 1774, 1630, 1509 cm$^{-1}$ $^1$H NMR (300 MHz, DMSO-d$_6$): δ 11.92 (s, 1H), 7.58 (s, 1H), 7.48 (d, J 8 Hz, 1H), 7.24–7.07 (m, 8H), 3.89 (d, J 17 Hz, 1H), 3.45–3.16 (m, 5H), 2.60–2.50 (m, 2H), 1.64 (m, 3H), 1.31 (m, 2H)

ESI-MS (m/z): 454 [M+H]$^+$

HPLC: method C, 6.56 min (97.0%); method D, 12.33 min (99.5%); Anal. Calcd for C$_{24}$H$_{24}$FN$_3$O$_5$.0.5H$_2$O: C, 62.33; H, 5.45; N, 9.09. Found: C, 62.57; H, 5.47 N, 9.00.

EXAMPLE 23

5-[4-(4-Fluorobenzyl)piperidin-1-ylmethyl]-3-(2-oxo-2,3-dihydrobenzoxazol-6-yl)-4,5-dihydroisoxazole-5-carboxylic acid methyl ester

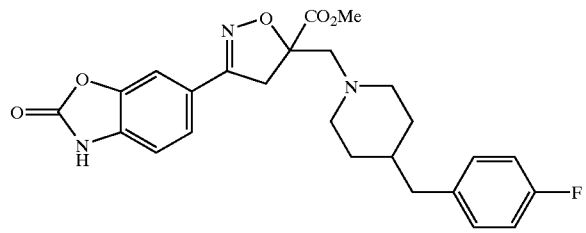

To a solution of 5-[4-(4-fluorobenzyl)piperidin-1-ylmethyl]-3-(2-oxo-2,3-dihydrobenzoxazol-6-yl)-4,5-dihydroisoxazole-5-carboxylic acid (687 mg, 0.909 mmol) in MeOH (20 mL) and TFA (1.5 mL) was added p-toluenesulfonic acid monohydrate (190 mg, 0.999 mmol). The reaction mixture was heated to reflux overnight, then concentrated and purified by flash chromatography (silica gel, 5% MeOH in CH$_2$Cl$_2$) to give 5-[4-(4-fluorobenzyl)piperidin-1-ylmethyl]-3-(2-oxo-2,3-dihydrobenzoxazol-6-yl)-4,5-dihydroisoxazole-5-carboxylic acid methyl ester (133 mg, 31%), as an off white solid:

mp 146–155° C.

IR (KBr): 2930, 1767, 1508, 1448 cm$^{-1}$ $^1$H NMR (500 MHz, CD$_3$OD): δ 7.58 (d, J 1 Hz, 1H), 7.51 (dd, J 8, 1 Hz, 1H), 7.20 (dd, J 8, 5 Hz, 2H), 7.16 (d, J 8 Hz, 1H), 7.03 (d, J 9 Hz, 1H), 7.00 (d, J 9 Hz, 1H), 3.96 (d, J 18 Hz, 1H), 3.92–3.90 (m, 4H), 3.68 (d, J 18 Hz, 1H), 3,68–3.55 (m, 3H), 3.21–3.05 (m, 2H), 2.62 (d, J 7 Hz, 2H), 1.97–1.83 (m, 3H), 1.71–1.55 (m, 2H)

APCI (m/z): 468 [M+H]$^+$

HPLC: method A, 6.32 min, 98.7%; Anal. Calcd for C$_{24}$H$_{26}$FN$_3$O$_5$.HCl: C, 59.58; H, 5.40; N, 8.34. Found: C, 59.19; H, 5.56; N, 8.01.

EXAMPLE 24

4-(4-Fluorobenzyl)-1-[3-(2-oxo-2,3-dihydrobenzoxazol-6-yl)-4,5-dihydroisoxazol-5-ylmethyl]piperidine-4-carboxylic acid ethyl ester

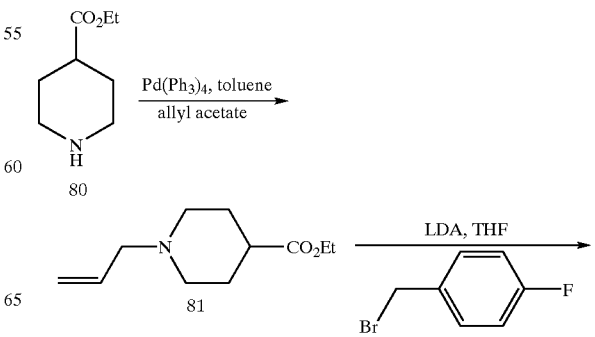

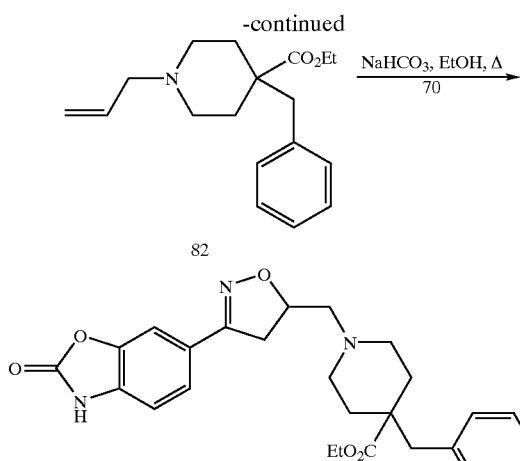

Step 1: Treatment of amine 80 (2.0 g, 13 mmol) with allyl acetate (1.6 mL, 14 mmol), and Pd(Ph₃)₄ (440 mg, 3.8 mmol), following the procedure described in Example 20, Step 1, gave 81 (2.3 g, 88%):

¹H NMR (300 MHz, CDCl₃): δ 5.97–5.79 (m, 1H), 5.26–5.10 (m, 2H), 4.21–4.09 (m, 2H), 2.99–2.87 (m, 4H), 2.35–2.20 (m, 1H), 2.04–1.65 (m, 6H), 1.27–1.22 (m, 3H).

Step 2: To an ice-cold solution of diisopropylamine (0.78 mL, 5.6 mmol) in THF (22 mL) was added n-BuLi (2.2 mL of a 2.5 M solution in hexanes, 5.6 mmol). After 15 minutes, the reaction mixture was cooled in a −78° C. dry ice/2-PrOH bath and then a solution of 81 (1.0 g, 5.1 mmol) in THF (10 mL) was added dropwise over 15 minutes. After 1.5 hours, a solution of 4-fluorobenzyl bromide (0.66 mL, 5.3 mmol) in THF (10 mL) was added dropwise to the reaction mixture over 1.5 hours. The reaction mixture was stirred for an additional 35 minutes and then warmed to ambient temperature. The reaction mixture was poured into H₂O and extracted with EtOAc (3×). The combined organics were dried (Na₂SO₄) and concentrated under reduced pressure. Purification by flash chromatography (silica, 95:4.5:0.5 CH₂Cl₂/MeOH/NH₄OH) gave 82 (1.3 g, 81%):

¹H NMR (300 MHz, CDCl₃) δ 7.03–6.90 (m, 4H), 5.90–5.79 (m, 1H), 5.18–5.11 (m, 2H), 4.09 (q, J 7 Hz, 2H), 2.94 (d, J 7 Hz, 2H), 2.78 (s, 4H), 2.13 (d, J 13 Hz, 2H), 1.96 (dd, J 12, 12 Hz, 2H), 1.61–1.51 (m, 2H), 1.19 (t, J 7 Hz, 3H).

Step 3: Coupling of 70 (1.0 g, 4.7 mmol) and alkene 82 (1.3 g, 4.2 mmol) following the procedure described in Example 17, Step 5, gave 4-(4-fluorobenzyl)-1-[3-(2-oxo-2,3-dihydrobenzoxazol-6-yl)-4,5-dihydroisoxazol-5-ylmethyl]piperidine-4-carboxylic acid ethyl ester (630 mg, 31%), as a white solid:

mp 212–214° C.

IR (KBr): 2836, 1767, 1705, 1511, 1451 cm⁻¹

¹H NMR (300 MHz, DMSO-d₆): δ 11.80 (br s, 1H), 7.55 (d, J 1 Hz, 1H), 7.45 (dd, J 8, 1 Hz, 1H), 7.14 (d, J 8 Hz, 1H), 7.08 (d, J 8 Hz, 4H), 4.83–4.77 (m, 1H), 4.04 (dd, J 14, 7 Hz, 2H), 3.44 (dd, J 17, 7 Hz, 1H), 3.12 (dd, J 17, 7 Hz, 1H), 2.84–2.76 (m, 4H), 2.52–2.43 (m, 2H), 2.08–2.00 (m, 2H), 1.94–1.91 (m, 2H), 1.53–1.47 (m, 2H), 1.14 (dd, J 7, 7 Hz, 3H)

APCI (m/z): 482 [M+H]⁺

HPLC: method B, 11.50 min (97.5%); Anal. Calcd for C₂₆H₂₈FN₃O₅: C, 64.85; H, 5.86; N, 8.73. Found: C, 64.56; H, 5.74; N, 8.62.

EXAMPLE 25

4-(4-Fluorobenzyl)-1-[3-(2-oxo-2,3-dihydrobenzoxazol-6-yl)-4,5-dihydroisoxazol-5-ylmethyl]piperidine-4-carboxylic acid

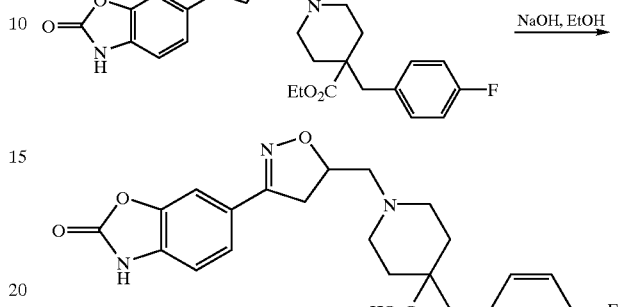

Step 1: A mixture of 4-(4-fluorobenzyl)-1-[3-(2-oxo-2,3-dihydrobenzoxazol-6-yl)-4,5-dihydroisoxazol-5-ylmethyl] piperidine-4-carboxylic acid ethyl ester (390 mg, 0.81 mmol) and 20% aq. NaOH (4.5 mL) in EtOH (4.5 mL) was heated to reflux for 16 hours. After stirring at ambient temperature overnight, the reaction solvent was removed under reduced pressure. The reaction mixture was diluted with water, brought to pH 3 with 1N HCl, and extracted with EtOAc (2×). The combined extracts were dried (Na₂SO₄) and concentrated under reduced pressure. Purification by chromatography (silica, 79:20:1 CH₂Cl₂/MeOH/AcOH) followed by recrystallization from MeOH/Et₂O gave 4-(4-fluorobenzyl)-1-[3-(2-oxo-2,3-dihydrobenzoxazol-6-yl)-4,5-dihydroisoxazol-5-ylmethyl]piperidine-4-carboxylic acid (28 mg, 8%) as a yellow solid:

IR (KBr): 2922, 1767, 1600, 1508, 1448 cm⁻¹ ¹H NMR (500 MHz, DMSO-d₆): δ 7.55 (d, J 1 Hz, 1H), 7.45 (dd, J 8, 2 Hz, 1H), 7.14–7.11 (m, 3H), 7.07 (d, J 8, 8 Hz, 2H), 3.46–3.10 (m, 4H), 2.79–2.73 (m, 4H), 2.52–2.43 (m, 2H), 2.13–2.06 (m, 2H), 1.89–1.87 (m, 2H), 1.47–1.42 (m, 2H), ESI-MS (m/z): 454 [M+H]⁺ HPLC: method A, 5.30 min (>99%).

EXAMPLE 26

6-{5-[4-(4-Fluorobenzyl)-3-hydroxypiperidin-1-ylmethyl]-4,5-dihydroisoxazol-3-yl}-3H-benzoxazol-2-one

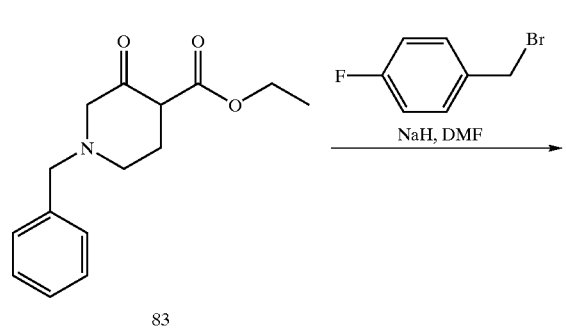

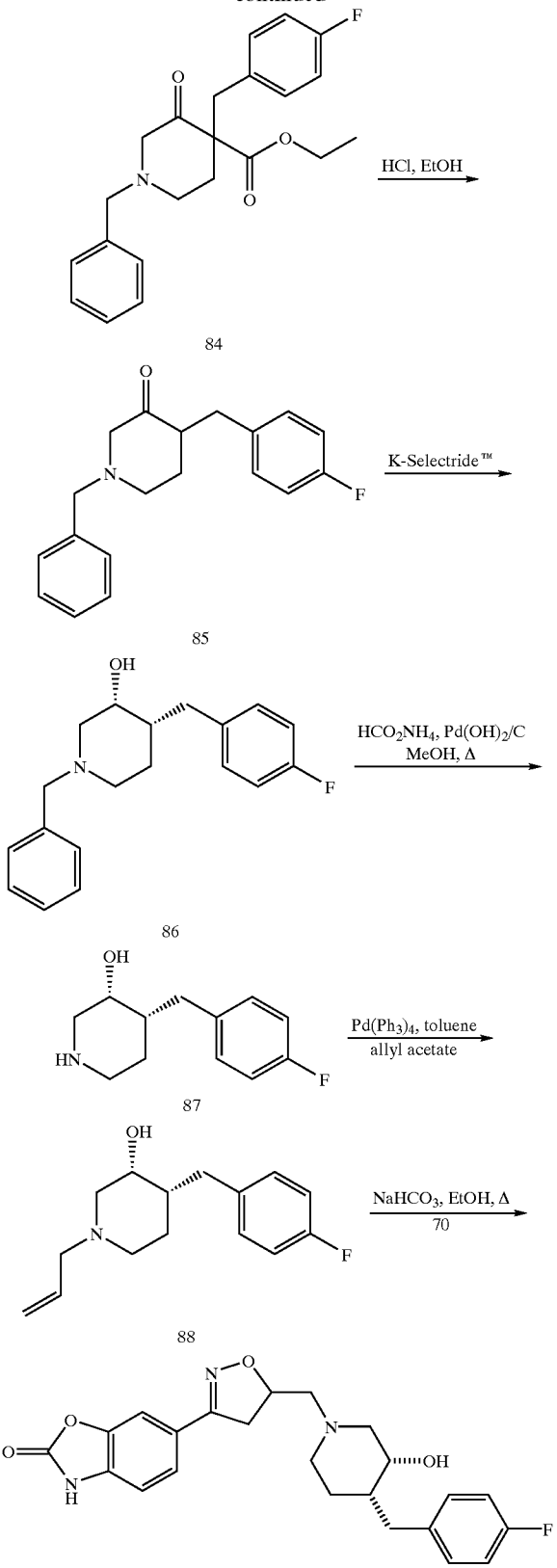

maintained between 5° C. to 10° C. After stirring at ambient temperature for 1 hour, the reaction mixture was cooled in an ice/H2O bath and a solution of 4-fluorobenzyl bromide (9.4 g, 50 mmol) in DMF (26 mL) was added. After stirring at ambient temperature for 15 hours, the reaction mixture was cooled in an ice/$H_2O$ bath, and quenched by the addition of sat. $NaHCO_3$. The mixture was diluted with $H_2O$ (200 mL) and extracted with EtOAc (3×200 mL). The combined extracts were washed with $H_2O$ (100 mL) and sat. NaCl (100 mL), dried ($MgSO_4$), and concentrated under reduced pressure. Purification by flash chromatography (silica, 8:1 hexanes/EtOAc followed by 4:1 hexanes/EtOAc) gave 84 (9.0 g, 49%):

$^1$H NMR (300 MHz, $CDCl_3$): δ 7.35–7.19 (m, 5H), 7.11 (dd, J 8, 3 Hz, 2H), 6.92 (dd, J 8, 8 Hz, 2H), 4.16–3.99 (m, 2H), 3.51 (q, J 13 Hz, 2H), 3.28–2.84 (m, 4H), 2.78–2.61 (m, 1H), 2.61–2.48 (m, 2H), 1.68–1.58 (m, 1H), 1.09 (t, J 7 Hz, 3H).

Step 2: To a solution of 84 (8.9 g, 24 mmol) in EtOH (13 mL) was added conc. HCl (30 mL), and the solution was heated to reflux. After 21 hours, the reaction mixture was cooled in an ice/$H_2O$ bath, brought to pH 8 with 1N NaOH and then extracted with EtOAc (3×200 mL). The combined extracts were washed with $H_2O$ (100 mL) and sat. NaCl (100 mL), dried ($Na_2SO_4$), and concentrated under reduced pressure to give 85 (6.5 g, 89%), which was used without further purification:

$^1$H NMR (500 MHz, $CDCl_3$) δ 7.34–7.23 (m, 5H), 7.11 (dd, J 8, 3 Hz, 2H), 6.95 (dd, J 8, 8 Hz, 2H), 3.57 (s, 2H), 3.26 (d, J 12 Hz, 2H), 2.94–2.79 (m, 2H), 2.47–2.34 (m, 3H), 1.93–1.87 (m, 1H), 1.71–1.52 (m, 1H).

Step 3: To a cold (−78° C. dry ice/2-PrOH bath) solution of 85 (8.8 g, 29 mmol) in THF (200 mL) was added K-selectride™ (44 mL of a 1 M solution in THF, 44 mmol) at a rate that maintained the internal reaction temperature below −65° C. After the addition was complete, the reaction mixture was stirred for 1 hour (internal temperature −65° C.) and then warmed to ambient temperature. The reaction was quenched by the addition of sat. $NaHCO_3$ (100 mL) and then extracted with EtOAc (2×200 mL). The combined extracts were washed with $H_2O$ (100 mL) and sat. NaCl (100 mL), dried ($Na_2SO_4$), and concentrated under reduced pressure. Purification by flash chromatography (silica, 2:1 hexanes/EtOAc followed by 1:2 hexanes/EtOAc) gave 86 (4.0 g, 46%):

$^1$H NMR (300 MHz, $CDCl_3$): δ 7.33–7.25 (m, 5H), 7.15 (dd, J 6, 3 Hz, 2H), 6.95 (dd, J 8, 8 Hz, 2H), 3.57–3.52 (m, 1H), 3.50 (s, 2H), 2.96–2.71 (m, 3H), 2.58–2.49 (m, 1H), 2.07 (d, J 12 Hz, 1H), 2.09–1.92 (m, 1H), 1.62–1.30 (m, 4H).

Step 4: A mixture of compound 86 (4.0 g, 13 mmol), ammonium formate (1.7, 27 mmol), and 20% Pd(OH)$_2$/C (500 mg) in MeOH (50 mL) was heated at reflux for 1.5 hours. The reaction mixture was cooled to ambient temperature, filtered through Celite, and the filtrate was concentrated under reduced pressure to give amine 87 (2.8 g, 100%), which was used without further purification:

$^1$H NMR (300 MHz, $CDCl_3$): δ 7.15 (dd, J 6, 3 Hz, 2H), 6.96 (dd, J 8, 8 Hz, 2H), 3.55 (br. s, 1H), 3.48 (s, 2H), 3.03 (dd, J 12, 12 Hz, 2H), 2.75–2.48 (m, 4H), 1.68–1.31 (m, 3H).

Step 5: Treatment of amine 87 (1.4 g, 6.6 mmol) with allyl acetate (0.79 mL, 7.3 mmol), and Pd(Ph$_3$)$_4$ (380 mg, 0.30 mmol), following the procedure described in Example 20, Step 1, gave 88 (1.1 g, 66%):

$^1$H NMR (300 MHz, $CDCl_3$) δ 7.14 (dd, J 8, 3 Hz, 2H), 6.96 (dd, J 8, 8 Hz, 2H), 5.90–5.76 (m, 1H), 5.18–5.11 (m, 2H), 3.58–3.56 (m, 1H), 3.00–2.48 (m, 6H), 2.05–1.81 (m, 2H), 1.61–1.31 (m, 4H).

Step 1: To an ice-cold suspension of NaH (2.6 g, 110 mmol) in DMF (130 mL) was added 83 (15.0 g, 50 mmol) portionwise so that the internal reaction temperature was Step 6: Coupling of 70 (500 mg, 2.4 mmol) and alkene 88 (530 mg, 2.1 mmol) following the procedure described in Example 17, Step 5, followed by conversion to the HCl salt, gave 6-{5-[4-(4-fluorobenzyl)-3-hydroxypiperidin-1-ylmethyl]-4,5-dihydroisoxazol-3-yl}-3H-benzoxazol-2-one (288 mg, 29%), as a white solid:

mp 224–233° C.

IR (KBr): 2957, 1771, 1509, 1453 cm$^{-1}$ $^1$H NMR (300 MHz, CD$_3$OD): δ 7.58–7.57 (m, 1H), 7.53–7.49 (m, 1H), 7.27–7.23 (m, 2H), 7.16–7.12 (m, 1H), 7.05–6.99 (m, 2H), 5.28–5.07 (m, 1H), 3.89 (br s, 1H), 3.76–3.62 (m, 1H), 3.48–3.01 (m, 6H), 2.82–2.59 (m, 2H), 2.11–1.85 (m, 2H), 1.75–1.62 (m, 2H)

APCI (m/z): 426 [M+H]$^+$

HRMS-API (m/z): [M+H]$^+$ Calcd for C$_{23}$H$_{24}$FN$_3$O$_4$, 426.1829; Found, 426.1834

HPLC: method A, 6.15 min (96.1%); method B, 11.07 min (>99%); Anal. Calcd for C$_{23}$H$_{24}$FN$_3$O$_4$·HCl·0.25H$_2$O: C, 59.23; H, 5.51; N, 9.01. Found: C, 59.16; H 5.41; N, 8.87.

EXAMPLE 27

6-{5-[4-(4-Fluorophenoxy)piperidin-1-ylmethyl]-4,5-dihydroisoxazol-3-yl}-3-H-benzoxazol-2-one

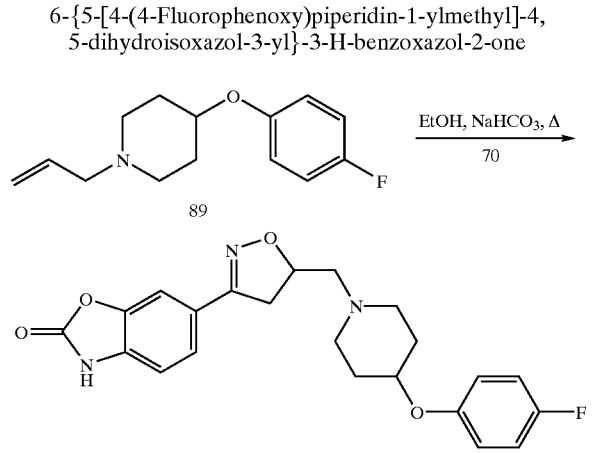

Step 1: A mixture of 4-(4-fluorophenoxy)piperidine hydrochloride (1.48 g, 6.40 mmol) and NaHCO$_3$ (1.34 g, 16.0 mmol) in DMF (30 mL) was heated to 50° C. for 30 minutes. Allyl bromide (0.550 mL, 6.40 mmol) was added and the reaction mixture was stirred at 50° C. for 2 hours. The reaction mixture was partitioned between EtOAc and water. The aqueous layer was extracted with EtOAc (1×). The combined organic extracts were washed with sat. NaCl, dried (Na$_2$SO$_4$), and concentrated under reduced pressure. Purification by flash chromatography (silica, 95:5 to 9:1 CH$_2$Cl$_2$/MeOH) gave 89 (621 mg, 41%) as an oil:

$^1$H NMR (300 MHz, CDCl$_3$): δ 6.96 (dd, J 9, 9 Hz, 2H), 6.88–6.83 (m, 2H), 5.95–5.82 (m, 1H), 5.22–5.13 (m, 2H), 4.26–4.19 (m, 1H), 3.03 (d, J 7 Hz, 2H), 2.74–2.72 (m, 2H), 2.32–2.25 (m, 2H), 2.02–1.95 (m, 2H), 1.86–1.75 (m, 2H).

Step 2: To a mixture of alkene 89 (620 mg, 2.63 mmol) and NaHCO$_3$ (400 mg, 4.76 mmol) in 2:1 DMF/H$_2$O (3 mL) was added a solution of 70 (500 mg, 2.35 mmol) in DMF (2 mL). The mixture was heated to 50° C. for 2 hours. The reaction mixture was partitioned between EtOAc and water. The aqueous layer was extracted with EtOAc (2×). The combined organic extracts were washed with sat. NaCl, dried (Na$_2$SO$_4$), and concentrated under reduced pressure. Purification by flash chromatography (silica, 89:10:1 CH$_2$Cl$_2$/MeOH/NH$_4$OH) and (silica, 1:1 hexanes/EtOAc to EtOAc to 89:10:1 CH$_2$Cl$_2$/MeOH/NH$_4$OH) followed by crystallization from MeOH gave 6-{5-[4-(4-fluorophenoxy)piperidin-1-ylmethyl]-4,5-dihydroisoxazol-3-yl}-3H-benzoxazol-2-one (225 mg, 19%):

mp 192–194° C.

IR (KBr): 2951, 1779 cm$^{-1}$ $^1$H NMR (500 MHz, DMSO-d$_6$): δ 11.78 (s, 1H), 7.55 (d, J 1 Hz, 1H), 7.45 (dd, J 8, 1 Hz, 1H), 7.13 (d, J 8 Hz, 1H), 7.07 (dd, J 9, 9 Hz, 2H), 6.94 (dd, J 9, 4 Hz, 2H), 4.86–4.80 (m, 1H), 4.31–4.26 (m, 1H), 3.46 (dd, J 17, 11 Hz, 1H), 3.16 (dd, J 17, 8 Hz, 1H), 2.81–2.75 (m, 2H), 2.60–2.51 (m, 2H), 2.38–2.30 (m, 2H), 1.91–1.88 (m, 2H), 1.63–1.56 (m, 2H)

APCI-MS (m/z): 412 [M+H]$^+$

HPLC: method A, 6.23 min (>99%)

Anal. Calcd for C$_{22}$H$_{22}$FN$_3$O$_4$: C, 64.22; H, 5.39; N, 10.21. Found: C, 64.00; H, 5.46; N, 10.08.

EXAMPLE 28

6-{5-[4-(4-Fluorophenylsulfanyl)piperidin-1-ylmethyl]-4,5-dihydroisoxazol-3-yl}-3H-benzoxazol-2-one

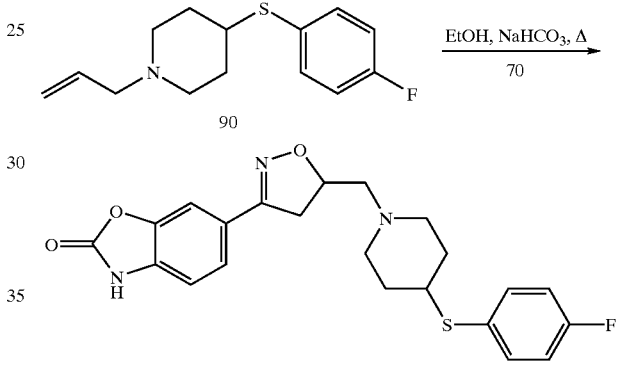

Step 1: Coupling of 4-(4-fluorophenylsulfanyl)piperidine hydrochloride (647 mg, 2.61 mmol) with allyl bromide (250 μL, 2.87 mmol) following the procedure described in Example 16, Step 1, gave alkene 90 (271 mg, 40%):

$^1$HNMR(500 MHz, CD$_3$OD): δ 7.46 (dd, J 9, 5 Hz, 2H), 7.05 (dd, J 9, 9 Hz, 2H), 5.89–5.80 (m, 1H), 5.21–5.15 (m, 2H), 3.08–3.02 (m, 1H), 3.00 (d, J 7 Hz, 2H), 2.90–2.87 (m, 2H), 2.13–2.08 (m, 2H), 1.95–1.91 (m, 2H), 1.63–1.56 (m, 2H).

Step 2: Coupling of 70 (252 mg, 1.18 mmol) and alkene 90 (271 mg, 1.08 mmol) following the procedure described in Example 17, Step 5, gave 6-{5-[4-(4-fluorophenylsulfanyl)piperidin-1-ylmethyl]-4,5-dihydroisoxazol-3-yl}-3H-benzoxazol-2-one (370 mg, 80%):

mp 190–192° C.

IR (KBr): 2945, 1774 cm$^{-1}$ $^1$H NMR (500 MHz, DMSO-d$_6$): δ 11.80 (s, 1H), 7.54 (d, J 1 Hz, 1H), 7.47–7.43 (m, 3H), 7.18 (dd, J 9, 9 Hz, 1H), 7.13 (d, J 8 Hz, 1H), 4.84–4.78 (m, 1H), 3.44 (dd, J 17, 11 Hz, 1H), 3.18–3.09 (m, 2H), 2.90–2.83 (m, 2H), 2.56–2.48 (m, 2H), 2.21–2.14 (m, 2H), 1.85–1.83 (m, 2H), 1.51–1.42 (m, 2H)

ESI-MS (m/z): 428 [M+H]$^+$

HPLC: method A, 6.40 min (98.9%); method B, 11.50 min (99.0%/)

Anal. Calcd for C$_{22}$H$_{22}$FN$_3$O$_3$S: C, 61.81; H, 5.19; N, 9.83. Found: C, 62.13; H, 5.05; N, 9.86.

EXAMPLE 29

6-{5-[4-(4-Fluorobenzenesulfinyl)piperidin-1-ylmethyl]-4,5-dihydroisoxazol-3-yl}-3H-benzoxazol-2-one

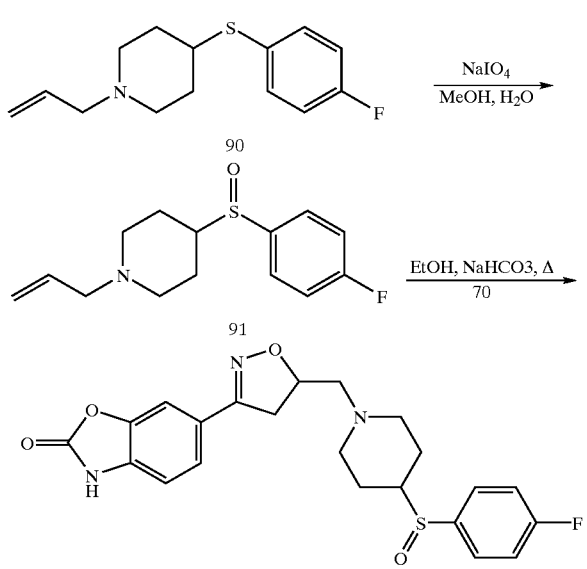

Step 1: To a solution of 90 (0.80 g, 3.18 mmol) in MeOH (10 mL) and H$_2$O (1.5 mL) was added NaIO$_4$ (680 mg, 3.18 mmol) at ambient temperature. The reaction mixture was stirred for 12 hours, and then additional NaIO$_4$ (100 mg, 0.47 mmol) was added. After 12 hours, the reaction mixture was filtered through Celite and concentrated under reduced pressure. Purification by flash chromatography (silica, 9:1 to 8:2 CH$_2$Cl$_2$/MeOH) gave 91 (240 mg, 28%) as a yellow wax:

$^1$H NMR (300 MHz, CDCl$_3$): δ 7.69–7.57 (m, 2H), 7.33–7.16 (m, 2H), 5.82 (dddd, J 17, 13, 10, 7 Hz, 1H), 5.22–5.12 (m, 2H), 3.10–2.93 (m, 4H), 2.65–2.52 (m, 1H), 2.03–1.88 (m, 2H), 1.81–1.52 (m, 4H).

Step 2: Coupling of 70 (209 mg, 0.98 mmol) and alkene 91 (230 mg, 0.86 mmol) following the procedure described in Example 17, Step 5, followed by conversion to the HCl salt, gave 6-{5-[4-(4-fluorobenzenesulfinyl)piperidin-1-ylmethyl]-4,5-dihydroisoxazol-3-yl}-3H-benzoxazol-2-one (290 mg, 76%):

mp 170–178° C.

IR (KBr): 2954, 1764 cm$^{-1}$ $^1$H NMR (500 MHz, DMSO-d$_6$): δ 11.92 (s, 1H), 10.23 (br s, 1H), 7.73 (d, J 6 Hz, 1H), 7.71 (d, J 5 Hz, 1H), 7.56 (s, 1H), 7.52–7.44 (m, 3H), 7.15 (d, J 8 Hz, 1H), 5.22 (br s, 1H), 3.72 (m, 3H), 3.40–3.25 (m, 3H), 3.12 (m, 3H), 2.12 (br s, 1H), 2.01–1.75 (m, 2H), 1.67 (br s, 1H); APCI-MS (m/z): 444 [M+H]$^+$ HPLC: method A, 4.61 min (95.0%); method B, 8.76 min (93.8%) Anal. Calcd for C$_{22}$H$_{22}$FN$_3$O$_4$S.HCl.0.5H$_2$O: C, 54.04; H, 4.95; N, 8.59. Found: C, 54.06; H, 4.73; N, 8.38.

EXAMPLE 30

6-{5-[4-(4-Fluorobenzoyl)piperidin-1-ylmethyl]-4,5-dihydroisoxazol-3-yl}-3H-benzoxazol-2-one

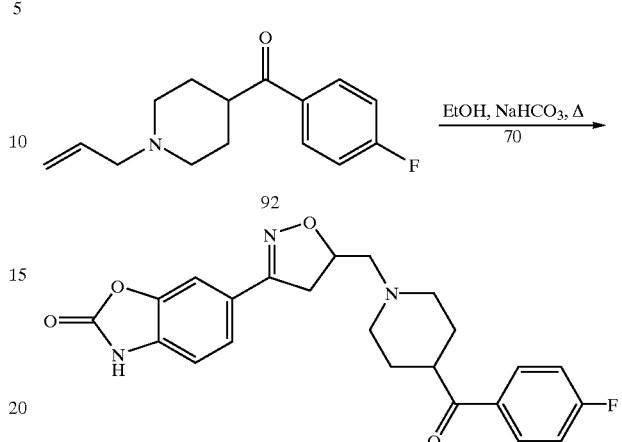

Step 1: Coupling of (4-fluorophenyl)piperidin-4-yl-methanone (1.50 g, 6.62 mmol) with allyl bromide (630 μL, 7.28 mmol) following the procedure described in Example 16, Step 1 gave alkene 92 (830 mg, 51%):

$^1$H NMR (300 MHz, CDCl$_3$): δ 7.97 (dd, J 8, 6 Hz, 2H), 7.14 (dd, J 9, 8 Hz, 2H), 5.94–5.85 (m, 1H), 5.23–5.14 (m, 2H), 3.22–3.17 (m, 1H), 3.04–3.00 (m, 4H), 2.13–2.05 (m, 2H), 1.92–1.80 (m, 4H)

Step 2: Coupling of 708 (787 mg, 3.70 mmol) and alkene 92 (830 mg, 3.36 mmol) following the procedure described in Example 17, Step 5 gave 6-{5-[4-(4-fluorobenzoyl)piperidin-1-ylmethyl]-4,5-dihydroisoxazol-3-yl}-3H-benzoxazol-2-one (465 mg, 33%):

mp 188–190° C.; IR (KBr): 2950, 1776 cm$^{-1}$ $^1$H NMR (500 MHz, DMSO-d$_6$): δ 11.76 (s, 1H), 8.05 (dd, J 9, 5 Hz, 2H), 7.56 (s, 1H), 7.47 (dd, J 9, 2 Hz, 1H), 7.34 (t, J 9 Hz, 2H), 7.14 (d, J 9 Hz, 1H), 4.92–4.80 (m, 1H), 3.48–3.09 (dd, J 17, 10 Hz, 1H), 3.39 (m, 1H), 3.18 (dd, J 17, 8 Hz, 1H), 2.99 (m, 2H), 2.70–2.50 (m, 2H), 2.37–2.18 (m, 2H), 1.80–1.70 (m, 2H), 1.65–1.54 (m, 2H)

ESI-MS (m/z): 424 [M+H]$^+$

HPLC: method A, 5.81 min (95.1%); method B, 10.92 min (97.1%)

Anal. Calcd for C$_{23}$H$_{22}$FN$_3$O$_4$.0.25H$_2$O: C, 64.55; H, 5.30; N, 9.82. Found: C, 64.64; H, 5.04; N, 9.75.

EXAMPLE 31

6-(5-{4-[(4-Fluorophenyl)hydroxymethyl]piperidin-1-ylmethyl}-4,5-dihydroisoxazol-3-yl)-3H-benzoxazol-2-one

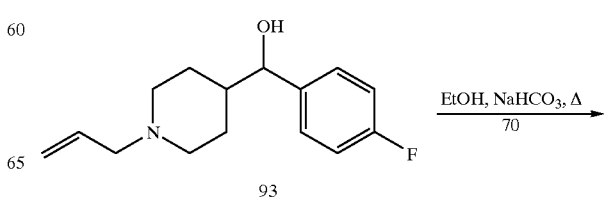

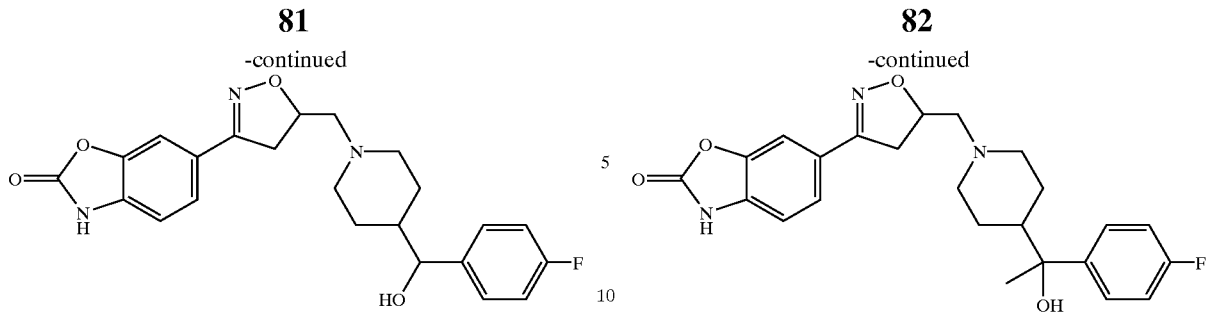

Step 1: To an ice-cold solution of alkene 92 (507 mg, 2.05 mmol) in 1:1 MeOH/CH$_2$Cl$_2$ (10 mL) was added NaBH$_4$ (67.3 mg, 2.41 mmol) portionwise. The reaction was quenched with sat. NH$_4$Cl (1 mL) and the solvent was removed under reduced pressure. The residue was partitioned between EtOAc and water. The organic layer was washed with sat. NaCl, dried (Na$_2$SO$_4$), and concentrated under reduced pressure. Purification by flash chromatography (silica, 89:10:1 CH$_2$Cl$_2$/MeOH/NH$_4$OH) gave alkene 93 (252 mg, 49%) as an off-white solid:

$^1$H NMR (300 MHz, CDCl$_3$): δ 7.29–7.25 (m, 3H), 7.05–7.00 (m, 2H), 5.92–5.78 (m, 1H), 5.18–5.10 (m, 2H), 4.37 (d, J 7 Hz, 1H), 3.01–2.85 (m, 4H), 2.00–1.21 (m, 7H).

Step 2: Coupling of 70 (738 mg, 3.48 mmol) and alkene 93 (722 mg, 2.90 mmol) following the procedure described in Example 17, Step 5, followed by conversion to the HCl salt gave 6-(5-{4-[(4-fluorophenyl)hydroxymethyl]piperidin-1-ylmethyl}-4,5-dihydroisoxazol-3-yl)-3H-benzoxazol-2-one (951 mg, 81%):

mp 186–191° C.

IR (KBr): 3393, 2958, 1771 cm$^{-1}$ $^1$H NMR (300 MHz, CD$_3$OD): δ 7.58 (s, 1H), 7.51 (d, J 8 Hz, 1H), 7.37 (dd, J 8, 5 Hz, 2H), 7.15–7.39 (m, 3H), 5.26–5.13 (m, 1H), 4.46 (d, J 7 Hz, 1H), 4.0–3.62 (m, 3H), 3.42–3.19 (m, 4H), 3.12–2.97 (m, 2H), 2.19–2.10 (m, 1H), 1.98–1.82 (m, 1H), 1.80–1.55 (m, 3H)

APCI-MS (m/z): 426 [M+H]$^+$

HPLC: method A, 5.51 min (>99%); method B, 10.40 min (97.9%)

Anal. Calcd for C$_{23}$H$_{24}$FN$_3$O$_4$·HCl·0.25H$_2$O: C, 59.23; H, 5.51; N, 9.01. Found: C, 59.11; H, 5.29; N, 8.75.

EXAMPLE 32

6-(5-{4-[1-(4-Fluorophenyl)-1-hydroxyethyl]piperidin-1-ylmethyl}-4,5-dihydroisoxazol-3-yl)-3H-benzoxazol-2-one Step 1: To an ice-cold solution of MeMgBr (1.15 mL of a 3.0 M solution in Et$_2$O, 3.46 mmol) was added dropwise a solution of ketone 92 (712 mg, 2.88 mmol) in dry Et$_2$O. After 1 hour, the reaction was quenched with MeOH (1 mL) and sat. NH$_4$Cl (1 mL). The mixture was partitioned between water and Et$_2$O. The aqueous layer was extracted with Et$_2$O. The combined organic layers were washed with sat. NaCl, dried (Na$_2$SO$_4$), and concentrated under reduced pressure. Purification by flash chromatography (silica, 90:10 CH$_2$Cl$_2$/MeOH) gave alkene 94 as a yellow oil (755 mg, 92%):

$^1$H NMR (300 MHz, CDCl$_3$): δ 7.39–7.34 (m, 2H), 7.03–6.97 (m, 2H), 5.93–5.79 (m, 1H), 5.18–5.12 (m, 2H), 2.96 (d, J 6 Hz, 4H), 1.89–1.81 (m, 3H), 1.63–1.48 (m, 5H), 1.44–1.26 (m, 3H).

Step 2: Coupling of 70 (755 mg, 3.56 mmol) and alkene 94 (693 mg, 3.23 mmol) following the procedure described in Example 17, Step 5 gave 6-(5-{4-[1-(4-fluorophenyl)-1-hydroxyethyl]piperidin-1-ylmethyl}-4,5-dihydroisoxazol-3-yl)-3H-benzoxazol-2-one (1.00 g, 64%):

mp 125–134° C.

IR (KBr): 3427, 2944, 1774 cm$^{-1}$ $^1$H NMR (300 MHz, DMSO-d$_6$): δ 11.79 (s, 1H), 7.55 (s, 1H), 7.46–7.38 (m, 3H), 7.14–7.07 (m, 3H), 4.85–4.79 (m, 2H), 3.48–3.38 (m, 1H), 3.14–3.06 (m, 1H), 2.99–2.89 (m, 2H), 2.51–2.46 (m, 2H), 2.00–1.80 (m, 2H), 1.65–1.51 (m, 1H), 1.50–1.45 (m, 4H), 1.35–1.10 (m, 3H)

APCI-MS (m/z): 440 [M+H]$^+$

HPLC: method A, 5.60 min (97.0%); method B, 10.70 min (98.2%)

Anal. Calcd for C$_{24}$H$_{26}$FN$_3$O$_4$·0.25H$_2$O: C, 64.93; H, 6.02; N, 9.46. Found: C, 64.65; H, 5.85; N, 9.26.

EXAMPLE 33

4-Chloro-6-{5-[4-(4-fluorobenzyl)piperidin-1-ylmethyl]-4,5-dihydroisoxazol-3-yl}-5-methyl-3H-benzoxazol-2-one

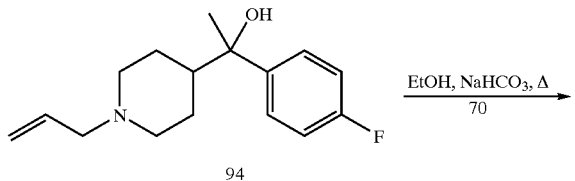

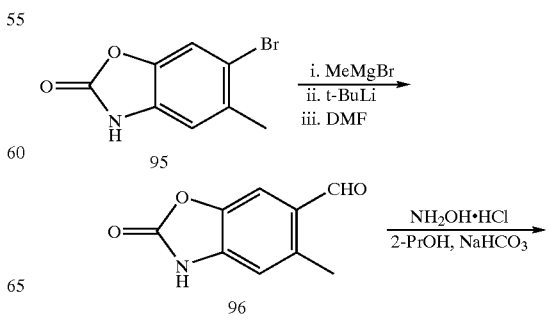

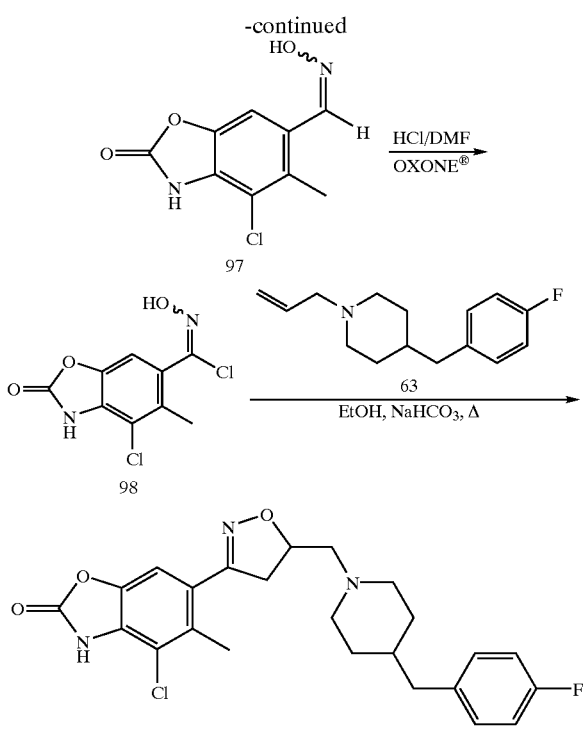

Step 1: To a −78° C. solution of bromide 95 (10.3 g, 45.2 mmol) in THF (40 mL) was added MeMgBr (16.6 mL of a 3.0 M solution in diethyl ether, 49.7 mmol). After 40 minutes, anhydrous THF (410 mL) was added at a rate that maintained the internal reaction temperature below a threshold of −50° C. After the solution returned to −78° C., tert-butyl lithium (85 mL of a 1.7 M solution in pentane, 144 mmol) was added via a dropping funnel. After 10 minutes, DMF (21.0 mL, 271 mmol) was added to the yellow mixture, and then the cold bath was removed. After 2 hours, the reaction was quenched with water and the THF removed under reduced pressure. The residue was partitioned between EtOAc and 1N HCl. The aqueous layer was extracted with EtOAc (2×). The combined organic extracts were washed with sat. NaCl, dried ($Na_2SO_4$), and concentrated under reduced pressure. Purification by crystallization from hot EtOH gave aldehyde 96 (2.86 g, 35%):

hu 1H NMR (300 MHz, $CDCl_3$): δ 11.60 (s, 1H), 10.23 (s, 1H), 7.58 (s, 1H), 6.91 (s, 1H), 2.68 (s, 3H).

Step 2: A mixture of aldehyde 96 (2.80 g, 15.8 mmol), hydroxylamine hydrochloride (1.21 g, 17.4 mmol), and sodium bicarbonate (1.99 g, 23.7 mmol) in 2-PrOH (80 mL) was heated to 50° C. for 4 hours. The warm mixture was diluted with MeOH, and filtered. Concentration under reduced pressure gave oxime 97 (3.69 g, 100%):

$^1$H NMR (300 MHz, DMSO-$d_6$): δ 11.17 (s, 1H), 8.30 (s, 1H), 7.41 (s, 1H), 6.91 (s, 1H), 2.36 (s, 3H).

Step 3: A mixture of oxime 97 (3.69 g, 15.8 mmol) and OXONE® (10.7 g, 17.4 mmol) was stirred in HCl (32.8 mL of a 0.53 M solution in DMF, 17.4 mmol) for 3 hours. The reaction mixture was partitioned between EtOAc and water. The aqueous layer was extracted with EtOAc (2×). The combined organic extracts were washed with water, sat. NaCl, dried ($Na_2SO_4$), and concentrated under reduced pressure. The yellow solid was dissolved in hot EtOAc. Addition of hexane to the solution gave 98 (3.04 g, 73%) as an off-white solid:

$^1$H NMR (300 MHz, DMSO-$d_6$): δ 12.45 (s, 1H), 7.96 (s, 1H), 7.42 (s, 1H), 2.33 (s, 3H); ESI-MS (negative mode) (m/z): 224 [(M−H)−HCl]$^-$.

Step 4: Coupling of 98 (1.82 g, 6.99 mmol) and alkene 63 (1.63 g, 6.99 mmol) following the procedure described in Example 11, Step 2, gave 4-chloro-6-{5-[4-(4-fluorobenzyl)piperidin-1-ylmethyl]-4,5-dihydroisoxazol-3-yl}-5-methyl-3H-benzoxazol-2-one (1.0 g, 31%):

mp 131–132° C.

IR (KBr): 2922, 1780 cm$^{-1}$ $^1$H NMR (500 MHz, DMSO-$d_6$): δ 12.20 (s, 1H), 7.35 (s, 1H), 7.17 (dd, J 8, 6 Hz, 2H), 7.07 (dd, J 9, 8 Hz, 2H), 4.82–4.76 (m, 1 H), 3.48 (dd, J 17, 11 Hz, 1H), 3.18 (dd, J 17, 8 Hz 1H), 2.91 (m, 2H), 2.58–2.46 (m, 4H), 2.45 (s, 3H), 2.08–1.99 (m, 2H), 1.52–1.42 (m, 3H), 1.22–1.13 (m, 2H)

ESI-MS (m/z): 458 [M+H]$^+$

HPLC: method A, 6.95 min (96.0%); method B, 12.21 min (95.9%) Anal. Calcd for $C_{24}H_{25}ClFN_3O_3$: C, 62.34; H, 5.56; N, 9.09. Found: C, 62.52; H, 5.44; N, 8.88.

EXAMPLE 34

-{5-[4-(4-Fluorophenyl)piperidin-1-ylmethyl]-4,5-dihydroisoxazol-3-yl}-3H-benzoxazol-2-one

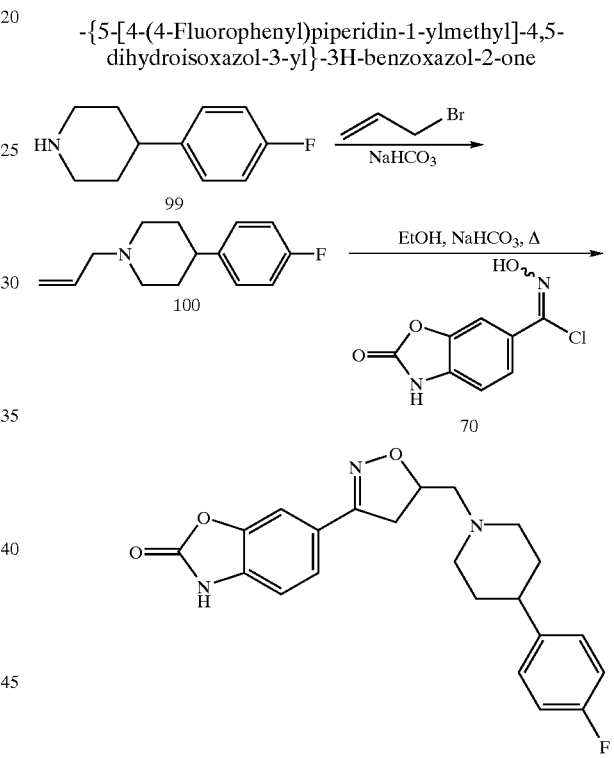

Step 1: Alkene of formula 100 was prepared following the procedure described below for alkene of formula 63 in Example 16, Step 1, to give 1.34 g, (50%):

$^1$H NMR (300 MHz, $CDCl_3$): 7.20–7.15 (m, 2H), 7.00–6.94 (m, 2H), 5.98–5.85 (m, 1H), 5.23 (d, J 16 Hz, 1H), 5.14 (d, J 10, 1H), 3.07–3.02 (m, 4H), 2.48 (dt, J 11, 5 Hz, 1H), 2.07–1.98 (m, 2H), 1.81–1.65 (m, 4H).

Step 2: Coupling of compound of formula 70 and alkene of formula 100 following the procedure described above in Example 17, Step 5, gave 6-{5-[4-(4-fluorophenyl)piperidin-1-ylmethyl]-4,5-dihydroisoxazol-3-yl}-3H-benzoxazol-2-one (719 mg, 70%):

mp 214–217° C.

IR (KBr): 2926, 1774 cm$^{-1}$ $^1$H NMR (500 MHz, DMSO-$d_6$): δ 11.80 (s, 1H), 7.57 (d, J 1 Hz, 1H), 7.48 (dd, J 8, 1 Hz, 1H), 7.27 (dd, J 8, 6 Hz, 2H), 7.15 (d, J 8 Hz, 1H), 7.08 (dd, J 8, 6 Hz, 2H), 4.90–4.84

(m, 1H), 3.49 (dd, J 17, 11 Hz, 1H), 3.18 (dd, J 17, 8 Hz, 1H), 3.05 (d, J 11 Hz, 1H), 3.02 (d, J 11 Hz, 1H), 2.63–2.52 (m, 2H), 2.51–2.47 (m, 1H), 2.20–2.13 (m, 2H), 1.74–1.71 (m, 2H), 1.67–1.58 (m, 2H)

ESI-MS (m/z): 396 [M+H]$^+$

HPLC: method A, 4.83 minutes(98.3%); method B, 10.60 minutes(>99%)

Anal. Calcd for $C_{22}H_{22}FN_3O_3 \cdot 0.25H_2O$: C, 66.07; H, 5.67; N, 10.51. Found: C, 66.13; H, 5.60; N, 10.52.

EXAMPLE 35

6-[5-(4-Phenyl-4-hydroxy)piperidin-1-ylmethyl)-4, 5-dihydroisoxazol-3-yl]-3H-benzoxazol-2-one

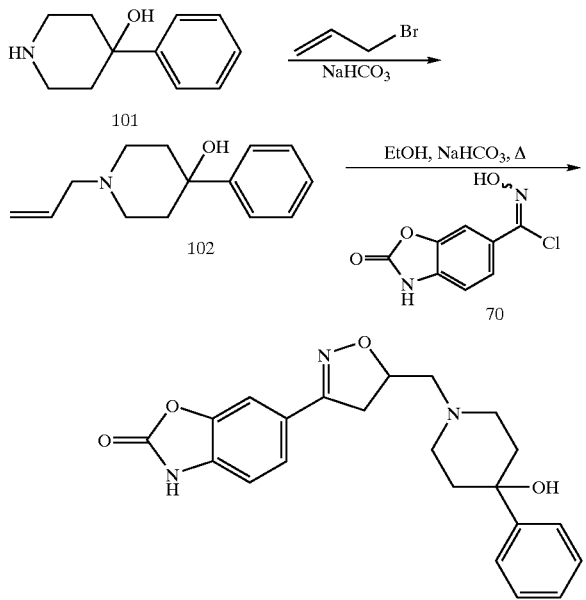

Step 1: Alkene of formula 102 was prepared following the procedure described below for alkene of formula 63 in Example 16, Step 1, to give 1.24 g, (50%):

$^1$H NMR (300 MHz, CDCl$_3$): δ 7.53 (d, J 7 Hz, 2H), 7.36 (dd, J 7, 7 Hz, 1H), 7.28 (d, J 7 Hz, 2H), 6.00–5.86 (m, 1H), 5.25 (d, J 17 Hz, 1H), 5.16 (d, J 10 Hz, 1H), 3.10 (d, J 7 Hz, 2H), 2.86 (d, J 12 Hz, 2H), 2.45 (ddd, J 12, 12, 2 Hz, 2H), 1.31 (ddd, J 13, 13, 4 Hz, 2H), 1.79 (d, J 12 Hz, 2H), 1.63–1.55 (m, 1H).

Step 2: Coupling of compound of formula 70 and alkene of formula 102 following the procedure described above in Example 17, Step 5, gave 6-[5-(4-phenyl-4-hydroxy) piperidin-1-ylmethyl)-4,5-dihydroisoxazol-3-yl]-3H-benzoxazol-2-one (423 mg, 38%):

mp 115–118° C.

IR (KBr): 2951, 1771 cm$^{-1}$ $^1$H NMR (500 MHz, DMSO-d$_6$): □11.80 (s, 1H), 7.57 (s, 1H), 7.48–7.45 (m, 3H), 7.30 (dd, J 8, 8 Hz, 2H), 7.19 (dd, J 7, 6 Hz, 1H), 7.14 (d, J 8 Hz, 1H), 4.90–4.84 (m, 1H), 4.74 (s, 1H), 3.48 (dd, J 17, 11 Hz, 1H), 3.19 (dd, J 17, 8 Hz, 1H), 2.76–2.69 (m, 2H), 2.64–2.50 (m, 4H), 1.92 (dt, J 13, 4 Hz, 2H), 1.60–1.55 (m, 2H)

ESI-MS (m/z): 394 [M+H]$^+$

HPLC: method A, 5.48 min (>99%); method B, 9.63 min (>99%)

Anal. Calcd for $C_{22}H_{23}N_3O_4 \cdot 0.75H_2O$: C, 64.93; H, 6.07; N, 10.33. Found: C, 65.16; H, 6.03; N, 10.27.

EXAMPLE 36

6-(5-{2-[4-(4-Fluorophenyl)piperidin-1-yl]ethyl}-4, 5-dihydroisoxazol-3-yl)-3H-benzoxazol-2-one

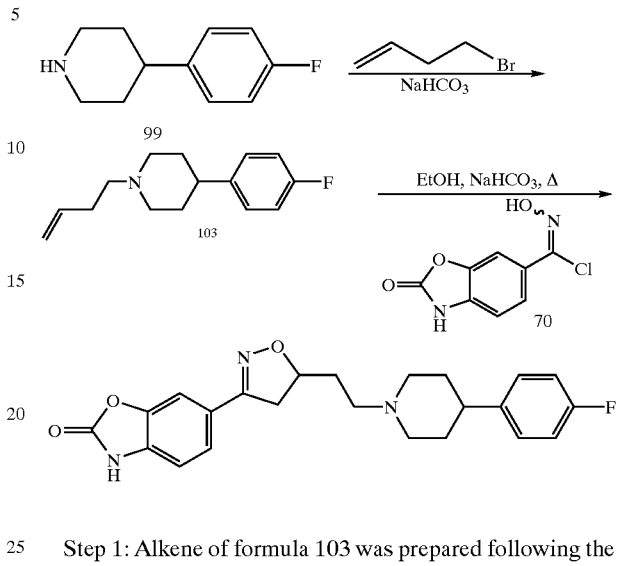

Step 1: Alkene of formula 103 was prepared following the procedure described below for alkene of formula 63 in Example 16, Step 1, to give 2.29 g, (85%):

$^1$H NMR (300 MHz, CDCl$_3$): δ 7.22 (dd, J 9, 8 Hz, 2H), 6.99 (dd, J 9, 8 Hz, 2H), 5.85–5.72 (m, 1H), 5.14 (dd, J 18, 1 Hz, 1H), 5.12 (d, J 10 Hz, 1H), 3.48 (d, J 12 Hz, 2H), 2.88–2.83 (m, 2H), 2.71–2.59 (m, 5H), 2.36–2.31 (m, 2H), 1.97 (d, J 13 Hz, 2H).

Step 2: Coupling of compound of formula 70 and alkene of formula 103 following the procedure described above in Example 17, Step 5, gave 6-(5-{2-[4-(4-fluorophenyl) piperidin-1-yl]ethyl}-4,5-dihydroisoxazol-3-yl)-3H-benzoxazol-2-one (759 mg, 71%):

mp 188–194° C.

IR (KBr): 3448, 2934, 1773, 1654 cm$^{-1}$ $^1$H NMR (500 MHz, DMSO-d$_6$): δ 7.55 (d, J 1 Hz, 1H), 7.46 (dd, J 8, 1 Hz, 1H), 7.23 (dd, J 9, 8 Hz, 2H), 7.14 (d, J 8 Hz, 1H), 7.08 (dd, J 9, 8 Hz, 2H), 4.76–4.70 (m, 1H), 3.45 (dd, J 17, 11 Hz, 1H), 3.12 (dd, J 11, 8 Hz, 1H), 3.00 (d, J 12 Hz, 1H), 2.95 (d, J 12 Hz, 1H), 2.49–2.36 (m, 4H), 2.04–1.98 (m, 2H), 1.86–1.48(m, 6H)

ESI-MS (m/z): 410 [M+H]$^+$

HPLC: method A, 5.58 min (98.8%); method B, 10.45 min (>99%)

Anal. Calcd for $C_{23}H_{24}FN_3O_3 \cdot 0.25H_2O$: C, 66.73; H, 5.97; N, 10.15. Found: C, 66.81; H, 5.99; N, 9.91.

As noted above, the invention compounds are subtype selective NMDA receptor antagonists. The compounds have been evaluated in standard assays commonly used to measure activity. Typical assays were carried out as follows.

Biological Methods

I. Electrophysiological assays at NMDA receptor subunits (in vitro):
  a. The NR1A/NR2B assay:
    (i) Preparation of subunit RNA's:
      cDNA clones encoding the NR1A, NR2A, NR2B, and NR2C rat NMDA receptor subtypes were used. (See, Moriyoshi et al., *Nature (Lond.)*, 1991;354:31–37; Kutsuwada et al., *Nature (Lond.)*, 1992;358:36–41; Monyer et al., *Science*

(Washington, D.C.) 1992;256:1217–1221; Ikeda et al., *FEBS Lett.* 1992;313: 34–38; Ishii et al., *J. Biol. Chem.*, 1993;268:2836–2843 for details of these clones or their mouse homologs). The clones were transformed into appropriate host bacteria and plasmid preparations were made with conventional DNA purification techniques. A sample of each clone was linearized by restriction enzyme digestion of cRNA was synthesized with T3 RNA polymerase. The cRNA was diluted to 400 ng/µl and stored in 1 µl aliquots at −80° C. until injection.

(ii) The Xenopus oocyte expression system:

Mature female Xenopus laevis were anaesthetized (20 to 40 minutes) using 0.15% 3-aminobenzoic acid ethyl ester (MS-222) and 2 to 4 ovarian lobes were surgically removed. Oocytes at developmental stages IV–VI (Dumont, J. N., *J. Morphol.*, 1972;136:153–180) were dissected from the ovary still surrounded by enveloping ovarian tissues. Follicle-enclosed oocytes were micro-injected with 1:1 mixtures of NR1A:NR2A, 2B or 2C; injecting 1 to 10 ng of RNA encoding each receptor subunit. NR1A encoding RNA was injected alone at ~20 ng. Oocytes were stored in Barth's medium containing (in mM):NaCl, 88; KCl, 1; CaCl$_2$, 0.41; Ca (NO$_3$)$_2$, 0.33; MgSO$_4$, 0.82 NaHCO$_3$, 2.4; HEPES 5, pH 7.4, with 0.11 mg/nL gentamicin sulphate. While oocytes were still surrounded by enveloping ovarian tissues the Barth's medium was supplemented with 0.1% bovine serum. Oocytes were defolliculated 1 to 2 days following injections by treatment with collagenase (0.5 mg/nL Sigma Type I for 0.5 to 1 hour) (Miledi and Woodward, *J. Phsyiol. (Lond.)*, 1989;416:601–621) and subsequently stored in serum-free medium.

(iii) Electrical recordings:

Electrical recordings were made using a conventional two-electrode voltage clamp (Dagan TEV-200) over periods ranging between 3 to 21 days following injection. (Woodward et al., *Mol. Pharmacol.*, 1992;41:89–103). Oocytes were placed in a 0.1 mL recording chamber continuously perfused (5–15 mL min$^{-1}$) with frog Ringer's solution containing (in mM):NaCl, 115; KCL, 2; BaCl$_2$, 1.8; HEPES, 5; pH 7.4. Drugs were applied by bath perfusion. Using oocytes expressing different subunit combinations of NMDA receptor, NMDA currents were activated by co-application of glutamate (100 µM) and glycine (1–100 µM) as agonists. Inhibitory potency of the novel antagonists of this invention was assessed on responses elicited by fixed concentrations of glutamate and glycine agonists, by measuring reductions in current induced by progressively increasing concentrations of invention compounds.

(iv) Concentration-inhibition curves:

Concentration-inhibition curves were fitted with equation 1

$$I/I_{control}=1/(1+([antagonist]/10^{-pIC50})^n) \qquad \text{Eq. 1}$$

in which $I_{control}$ is the current evoked by the agonists alone, $pIC_{50}=-\log IC_{50}$, $IC_{50}$ is the concentration of invention compound that produced half maximal inhibition of the electrical current, and n is the slope factor (see De Lean et al., *Am. J. Physiol.*, 1978;235: E97–102). For incomplete curves, analysis by fitting was unreliable, and $IC_{50}$ values were calculated by simple regression over linear portions of the curves using an ORIGIN software (Microcal Software, Boston, Mass.), a computer program for collection, analysis, and presentation of scientific data. The results of this assay for representative invention compounds is given in Table 1, in the column labeled "NR1A/NR2B", and the activity is reported as the $IC_{50}$ in micromolar (µM) concentration.

b. [$^3$H]Ifenprodil Binding Assay (IFPNR) Protocol:

(i) Materials:

Ifenprodil, [phenyl-$^3$H]-(specific activity, 66.2 Ci/mmol) was purchased from Dupont NEN Research Products (Boston, Mass.). Ifenprodil tartrate was purchased from Research Biochemicals International (Natick, Mass.). HEPES, glutamate and glycine were purchased from Sigma Chemical Co. (St. Louis, Mo.).

(ii) Preparations:

All buffers and reagents used in assay incubations or to dissolve drugs were prepared using water purified through a Milli-Q reverse osmosis system (Millipore Corp., Bedford, Mass.) and treated with UV emissions. Prior to use in the assays buffers were further filtered through a sterile Coming filtration unit (Coming Glass Works, Coming, N.Y.) containing a 0.2 micron filter. Buffer used to rinse the membranes on the assay filters was prepared with purified water, but was not refiltered and was stored no longer than 5 days. Stock solutions of the drugs (usually 10 mM) were dissolved in 20 mM HEPES-KOH buffer pH 7.4 (assay buffer) with the addition of 1 to 5 µL of glacial AcOH, if needed to keep them in solution. Eliprodil was used as the reference NMDA antagonist. A stock solution of eliprodil was prepared, and was buffered with the addition of 10% DMSO. All subsequent dilutions from the stock solution were made in buffer.

An extensively washed buffy coat membrane fraction was prepared from frozen adult rat forebrains (Zivic-Miller Laboratories, Inc., Zelienople, Pa.) as described by Coughenour L. L.; Cordon, J. J., *J. Pharmacol. Exp. Ther.*, 1997;280:584–592, and stored at −80° C. On the day of the assay, pellets of the frozen membrane fractions were resuspended in 35 mL of assay buffer at pH 7.4 using a POLYTRON (Kinematica A. G. Company, Littau, Switzerland) mixer at setting 6. After incubation at 37° C. for 30 minutes in a shaking water bath, the homogenate was centrifuged 40,000×g for 10 minutes at 4° C. The pellets were resuspended in fresh buffer and centrifuged 3 more times before final suspension for use in the assay.

(iii) [$^3$H]Ifenprodil Binding protocol:

Triplicate incubations were carried out in a volume of 0.5 mL in 1.3 mL polypropylene tubes (Marsh Biomedical Products Inc, Rochester, N.Y.) for 2 hours at room temperature. Incubations contained invention compounds, membranes (100–200 µg protein) and 4 nM [$^3$H]-ifenprodil in 20 mM HEPES-KOH buffer, pH 7.4 (assay buffer). Assays were started by addition of the membranes. Bound radioligand was separated by filtration under reduced pressure using a TOMTEC Mach II, 96-well cell harvester (Tomtec Inc, Orange, Conn.). Filtration was through Whatman GF/B glass fiber filters (Whatman Ltd., Maidstone, England), which had been soaked for at least 15 minutes in 0.3% polyethylenimine and allowed to air dry. The filters were rinsed with 3 mL of ice cold assay buffer within 6 seconds. Air was allowed to pass through the filters for an additional 10 seconds to remove residual moisture. The filter mat was supported on a cold (−20° C.) TEFLON (E. I. Du Pont de Nemours and Company, Wilmington, Del.) coated support, and filters from individual wells were separated and placed in Mini Poly-Q vials (Becklman Instruments Inc, Fullerton, Calif.) and filled with 4 mL of scintillation cocktail (Beckman Ready Protein+). Radioactivity retained on the filter was determined by liquid scintillation spectrophotometry. Nonspecific binding was defined as the binding in the presence of 1 mM ifenprodil. Ninety percent of the total binding of ifenprodil was specific binding at the NR1A/NR2B NMDA receptor subtype active site (as opposed to binding at a remote site).

(iv) Data analysis:

Binding curves were statistically analyzed for a best 1- or 2-site competition fit using GRAPHPAD PRISM software (GraphPad Software Inc, San Diego, Calif.), a computer program used to analyze and graph scientific data. The normalized data was fitted by nonweighted nonlinear regression to either $$y = \text{Bottom} + \frac{(\text{Top} - \text{Bottom})}{1 + 10^{x - \text{Log}EC_{50}}} \text{ or}$$

$$y = \text{Bottom} + (\text{Top} - \text{Bottom})\frac{\text{Fraction} - 1}{1 + 10^{x - \text{Log}EC_{50-1}}} + \frac{1 - \text{Fraction} - 1}{1 + 10^{x - \text{Log}EC_{50-2}}}$$

Control data was entered as 100%, and no parameters were constrained. Inhibition curves were compared by Anova with post-test comparisons of the log $IC_{50}$ with Dunnett's multiple comparisons post-test or Student's nonpaired, 2-tailed t-test using GraphPad INSTAT (Harvey Motulsky, San Diego, Calif.) software.

The results of the IFPNR binding assay are reported as $IC_{50}$s in micromolar (EM) concentrations in Table 1 to Table 5 in the columns labeled "IFPNR".

II. Animal Models:

a. The Formalin Footpad Test (FT):

The FT model was used to test invention compounds for pain alleviating properties. The model produces a biphasic response in a test animal that results from a change in pain intensity over time. The FT model utilizes an injection of dilute formalin into the hindpaw of a rodent, which produces high intensity acute pain behaviors which are measured for the first 10 minutes post formalin injection (early phase responding). High intensity acute pain behaviors include rapid licking or biting of the injected hindpaw. The second phase is a prolonged period of lower intensity pain behaviors (late phase responding) which are measured from 11 to 45 minutes post-formalin injection.

(i) Test animals:

Male Wistar albino rats (Harlan Sprague-Dawley Labs), weighing approximately 100 g at the time of testing, were used. Animals were group-housed and acclimated to the housing facility for 1 week prior to testing. Animals were maintained on a 12-hour/12-hour light/dark cycle and fed block rodent chow. From 4 to 8 animals were randomly assigned to either a vehicle-only dose group or a vehicle-plus invention compound treatment group on the day of testing.

(ii) Test apparatus:

The testing apparatus was a 16"×8" box divided into two 8"×8" testing chambers. Each testing chamber comprised a floor and 3 walls made of clear plastic mirrors, and a fourth wall which was clear plastic that allowed observation of animal behavior. The top of each chamber was covered with a metal screen during testing to prevent animals from climbing out of the chamber. Two animals were tested simultaneously in the adjoining boxes, but animals were unable to observe one another.

(iii) Procedure:

Animals were weighed and placed into holding cages (2 animals per cage) in the testing room prior to dosing. Following approximately 30 minutes of acclimation to the testing room, each pair of animals was administered orally (PO) by gavage a mixture of invention compound plus vehicle or vehicle alone. The treated animals were then placed in individual test chambers and allowed to acclimate to the chambers for at least 20 minutes. Then 50 $\mu L$ of a 2.5% solution of formalin in vehicle was injected subcutaneously (SC) in the plantar surface of the left hindpaw from 30 to 120 minutes after administration of the invention compound. A session timer was started following the formalin injection, and the amount of time the animal spent licking or biting the injected paw was clocked with a hand-held stopwatch. The cumulative time spent engaging in a pain response was manually recorded at 5-minute intervals for 45 minutes post formalin injection. Early phase responding included Minutes 0 to 10, and late phase responding included Minutes 11 to 45. At the end of the testing period, animals were sacrificed using carbon dioxide.

(iv) Data Analysis:

As recited above, responding was divided into early phase (total time spent licking during Minutes 0 to 10 following the formalin injection) behaviors and late-phase (total time spent licking during Minutes 11 to 45 post formalin injection) behaviors. Time values were obtained for the vehicle only dose group (the control group) and each treatment group. For the purpose of measuring the activity of the invention compounds, the late-phase time values of a given treatment group were compared statistically to the late-phase time values obtained for the control group using either Student's t-test or One-way Analysis of Variants (ANOVA).

The results are reported in Table 1 and Table 2 under the heading "FT" as the dose tested in milligrams f invention compound per kilogram of test animal (mg/kg). A compound was characterized as active if it produced a statistically-significant decrease in the time animals administered invention compound plus vehicle spent engaging in pain-related behaviors compared to the time spent by animals receiving vehicle alone. Invention compounds were typically administered at 10 and/or 30 mg/kg, and the activities are reported in the tables as either being greater than (>) or less than (<) these doses.

b. The 6-OHDA Lesioned Rat Assay (6-OHDA):

The 6-OHDA model is used to test compounds of the invention for anti-Parkinsonism activity.

(i) 6-OHDA lesioned rat assay protocol:

6-Hydroxydopamine-lesioned rats were used (see Ungerstedt U, Arbuthnott G W: "Quantitative recording of rotational behavior in rats after 6-hydroxy-dopamine lesions of the nigrostraiatal dopamine system", *Brain Res.*, 1971;24(3):485–493). Adult male Sprague-Dawley rats were anesthetized with chloral hydrate, and unilateral lesions of the nigrostriatal dopamine system were accomplished by infusion of 8 μg of 6-hydroxydopamine HBr (6-OHDA) into the right medial forebrain bundle. Rats were pretreated 30 minutes before surgery with desipramine HCl 25 mg/kg intraperitoneally (IP) to protect noradrenergic neurons, and pargyline 25 mg/kg IP to potentiate the effects of 6-OHDA. A minimum of 3 weeks after surgery, the rotational behavior induced by apomorphine HCL 50 μg/kg administered subcutaneously (SC) was assessed. Only rats demonstrating more than 100 contraversive turns/hour to apomorphine were used for the present experiments.

(ii) Measurement of animal behavior:

Rotational behavior was measured using an automatic rotometer system (Rotorat Rotational Activity System, MED Associates, Georgia, Vt.). Antiparkinsonian activity was assessed as the ability of the invention compounds to potentiate the contraversive rotation induced by L-DOPA methyl ester, dosed at 10 mg/kg SC, over a 6-hour period. Experiments were conducted using a crossover paradigm where each rat received either vehicle plus L-DOPA, or an invention compound plus L-DOPA, in randomized order. Rats were tested at 7-day intervals. In experiments in which the invention compounds were tested orally (PO), rats were food deprived for 16 hours.

(iii) Data analysis:

Statistical analysis between treatment groups was performed using a paired t-test. The results are reported in Table 1 and Table 2 under the heading "6-OHDA" as the minimum effective dose (MED) in milligrams of invention compound per kilogram of test animal (mg/kg) required to produce a statistically-significant increase in total contraversive rotations in rats administered invention compound compared to rats receiving L-DOPA alone. Invention compounds were typically administered at 10 mg/kg and/or 30 mg/kg, and the MED's are reported in the tables as either being greater than (>) or less than (<) these doses.

TABLE 1

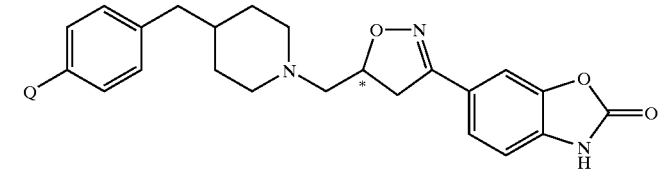

| Example No. | Q | * | IFPNR (IC$_{50}$ μM) | NR1A/NR2B (IC$_{50}$ μM) | 6-OHDA (mg/kg) | FT (mg/kg) |
|---|---|---|---|---|---|---|
| 1 | H | R,S | 0.033 | 0.080 | >10 (po) | >10 |
| 3 | F | R,S | 0.030 | NT[a] | >10 (po); <30 (po) | >10; <30 |
| 4a | F | (+) | 0.016 | NT | >10 (po); <30 (po) | <10 |
| 4b | F | (−) | 0.280 | NT | >30 (po) | >30 |

[a]NT means not tested.

TABLE 2

[Structure: Q—C6H4—CH2—(piperidine)—N—CH2—B—(benzo-fused ring with X1 and =Y(O,S), NH)]

| Example No. | B | Q | X1 | * | IFPNR IC50 μm | FT (mg/kg) | Y Y |
|---|---|---|---|---|---|---|---|
| 5 | 3,5-dimethyl-4,5-dihydroisoxazol-5-yl | F | O | R,S | 0.047 | >30 | O |
| 6 | 2,5-dimethylthiazol-5-yl | F | O | NC | 0.54 | NT | O |
| 7 | 2,5-dimethylthiazol-5-yl | F | S | NC | 0.45 | NT | S |
| 8 | 2,5-dimethylthiazol-5-yl | H | NH | NC | 0.066 | NT | O |
| 9 | 2,5-dimethyloxazol-5-yl | F | S | NC | >1 | NT | O |
| 10 | 2,5-dimethyloxazol-5-yl | H | O | NC | >1 | NT | O |
| 11 | 2,5-dimethyloxazol-5-yl | H | CH2 | NC | >1 | NT | O |
| 12 | 2,5-dimethyl-4,5-dihydrothiazol-5-yl | F | O | R,S | 0.394 | NT | O |
| 13 | 2,5-dimethyl-4,5-dihydrothiazol-5-yl | H | O | R,S | 0.101 | NT | O |
| 15 | 3,5-dimethylisoxazol-5-yl | F | O | NC | 0.499 | NT | O |
| 21 | 3,5-dimethyl-4,5-dihydroisoxazol-5-yl (5-Me) | F | O | R,S | 0.011 | NT | O |

TABLE 2-continued

| Example No. | B | Q | X₁ | * | IFPNR IC₅₀ μm | FT (mg/kg) | Y Y |
|---|---|---|---|---|---|---|---|
| 22 | HO₂C-[5-methyl-3-methyl-4,5-dihydroisoxazole] | F | O | R,S | 0.788 | NT | O |
| 23 | MeO₂C-[5-methyl-3-methyl-4,5-dihydroisoxazole] | F | O | R,S | — | NT | J |

[a]NC means no chiral center;
[b]NT means not tested.

TABLE 3

| Example No. | V | B | h | Q | R₂ | * | IFPNR IC₅₀ (μM) |
|---|---|---|---|---|---|---|---|
| 2 | CH₂ | 3,4,5-trimethylisoxazole | 1 | H | H | NC[a] | >1 |
| 14 | CH₂ | 2,5-dimethylthiazoline | 1 | H | H | R,S | 0.688 |
| 17 | CH₂ | 3,5-dimethyl-4,5-dihydroisoxazole | 1 | H | OH | R,S | 0.006 |
| 18 | C=O | 3,5-dimethyl-4,5-dihydroisoxazole | 1 | F | H | R,S | >1 |
| 19 | CH₂CH₂ | 3,5-dimethyl-4,5-dihydroisoxazole | 1 | F | H | R,S | 0.400 |
| 20 | CH₂ | 3,5-dimethyl-4,5-dihydroisoxazole | 1 | F | OH | R,S | 0.008 |

TABLE 3-continued

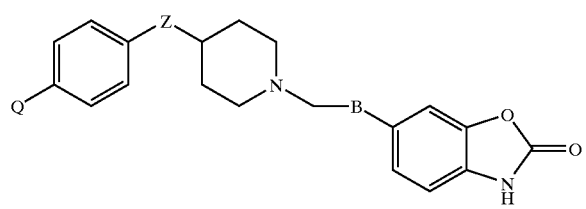

| Example No. | V | B | h | Q | R$_2$ | * | IFPNR IC$_{50}$ ($\mu$M) |
|---|---|---|---|---|---|---|---|
| 24 | CH$_2$ | (5-methyl-3-yl isoxazoline) | 1 | F | CO$_2$Et | R,S | — |
| 25 | CH$_2$ | (5-methyl-3-yl isoxazoline) | 1 | F | CO$_2$H | R,S | — |
| 34 | CH$_2$ | (5-methyl-3-yl isoxazoline) | 0 | F | H | R,S | 0.280 |
| 35 | CH$_2$ | (5-methyl-3-yl isoxazoline) | 0 | H | OH | R,S | >1 |
| 36 | CH$_2$CH$_2$ | (5-methyl-3-yl isoxazoline) | 0 | F | H | R,S | >1 |

[a]NC means no chiral center

TABLE 4

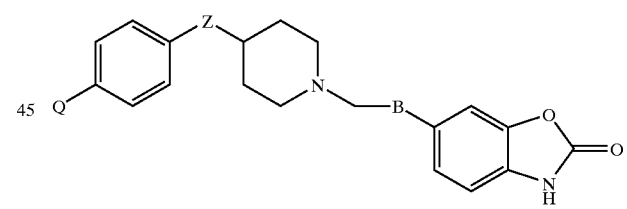

| Example No. | B | Z | Q | * | IFPNR IC$_{50}$ ($\mu$M) |
|---|---|---|---|---|---|
| 27 | (5-methyl-3-yl isoxazoline) | O | F | R,S | 0.059 |
| 28 | (5-methyl-3-yl isoxazoline) | S | F | R,S | 0.018 |
| 29 | (5-methyl-3-yl isoxazoline) | S=O | F | R,S | 0.600 |
| 30 | (5-methyl-3-yl isoxazoline) | C=O | F | R,S | 0.759 |
| 31 | (5-methyl-3-yl isoxazoline) | CH(OH) | F | R,S | >1 |
| 32 | (5-methyl-3-yl isoxazoline) | CMe(OH) | F | R,S | >1 |

TABLE 5

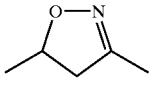

| Example No. | V | B | $R_3$ | $X_1$ | $X_2$ | $X_3$ | * | IFPNR $IC_{50}$ ($\mu M$) |
|---|---|---|---|---|---|---|---|---|
| 16 | $CH_2$ | 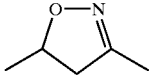 | H | S | H | H | R,S | 0.002 |
| 26 | $CH_2$ | | OH | O | H | H | R,S | 0.023 |
| 33 | $CH_2$ | 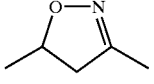 | H | O | Me | Cl | R,S | 0.014 |

As shown in the above tables, compounds of the invention are potent antagonists at the NMDA receptor and orally active in vivo in models of Parkinson's disease and pain.

In addition to the oral dosing forms described above, the compounds of the invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. The following dosage forms may comprise as the active component a compound of Formula I or a pharmaceutically acceptable salt thereof.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 to 100 mg preferably 0.5 to 100 mg according to the particular application and the potency of the active component. The composition can, if desired, also contain other compatible therapeutic agents.

In therapeutic use as antagonists or as agents for the treatment of diseases, the compounds utilized in the pharmaceutical method of this invention are administered at the initial dosage of about 0.01 mg to about 100 mg/kg daily. A daily dose range of about 0.01-mg to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

Examples of pharmaceutical preparations of the compounds of the invention is described below. Such preparations can be administered to a human from one to six times a day for treatment of disease caused by over excitation of NMDA receptor channel complexes.

EXAMPLE 37

Tablet Formulation:

| Ingredient | Amount (mg) |
| --- | --- |
| Compound of Example 1 | 25 |
| Lactose | 50 |
| Cornstarch (for mix) | 10 |
| Cornstarch (paste) | 10 |
| Magnesium stearate (1%) | 5 |
| Total | 100 |

The compound of Example 1, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet.

EXAMPLE 38

Coated Tablets

The tablets of Example 17 are coated in a customary manner with a coating of sucrose, potato starch, talc, tragacanth, and colorant.

EXAMPLE 39

Injection Vials

The pH of a solution of 500 g of the compound of Example 1 and 5 g of disodium hydrogen phosphate is adjusted to pH 6.5 in 3 L of double-distilled water using 2 M hydrochloric acid. The solution is sterile filtered, and the filtrate is filled into injection vials, lyophilized under sterile conditions, and aseptically sealed. Each injection vial contains 25 mg of the compound of Example 1.

EXAMPLE 40

Suppositories

A mixture of 25 g of the compound of Example 1, 100 g of soya lecithin, and 1400 g of cocoa butter is fused, poured into molds, and allowed to cool. Each suppository contains 25 mg of the compound of Example 1.

EXAMPLE 41

Solution

A solution is prepared from 1 g of the compound of Example 1, 9.38 g of $NaH_2PO_4.2H_2O$, 28.48 g of $Na_2HPO_4.12H_2O$, and 0.1 g benzalkonium chloride in 940 mL of double-distilled water. The pH of the solution is adjusted to pH 6.8 using 2 M hydrochloric acid. The solution is diluted to 1.0 L with double-distilled water, and sterilized by irradiation. A 25 mL volume of the solution contains 25 mg of the compound of Example 1.

EXAMPLE 42

Ointment 500 mg of the compound of Example 1 is mixed with 99.5 g of petroleum jelly under aseptic conditions. A 5 g portion of the ointment contains 25 mg of the compound of Example 1.

EXAMPLE 43

Capsules 2 kg of the compound of Example 1 are filled into hard gelatin capsules in a customary manner such that each capsule contains 25 mg of the invention compound.

EXAMPLE 44

Ampoules

A solution of 2.5 kg of the compound of Example 1 is dissolved in 60 L of double-distilled water. The solution is sterile filtered, and the filtrate is filled into ampoules. The ampoules are lyophilized under sterile conditions and aseptically sealed. Each ampoule contains 25 mg of the compound of Example 1.

While the forms of the invention exemplified herein such as, for example, the named species of Formula IV or the recitation of treatment of pain or Parkinson's disease constitute preferred embodiments of the invention, many other preferred embodiments are possible. It is not intended that the preferred embodiments of compounds of Formula IV, or preferred methods of use of said compounds, recited above should, in any manner, limit or restrict the invention from the full scope claimed herein.

In the claims:
1. A compound of formula (IV)

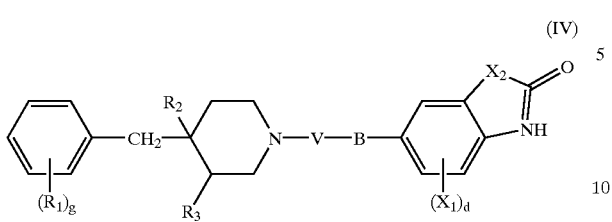

and pharmaceutically acceptable salts thereof wherein:
X$_2$ is selected from O, S, NH and CH$_2$;
Z is O or S;
R$_1$ is independently selected from alkyl, substituted alkyl, alkenyl, substituted alkenyl, alkoxy, substituted alkoxy, alkylaminoalkyl, hydroxyalkyl, (aminocarbonyl)-alkyl, (alkylthio)-alkyl, carboxyalkyl, haloalkyl and halogen;
g is an integer from 0 to 3;
R$_2$ is H or OH;
R$_3$ is H or OH;
V is (CH$_2$)$_n$ or (CH$_2$)$_m$—C=O, wherein n is an integer from 1 to 4 and m is an integer from 0 to 4;
B is a ring selected from

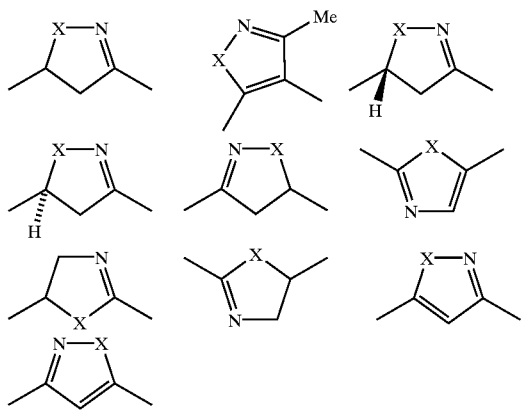

wherein X is selected from O, S and N—R, wherein R is hydrogen or alkyl;
X$_1$ is alkyl, substituted alkyl, alkenyl, substituted alkenyl, alkoxy, substituted alkoxy, aralkyl, substituted aralkyl, halogen, haloalkyl, cyano, nitro, amino, aminoalkyl, alkylaminoalkyl, hydroxyalkyl, , carboxyalkyl, (aminocarbonyl)-alkyl, (alkylthio)-alkyl or C(O)-alkyl; and
d is an integer from 0 to 2.

2. A compound of formula IV according to claim 1 selected from:
6-[5-(4-Benzylpiperidin-1-ylmethyl)-4,5-dihydroisoxazol-3-yl]-3H-benzoxazol-2-one;
6-[5-(4-Benzylpiperidin-1-ylmethyl)-3-methylisoxazol-4-yl]-3H-benzoxazol-2-one; 6-{5-[4-(4-fluorobenzyl)piperidin-1-ylmethyl]-4,5-dihydroisoxazol-3-yl}-3H-benzoxazol-2-one hydrochloride;
(+)-6-{5-[4-(4-fluorobenzyl)piperidin-1-ylmethyl]-4,5-dihydroisoxazol-3-yl}-3H-benzoxazol-2-one;
(−)-6-{5-[4-(4-fluorobenzyl)piperidin-1-ylmethyl]-4,5-dihydroisoxazol-3-yl}-3H-benzoxazol-2-one;
6-{3-[4-(4-Fluorobenzyl)piperidin-1-ylmethyl]-4,5-dihydroisoxazol-5-yl}-3H-benzoxazol-2-one;
6-{2-[4-(4-Fluorobenzyl)piperidin-1-ylmethyl]thiazol-5-yl}-3H-benzoxazol-2-one;
6-{2-[4-(4-fluorobenzyl)piperidin-1-ylmethyl]thiazol-5-yl}-3H-benzothiazol-2-one;
5-[2-(4-Benzylpiperidin-1-ylmethyl)thiazol-5-yl]-1,3-dihydrobenzimidazole-2-thione;
6-{2-[4-(4-Fluorobenzyl)piperidin-1-ylmethyl]oxazol-5-yl}-3H-benzothiazol-2-one;
6-[2-(4-Benzylpiperidin-1-ylmethyl)oxazol-5-yl]-3H-benzoxazol-2-one;
5-[2-(4-Benzylpiperidin-1-ylmethyl)oxazol-5-yl]-1,3-dihydroindol-2-one;
6-{5-[4-(4-Fluorobenzyl)piperidin-1-ylmethyl]-4,5-dihydrothiazol-2-yl}-3H-benzoxazol-2-one;
6-[5-(4-Benzylpiperidin-1-ylmethyl)-4,5-dihydrothiazol-2-yl]-3H-benzoxazol-2-one;
6-[2-(4-Benzylpiperidin-1-ylmethyl)-4,5-dihydrothiazol-5-yl]-3H-benzoxazol-2-one;
6-{5-[4-(4-Fluorobenzyl)piperidin-1-ylmethyl]isoxazol-3-yl}-3H-benzoxazol-2-one;
6-{5-[4-(4-Fluorobenzyl)piperidin-1-yl]methyl}-4,5-dihydroisoxazol-3-yl}-3H-benzothiazol-2-one;
6-[5-(4-Benzyl-4-hydroxypiperidin-1-ylmethyl)-4,5-dihydroisoxazol-3-yl]-3H-benzoxazol-2-one;
6-{5-[4-(4-Fluorobenzyl)piperidine-1-carbonyl]-4,5-dihydroisoxazol-3-yl}-3H-benzoxazol-2-one;
6-(5-{2-[4-(4-Fluorobenzyl)piperidin-1-yl]ethyl}-4,5-dihydroisoxazol-3-yl)-3H-benzoxazol-2-one;
6-{5-[4-(4-Fluorobenzyl)-4-hydroxypiperidin-1-ylmethyl]-4,5-dihydroisoxazol-3-yl}-3H-benzoxazol-2-one;
6-{5-[4-(4-Fluorobenzyl)piperidin-1-ylmethyl]-5-methyl-4,5-dihydroisoxazol-3-yl}-3H-benzoxazol-2-one;
6-{5-[4-(4-Fluorobenzyl)-3-hydroxypiperidin-1-ylmethyl]-4,5-dihydroisoxazol-3-yl}-3H-benzoxazol-2-one; and
4-Chloro-6-{5-[4-(4-fluorobenzyl)piperidin-1-ylmethyl]-4,5-dihydroisoxazol-3-yl}5-methyl-3H-benzoxazol-2-one.

3. A compound according to claim 1 which is (+)-6-{5-[4-(4-fluoro-benzyl)-piperidin-1-ylmethyl]-4,5-dihydroisoxazol-3-yl}-3H-benzoxazol-3-one.

4. A compound according to claim 1 which is (−)-6-{5-[4-(4-fluoro-benzyl)-piperidin-1-ylmethyl]-4,5-dihydroisoxazol-3-yl}-3H-benzoxazol-3-one.

5. A pharmaceutical composition comprising a therapeutically effective amount of a compound of Formula IV, or a pharmaceutically acceptable salt thereof, together with a diluent, carrier, or excipient.

6. A pharmaceutical composition according to claim 5 comprising a therapeutically effective amount of a compound selected from the group consisting of:
(+)-6-{5-[4-(4-Fluoro-benzyl)-piperidin-1-ylmethyl]-4,5-dihydro-isoxazol-3-yl}-3H-benzoxazol-3-one; and
(−)-6-{5-[4-(4-Fluoro-benzyl)-piperidin-1-ylmethyl]-4,5-dihydro-isoxazol-3-yl}-3H-benzoxazol-3-one.

7. A method of treating disorders responsive to the selective blockade of the N-methyl-D-aspartate receptor subtypes in a mammal, including a human, suffering therefrom, comprising administering a compound of Formula IV, or a pharmaceutically acceptable salt thereof.

8. A method according to claim 7 wherein the disorders are selected from stroke, cerebral ischemia, central nervous system disorders, depression, trauma, hypoglycemia, neurodegenerative disorders, including Parakinson's disease, anxiety, migraine headache, convulsions, aminoglycoside antibiotics-induced hearing loss, psychosis, glaucoma, CMV retinitis, opioid tolerance or withdrawal, pain, including chronic pain, neuropathic pain, or surgical pain, and urinary incontinence.

* * * * *